United States Patent [19]
Johnson et al.

[11] Patent Number: 6,093,739
[45] Date of Patent: Jul. 25, 2000

[54] SYNTHESIS OF LONG WAVELENGTH ABSORBING PHOTOSENSITIZERS

[75] Inventors: Claire K. Johnson, Munich, Germany; David Dolphin, Vancouver, Canada

[73] Assignee: The University of British Columbia, Canada

[21] Appl. No.: 09/196,761

[22] Filed: Nov. 20, 1998

[30] Foreign Application Priority Data

Nov. 21, 1997 [CA] Canada .................................... 2221912

[51] Int. Cl.[7] .................................................. A61K 31/40
[52] U.S. Cl. ......................... 514/410; 540/145; 540/472; 540/474; 514/185
[58] Field of Search .................................... 540/145, 472, 540/474; 514/185, 410

[56] References Cited

U.S. PATENT DOCUMENTS

| | | | |
|---|---|---|---|
| 4,512,762 | 4/1985 | Spears ...................................... | 514/410 |
| 4,566,636 | 1/1986 | Sachar et al. ........................... | 239/698 |
| 4,920,143 | 4/1990 | Levy et al. .............................. | 514/410 |
| 5,059,619 | 10/1991 | Haeger et al. .......................... | 514/410 |
| 5,095,030 | 3/1992 | Levy et al. .............................. | 514/410 |
| 5,171,749 | 12/1992 | Levy et al. .............................. | 514/410 |
| 5,399,583 | 3/1995 | Levy et al. .............................. | 514/410 |
| 5,776,966 | 7/1998 | North ...................................... | 514/410 |
| 5,789,433 | 8/1998 | Chan et al. .............................. | 514/410 |

FOREIGN PATENT DOCUMENTS 2221912 11/1997 Canada .

OTHER PUBLICATIONS

Alonso et al., Tetra. Letters., vol. 38, No. 15, pp. 2757–8., 1997.
Johnson et al., Tetra Letters., vol. 39, pp. 4753–6., 1998.
A.R. Morgan et al., "Synthesis of Benzochlorin Iminium Salts with Improved Photosensitizing Properties", Tetrahedron Letters, 35, p. 5347, 1994.
A.R. Morgan et al., "New Sensitizes for Photodynamic Therapy: Controlled Synthesis of Purpurins and Their Effect on Normal Tissue", J. Med. Chem., 32, p. 904–908, 1989.
A.R. Morgan et al., "Observations on the Synthesis and Spectroscopic Characteristics of Purpurins", J. Org. Chem., 51, p. 1347–1350, 1986.
A.R. Morgan et al., "Observations on the Synthesis and in vivo Photodynamic Activity of Some Benzochlorins", Photochem. Photobiol. 55, p. 133, 1992.
A.R. Morgan et al., "Metallopurpurins and Light: Effect on Transplantable Rat Bladder Tumors and Murine Skin", Photochem. Photobiol., 51, p. 589, 1990.
A.W. Johnson et al., "meso–Substitution Products of Etioporphyrin I", J. Chem Soc. (c), p. 794–798, 1966.

(List continued on next page.)

*Primary Examiner*—Mukund J. Shah
*Assistant Examiner*—Pavanaram K Sripada
*Attorney, Agent, or Firm*—Morrison & Foerster

[57] ABSTRACT

The present invention provides for novel therapeutic macrocycle compounds useful in photodynamic therapy that are based on the chlorin ring system. The macrocycle compounds have, in many cases, wavelengths of activation at about 670 nm, characteristics of chlorins, and are stabilized against oxidation by the attachment to the chlorin ring of a structure that comprises one or more exocyclic rings that contribute at least one nitrogen atom. Protonation or covalent modification of this nitrogen atom, or other covalent modification of the one or more exocyclic rings permits optimization of pharmacalogically relevant properties including, for example, solubility. Representative chlorins include the pyridochlorins depicted as follows

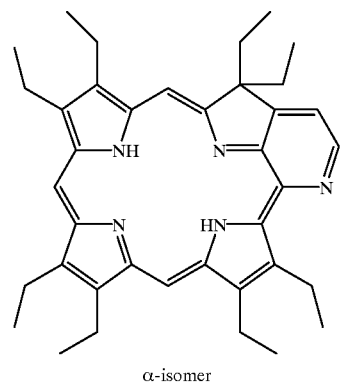

α-isomer

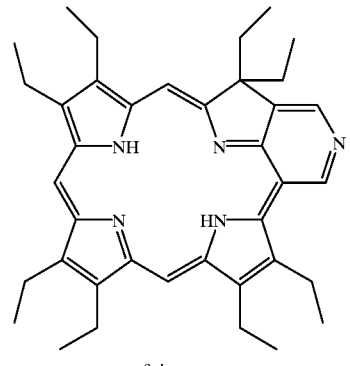

β-isomer

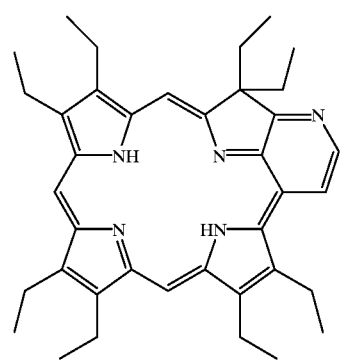

γ-isomer

4 Claims, 21 Drawing Sheets

OTHER PUBLICATIONS

A.W. Johnson et al., "The Nitration and Hydroxylation of Etioporphyrin I" Chem. Soc. p. 4303–4312, 1965.

Arnold et al., "Wittig Condensation Products from Nickel meso–Formyl–octaethyl–porphyrin and aetioporphyrin I and Some Cyclisation Reactions" Journal of the Chemical Society: 12 (1978).

B.C. Robinson et al., "Functionalized Benzochlorins for PDT", SPIE Optical Methods for Tumor Treatment and Detection: Mechanisms and Techniques in Photodynamic Therapy V, 2675, p. 179, 1996.

C. Alsonso et al. "Reaction of β–Amino–meso–Tetraphenylporphyrin with α,β–Unsaturated Carbonyl Compounds: An approach to fused Pyridinoporphyrins", Tetrahedron Letters 38(15), pp. 2757–2758, 1997.

D. Skalkos et al. "Iminium Salt Benzochlorins: Structure-Activity Relationships Studies", Photochem. Photobiol., 59, p. 175 1994.

D. Yashunsky et al. "Chemistry of meso–Dimethylamino-propenyl–porphyrins and –bisporphyrins: the Synthesis of Australochlorin, a Benzochlorin Isomer", Aust. J. Chem., 50, p. 487–493, 1997.

J.H. Fuhrhop et al., "Preparation and Reactivity of Sterically Crowded Porphyrios", Angew. Chem. Int. Ed. Engl., 14, p. 361, 1975.

J.S. Davies et al., "NMR Spectroscopic and X–Ray Crystallographic Studies on the Structure, Stereochemistry and Conformation of a Series of 9, 11–Cyclic . . . " J. Chem. Soc., Perkin Trans., 2, p. 201, 1991.

K. Tsuda et al. "An Aromatization Reaction of a Cross–Conjugated Dienone System with Zinc" J. Org Chem., 28, p. 795, 1963.

K. Tsuda et al. "An Aromatization Reaction of a Cross–Conjugated Dienone System with Zinc", 26, p. 2614, 1961.

K.M. Smith et al., "Electrophilic Mercuration Reactions of Derivatives of Deuteroporphyrin IX: New Syntheses of Coproporphyrins III, Harderoporphyrin", J. Org. Chem., 48, p. 500, 1983.

P.S. Clezy, et al., "Chemistry of Pyrrolic Compounds XXVII Some Aspects of the Mass Spectra and Chemistry of meso-Substituted Porphyrins", Aust. J. Chem., 27, p. 1003, 1974.

R. B. Woodward et al., "The Total Synthesis of Chlorophyll", J. Am. Chem. Soc., 82, p. 3800, 1960.

R. Bonnet et al., "Hydroporphyrins of the Meso–tetra (hydroxyphenyl) Porphyrin Series as Tumour Photosensitizers", Biochemical Journal, 261, p. 277, 1989.

R. Bonnet "Photosensitizers of the Porphyrin and Phthalocyanine Series for Photodynamic Therapy", Chem. Soc. Rev., 1995, p. 19.

R. Bonnett et al. "The meso Reactivity of Porphyrins and Related Compounds I. Nitration", J. Org. Chem., 30, p. 2791, 1965.

W.P. Griffith, et al. "Preparation and Use of Tetra–n–butylammonium Per–ruthenate (TBAP reagent) and Tetra–npropylammonium Per–ruthenate (TPAP reagent) . . . ", J. Chem. Soc. Chem. Commun. p. 1625, 1987.

Formation of octaethylbenzochlorin (17)

Vinylogous Vilsmeier reaction of metallated octaethylporphyrin (M-4)

A possible synthesis of the α-imino precursor (92)

Expected product from the cyclization of (92)

Synthesis of purpurins

Panel A

Type A Purpurin   Type B Purpurin

Panel B

Synthesis of the australochlorins

Aromatization of the steroid A ring using zinc

Panel A

Postulated mechanism for the removal of the angular ethyl group of (93)

Panel B

Possible cyclization of the glycolaldehyde condensation product (96)

(98)

(99)

Methylcarbamate condensation with (56) and subsequent cyclization

Proposed route to *meso*-aminomethyloctaethylporphyrin (104)

Proposed use of (105) as a cyclization intermediate

Synthesis of (106)

The side-product from N-hydroxymethylation of (Ni-105)

Proposed cyclization of the N-formylamide (109)

Synthesis of *meso*-isocyanooctaethylporphyrin (112)

Passerini reaction of (112)

Acid-catalyzed reaction of (112) with formaldehyde to give (116)

Rationale for the cyclization/lack of cyclization of the two types of hydroxymethylamide (106) and (116)

Possible mechanism for the formation of the dimer (Ni-119)

Mechanism for the formation of the dimer (Ni-120)

SYNTHESIS OF LONG WAVELENGTH ABSORBING PHOTOSENSITIZERS

The present United States patent application claims priority under 35 USC section 119 of Canadian patent application 2,221,912 of Johnson et al., filed Nov. 21, 1997, and entitled "Photosensitizers with Improved Biodistribution and Light-Absorbing Properties". The Canadian application, including the complete text and figures thereof, is incorporated by reference herein, as if fully set forth.

FIELD OF THE INVENTION

The present invention provides for novel therapeutic macrocycle compounds useful in photodynamic therapy that are based on the chlorin ring system. The macrocycle compounds have absorption spectra optimized for therapeutic use in tissues, and are stabilized against oxidation by the attachment to the chlorin ring of a structure that comprises one or more exocyclic rings that also contribute at least one nitrogen atom. Protonation or covalent modification of this nitrogen atom, or other covalent modification of the one or more exocyclic rings, permits optimization of pharmacologically relevant properties including, for example, solubility. Representative of such chlorins are the "pyridochlorins" depicted as follows.

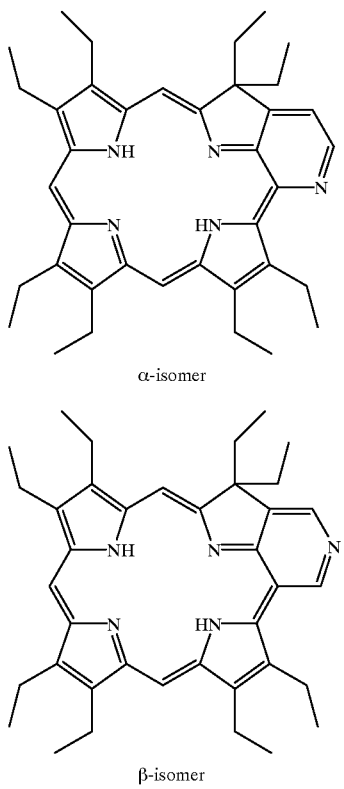

α-isomer

β-isomer

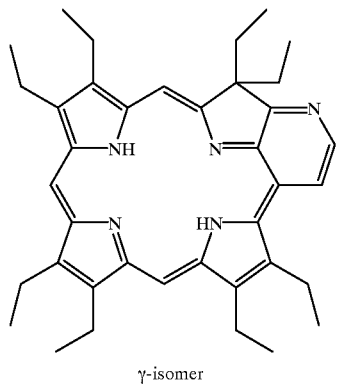

γ-isomer

BACKGROUND OF THE INVENTION

Photodynamic therapy ("PDT") generally involves administration of a drug (photosensitizer) which, when irradiated with light, becomes electronically activated such that it may interact with molecular oxygen to generate reactive oxygen species. The reactive oxygen species are believed responsible for killing of targeted cells, which are generally those associated with an unwanted hyperproliferating state.

Unless a photosensitizer compound is to be used solely for the treatment of superficial skin diseases, it is important that the wavelength(s) at which the compound absorb light be optimized. Preferably, the compound should absorb strongly in the red region of the spectrum (650–800 nm). Light scattering and the presence of endogenous chromophores (such as hemoglobin) results in very poor penetration of tissues by light at wavelengths below about 600 nm. This means that the large absorption band (the so called Soret band) displayed by porphyrins in the region of 400 nm is not available, practically speaking, for photosensitizer activation in PDT.

Instead, the longer wavelength Q absorption bands must be used. However, the longest wavelength Q band for Photofrin® (see U.S. Pat. No. 5,059,619), a first generation porphyrin photosensitizer, is only at about 630 nm. Although this wavelength is long enough to permit useful photodynamic therapy approaches for some tumors, it is not ideal. Since light penetration of human tissues typically doubles between 630 and 750 nm, a photosensitizer absorbing at 750 nm would be far more effective at treating thick tumors than, for example, Photofrin®. However, increasing the absorption wavelength of photosensitizer compounds beyond about 800 nm (into the infrared), would not give rise to further improvements, since the involved energy transitions are insufficient to generate a sufficiently energetic excited state, and corresponding activated oxygen species.

Accordingly, there is a considerable medical need to develop classes of photosensitizers having optimized light absorption properties. One such improved class of photosensitizers are the so called "green monohydrobenzoporphyrins" which are derived from natural porphyrins by Diels-Alder type reactions at one of the functional groups attached to the porphyrin core. An example of such a compound, which is currently in phase III clinical trials, is BPDMA which shows considerable absorption at about 688 nm. In this regard, see for example, U.S. Pat. Nos. 5,095,030; 5,171,749; 5,776,966 and the like. Finally, the porphyrin core structure is characteristically non-polar, and such structures need to be modified by the addition of groups having sufficient polarity to improve the solubility and amphiphilicity properties of the compound, and to improve the rate of metabolism or clearance in the body.

The core structure known itself as porphyrin, as mentioned above, is presented below in comparison with that of chlorin. In principle, the simplest way to increase the wavelength of absorption of a porphyrin would be by reduction of a double bond therein to give the corresponding chlorin (reduction of a porphyrin to a chlorin results in an increase in both the intensity and wavelength of the longest absorption band—providing a shift of about 25 nm and typically a substantial increase in extinction coefficient).

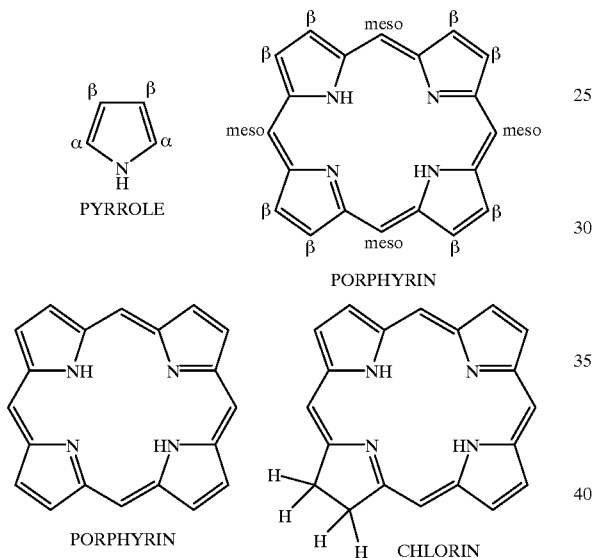

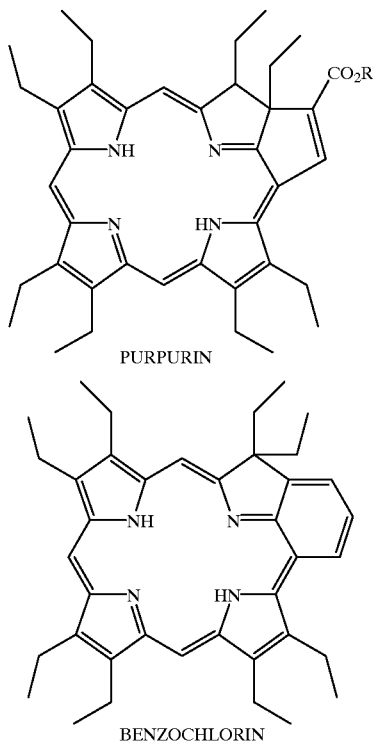

Although reducing agents such as diimide are available that will regioselectively reduce only the double bond targeted for simply conversion of a porphyrin to a chlorin, such reactions are typically reversible. Oxygen in the air is well known to oxidize chlorins back to porphyrins and this impacts not only the synthesis, but also the storage and clinical use of the resultant compound. Accordingly, there are only a limited number of cases where such procedures have been used to synthesize chlorins (see for example R. Bonnet, Chem. Soc. Rev., 1995, p. 19, and R. Bonnet et al., Biochemical Journal, 261, p. 277, 1989, in relation, for example, to the synthesis of tetrakis (m-hydroxyphenyl) chlorin, "m-THPC").

Examples of known chlorins that contain unsaturated exocyclic rings fused to the skeleton between a meso position and its adjacent β-position include purpurins and benzochlorins. Fusion of such exocyclic rings has the advantage of substantially limiting oxidation of the prepared chlorin at the previously reduced pyrrole ring.

A number of purpurins have been described. See, for example, R. B. Woodward et al., J. Am. Chem. Soc., 82, p. 3800, 1960, and also J. H. Fuhrhop et al., Angew. Chem. Int. Ed. Engl., 14, p. 361, 1975 describing an octaethyl purpurin which absorbs at 695 um. A number of purpurins have been shown to have photodynamic activity, and the most effective member of this class of compounds may be a tin etiopurpurin formed by cyclization of meso-[β-(2-ethoxycarbonyl) vinyl] etioporphyrin, followed by metallation with tin chloride. This compound is currently in clinical trials (A. R. Morgan et al., Photochem. Photobiol., 51, p. 589, 1990; A. R. Morgan et al., J. Med. Chem., 32, p. 904, 1989).

The synthesis of a benzochlorin was first described by D.P. Arnold et al. J.C.S. Perkin I, p.1660, 1978, and sulfonation of a benzo ring thereof was effected in concentrated sulfuric acid (see A. R. Morgan et al., Photochem. Photobiol. 55, p.133, 1992 and B. C. Robinson et al., SPIE Optical Methods for Tumor Treatment and Detection: Mechanisms and Techniques in Photodynamic Therapy V, 2675, p. 179, 1996). The resulting sulfonic acid group can be used as a platform for further derivatization, such as to modify bioactivity. An additional pathway to effect derivatization of a benzochlorin involves reaction of a metallated benzochlorin at the meso position adjacent to a gem-diethyl group to yield an iminium salt (D. Skalkos et al., Photochem. Photobiol., 59, p. 175 1994). Photodynamic activity has been demonstrated for various benzochlorins (see A. R. Morgan et al., Photochem. Photobiol. 55, p.133, 1992, and A. R. Morgan et al., Tetrahedron Letters, 35, p. 5347, 1994).

The preparation of a pyridinoporphyrin has been described, C. Alonso et al., Tetrahedron Letters, 38(15), pp. 2757–2758, 1997 wherein the pyrindinyl nitrogen atom, or the pyridinyl ring, may serve as a platform for further derivatization. However, such a compound is believed to lack the optimized absorption profile characteristic of the pharmaceutically useful chlorins.

As aforementioned, the presence of an exocyclic ring fused to the core structure of a chlorin at the site of the reduced pyrrole ring substantially prevents re-oxidation thereof. It would be further advantageous to derivatize the exocyclic ring to optimize biological properties such as solubility, physiological clearance, or to enhance amphiphilicity, that is the presence of both polar and non-polar domains thus enhancing interaction with both polar and non-polar environments. Although derivatization has been described, for example, for benzochlorin by sulfonation under strongly acidic conditions, there is a clear need to develope more flexible methods whereby a large number of such pharmaceutically useful chlorins can be prepared. As described below, the present invention provides such methodology and resultant compounds.

SUMMARY OF THE INVENTION

The present invention provides for novel therapeutic macrocycle compounds useful in photodynamic therapy that are based on the chlorin ring system. The macrocycle compounds are stabilized against oxidation by the attachment to the chlorin ring of a structure that comprises one or more exocyclic rings that contribute at least one nitrogen atom. Protonation or covalent modification of this nitrogen atom, or other covalent modification of the one or more exocyclic rings (hereinafter "derivatization") permits optimization of pharmacologically relevant properties including, for example, solubility. Optionally, the chlorin ring is metallated.

In a preferred embodiment of the invention, compounds are represented by the formula (1)

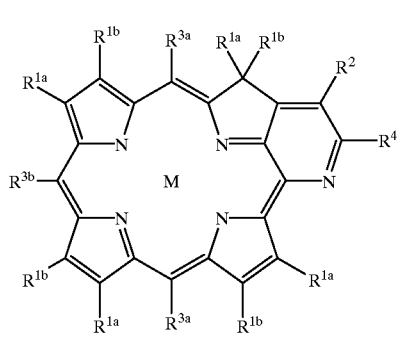

(1)

wherein, for example, $R^{1a}$, $R^{1b}$ are independently H or alkyl;

$R^2$ is OH, halogen, alkoxy, OCO-alkyl, sulfonate, sulfate, or phosphate;

$R^{3a}$ is H, or a phenyl or other aryl or heteroaryl group optionally substituted by one or more groups, each independently selected, for example, from halogen, hydroxy, alkyl, alkoxy, cyano, and ester;

$R^{3b}$ is H, halogen, formyl, nitro, amino or cyano $R^4$ is H or alkyl;

M is a complexing metal, typically known in the art, or represents 2H; and

N, the nitrogen atom of the pyridine ring, is optionally in the form of an N-oxide, or a salt such as an alkyl or hydrogen halide.

In a further preferred embodiment of the invention, compounds are represented by the formula (2)

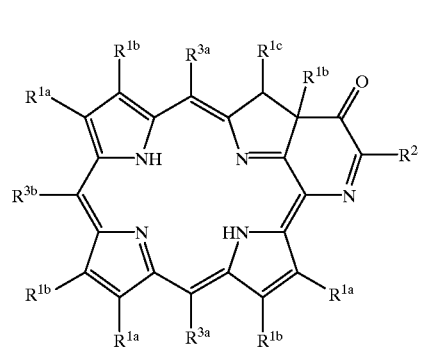

(2)

wherein the substituents are generally as for compound (1) although certain preferences or exceptions are described as follows:

$R^{1a}$ is not H, and is preferably methyl or ethyl, in which case $R^{1c}$ (formed from an $R^{1a}$) would be $CH_3CH=$ or $CH2=$;

$R^{1b}$ is as for compound (1);

$R^2$ is H or alkyl (and fixed at the position alpha to the N atom);

$R^{3a}$ is as for compound (1);

$R^{3b}$ is as for compound (1);

The C=O group may, optionally, be converted to a CHOH group, and the resultant OH group may be further derivatized, such as via the $R^2$ options described for compound (1);

It should be noted that since the exocyclic ring is not aromatic (comparing to compound 1), the N-oxide or salt variations are inapplicable, although compound (2) can exist as a free base or a metal complex.

In an additional embodiment of the invention, compounds are represented by the formula (3)

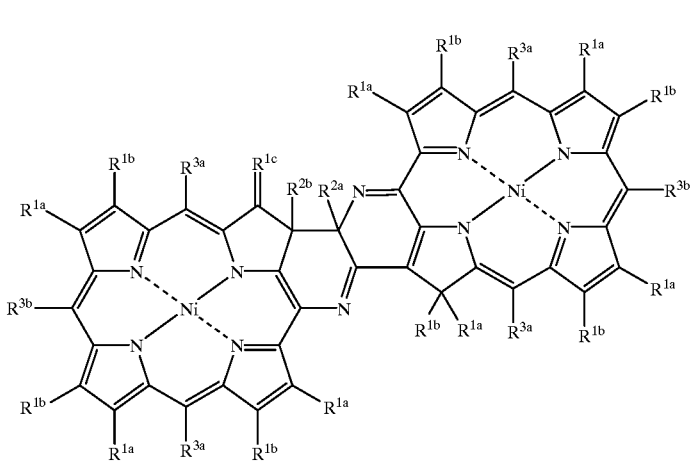

(3)

wherein, preferably, $R^{1a}$ would be methyl or ethyl;

$R^{1b}$ would be as for compound (1);

$R^{3a}$ would be as for compound (1);

$R^{3b}$ would be as for compound (1); and either $R^{1c}$, together with the carbon atom to which it is bonded, forms a $C(R^{1a})(R^{1b})$ group and $R^{2a}$ and $R^{2b}$ together form a bond; or $R^{1c}$ is $CH_3CH$ or $CH_2$;

$R^{2a}$ is H; and $R^{2b}$ is $R^{1b}$.

With respect to the design of such compounds(3), the N-oxide or salts mentioned for compound (1) are also within the practice of the invention, and compound (3) can also exist in free base or as a dimetal complex.

As aforementioned, more than one exocyclic ring may be present in the compounds of the invention, there being generally no structural limitation on any such combination of rings subject of course to practical considerations of synthesis, and that one or more suitable nitrogen atoms be appropriately placed therein. Accordingly, additional representative compounds of the invention include:

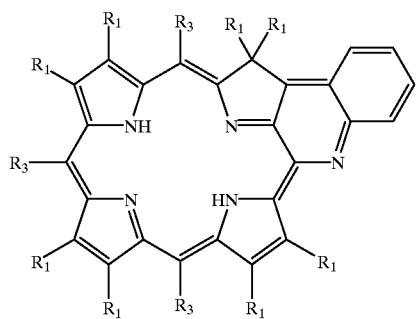

-continued

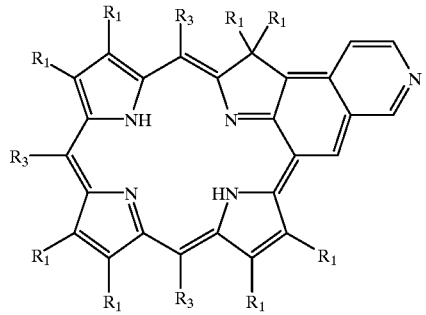

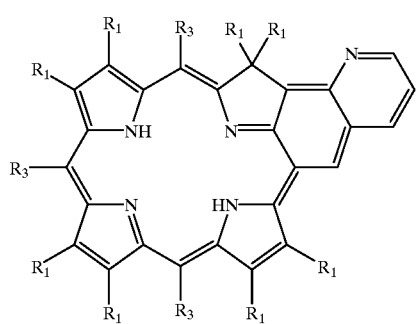

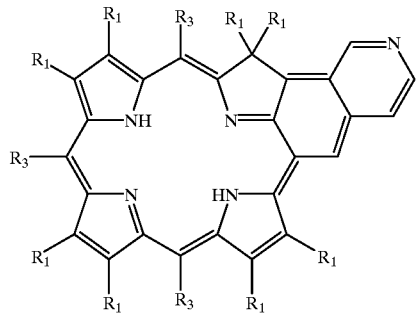

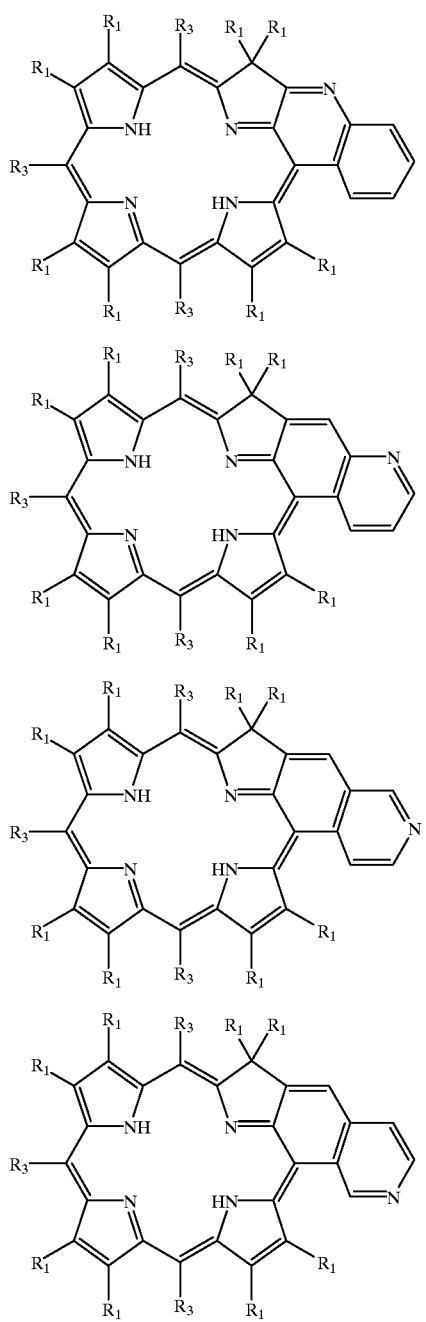

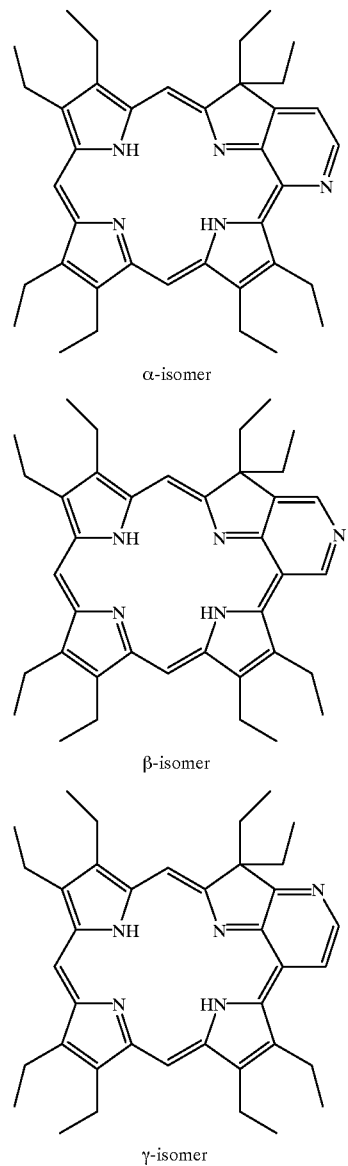

α-isomer

β-isomer

γ-isomer and the like, where it is additionally understood that more than one nitrogen atom may be present in the exocylic rings, which may be fuirther substituted by other functional groups (such as hydroxyl or keto) and which permit further enhancements in desireable properties such as solubility.

Additional preferred compounds include the "pyridochlorins" such as:

Additional preferred examples of the invention include:

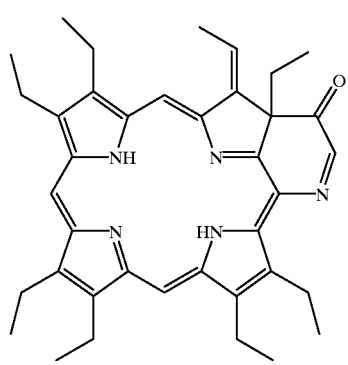

-continued

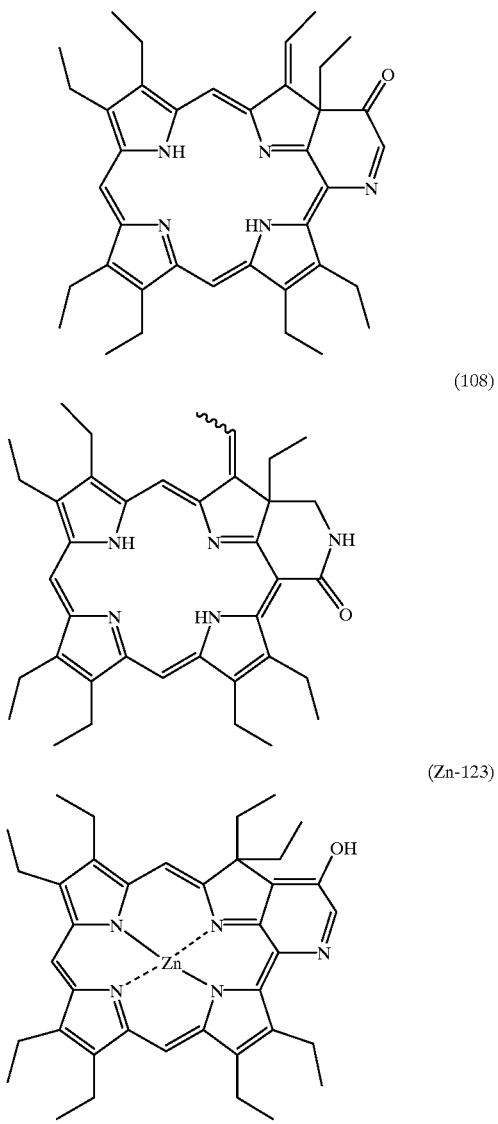

(108)

(Zn-123)

DETAILED DESCRIPTION OF THE INVENTION

Figure 1:
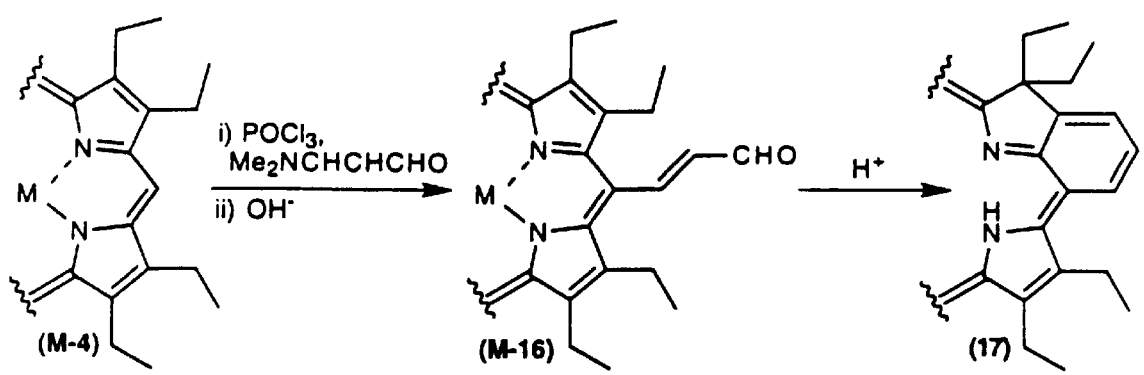
FIG. 1 depicts a synthesis of octethylbenzochlorin

The present invention provides for novel therapeutic macrocycle compounds useful in photodynamic therapy that are based on the chlorin ring system. The macrocycle compounds of the invention have relatively long wavelengths of absorption, to permit penetration of tissues, such as about 670 nm, although this may vary with the particular compound based upon its exact cyclic structure and ring substituents.

The compounds are stabilized against oxidations, such as at the reduced ring of the chlorin (which would cause the molecule to revert to a porphyrin structure), by the presence of one or more exocyclic rings in contact with the reduced pyrrole ring. In a typical embodiment, the exocyclic ring or rings are aromatic, although they may also be non-aromatic or have partial aromatic character. Most preferably the exocyclic ring or rings comprise at least one nitrogen atom, or comprise at least one substituted carbon atom, or a carbon atom which is subject to substitution. As a result of this modification to the exocyclic ring(s), and/or further derivatization at such sites, physiologically relevant properties of the compound can be improved, such as improved solubility, amphiphilicity, drug clearance, and the like.

Accordingly, there are provided compounds according to the structures

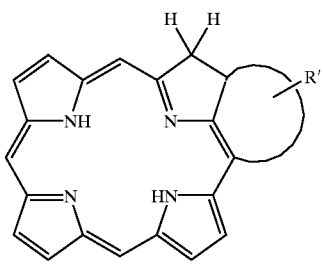

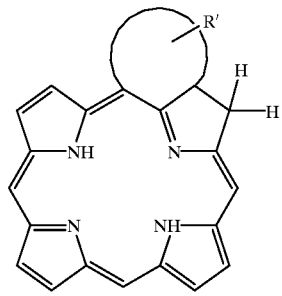

wherein the circle represents an exocyclic structure having one to about three rings and preferably at least one nitrogen atom which can be protonated or further substituted. R' represents one or more substituents in the ring structure which may be selected (see below) to further enhance or modify the compound's properties. As depicted directly above, the exocyclic structure can be positioned on either side of the reduced pyrrole ring of the chlorin. Such positions could be considered as symmetrical, except for the asymmetries introduced into the compounds by the other substituents (see also below).

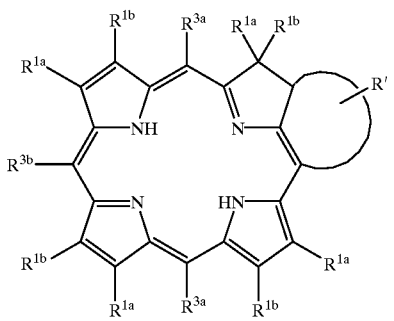

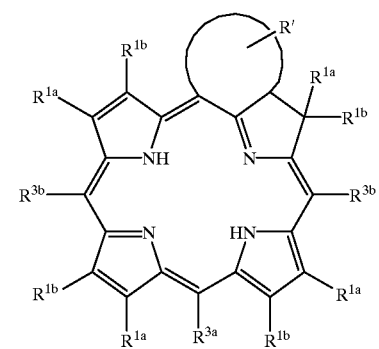

Most preferably, the exocyclic structure contains from one to about three rings, and from about 5 to about 25 carbon atoms, wherein preferably at least some of the carbon atoms are involved in double bonds. It is particularly preferred that the exocyclic structure contain one or more ring nitrogen atoms which, typically, in derivatized or protonated form, can be used to enhance the solubility in aqueous systems of the macrocycle. The exocyclic structure is subject to further modification by from one to many groups R', which similarly to the other R groups attached to the chlorin ring itself, may be used to modify the properties of the macrocycle. Options for selection of groups R' are generally the same as for other R groups present in the structure, although there would be exceptions as is readily understood in the art.

Accordingly, representative exocyclic structures useful in the practice of the invention include those depicted below:

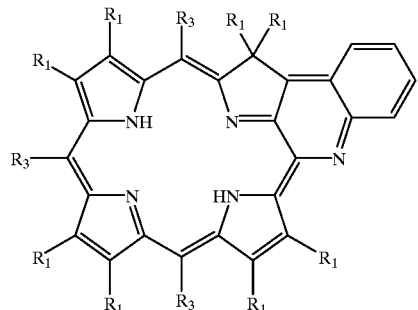

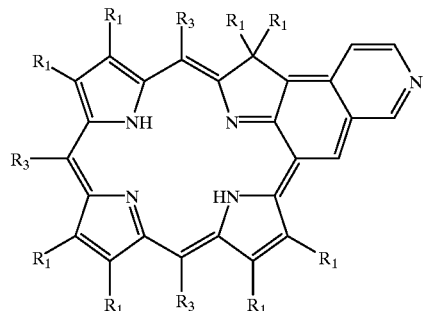

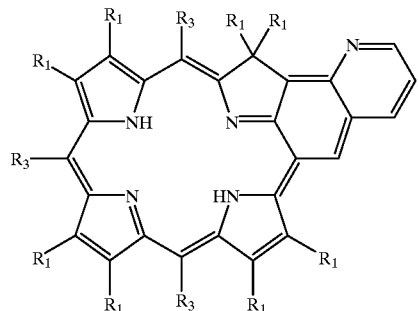

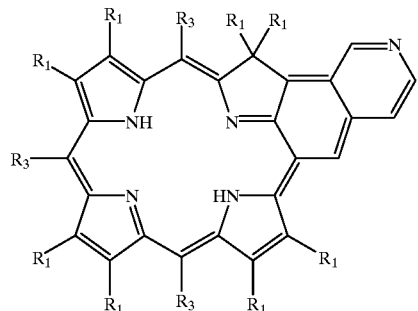

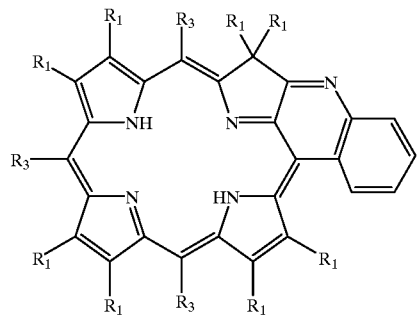

-continued

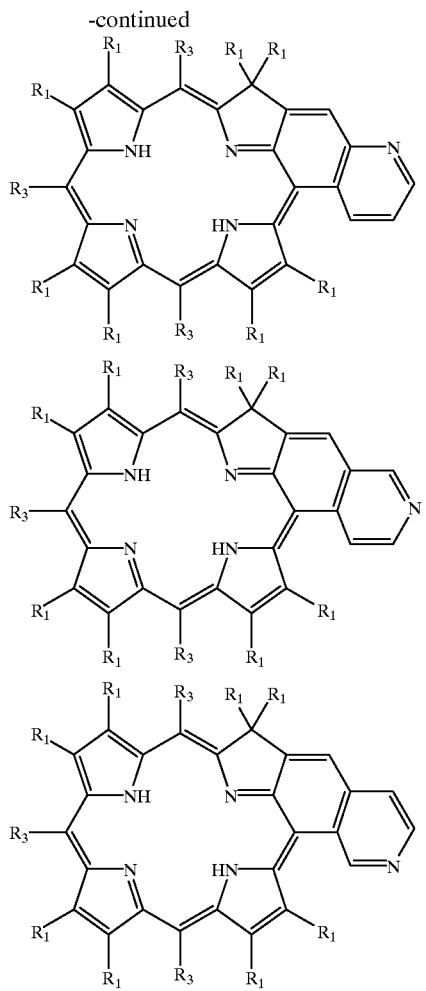

In a preferred embodiment of the invention, compounds are represented by the formula (1)

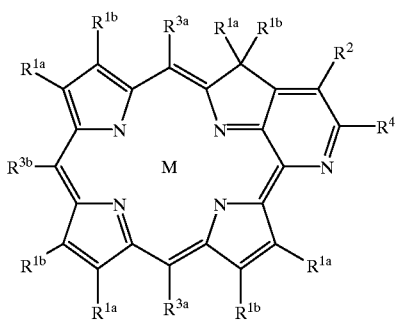

wherein, for example, $R^{1a}$, $R^{1b}$ are independently H or alkyl;

$R^2$ is OH, halogen, alkoxy, OCO-alkyl, sulfonate, sulfate, or phosphate;

$R^{3a}$ is H, or a phenyl or other aryl or heteroaryl group optionally substituted by one or more groups, each independently selected, for example, from halogen, hydroxy, alkyl, alkoxy, cyano, and ester;

$R^{3b}$ is H, halogen, formyl, nitro, amino or cyano;

$R^4$ is H or alkyl;

M is a porphyrin-complexing metal, typically known in the art, or represents 2H; and N, the nitrogen atom of the pyridine ring, is optionally in the form of an N-oxide, or a salt such as an alkyl or hydrogen halide.

It will be appreciated that the exact position of the nitrogen atom in the exocyclic structure is subject to considerable variation, limited of course by available routes of synthesis, and thus numerous other compounds are preferred according to the practice of the invention. Representative compounds include

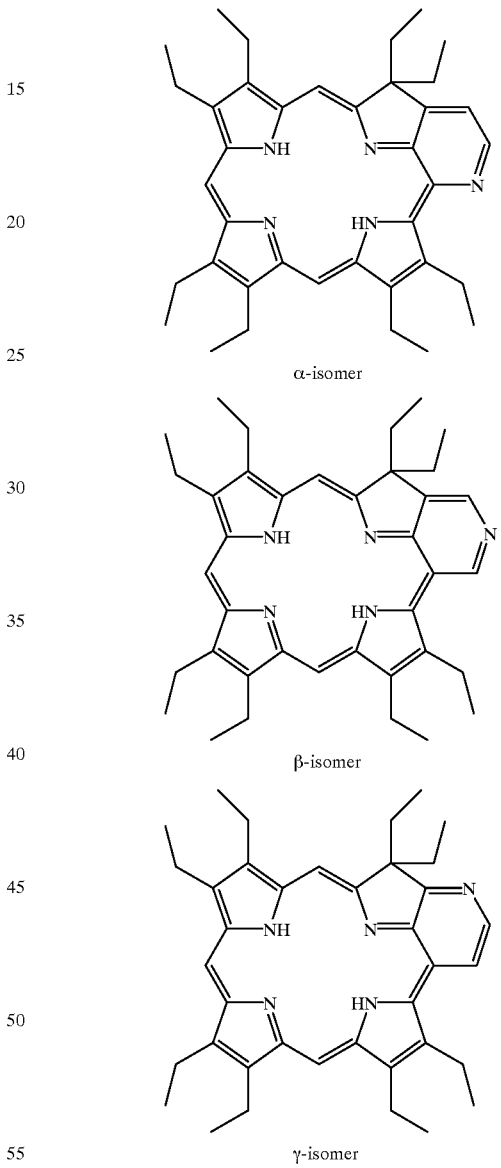

In connection with the design of such compounds, additional substituents may be used as long as they do not interfere with the intended therapeutic activity, or capacity of the compound to be formulated for use. As will be appreciated by those skilled in the art, additional derivatizing groups may be used, such as other charged or polar groups, to affect, for example, compound solubility, the range of such substituents being limited of course, by the feasability of available synthesis routes.

The addition of further functional groups to the exocyclic structure provides additional opportunities for derivatization and fine tuning of pharmacologically relevant properties. In a further preferred embodiment of the invention, compounds are represented by the formula (2).

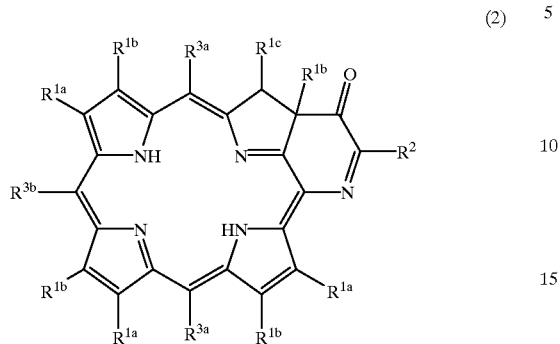

(2)

wherein the substituents are generally as for compound (1) although certain preferences or exceptions are described as follows:

- $R^{1a}$ is not H, and is preferably methyl or ethyl, in which case $R^{1c}$ (formed from an $R^{1a}$) would be $CH_3CH=$ or $CH2=$;
- $R^{1b}$ is as for compound (1);
- $R^2$ is H or alkyl (and fixed at the position alpha to the N atom);
- $R^{3a}$ is as for compound (1);
- $R^{3b}$ is as for compound (1);
- The C=O group may, optionally, be converted to a CHOH group, and the resultant OH group may be further derivatized, such as via the $R^2$ options described for compound (1).

It should be noted that since the depicted exocyclic ring is not aromatic (comparing to compound 1), the N-oxide or salt variations are inapplicable, although compound (2) can exist as a free base or a metal complex.

As aforementioned, the exact position of the nitrogen atom and any further functional groups in the exocyclic structure can be varied considerably. Accordingly, representative related compounds of the invention include

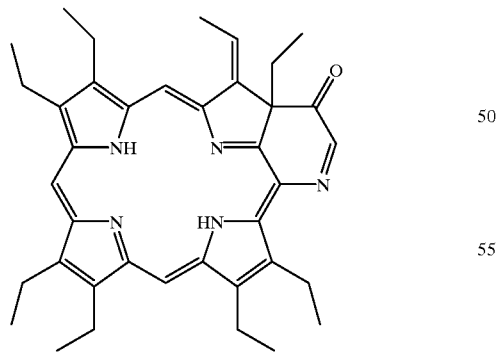

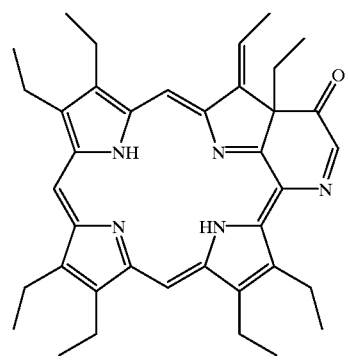

(108)

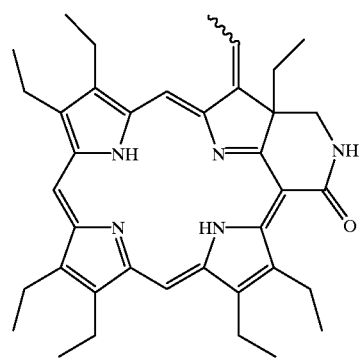

(Zn-123)

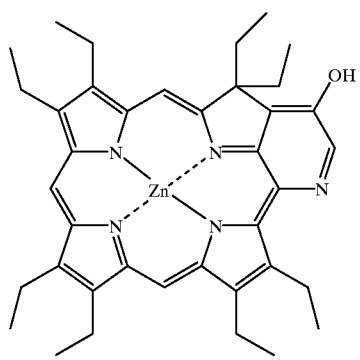

In an additional embodiment of the invention, compounds are represented by the formula (3)

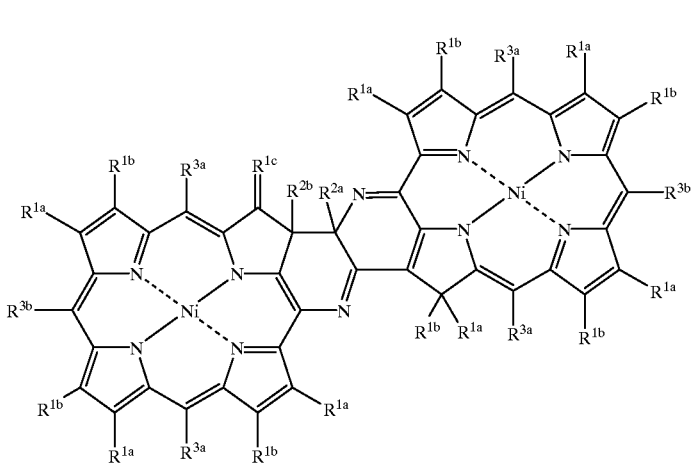

(3)

wherein, preferably, $R^{1a}$ would be methyl or ethyl;

$R^{1b}$ would be as for compound (1);

$R^{3a}$ would be as for compound (1);

$R^{3b}$ would be as for compound (1); and either $R^{1c}$, together with the carbon atom to which it is bonded, forms a $C(R^{1a})(R^{1b})$ group and $R^{2a}$ and $R^{2b}$ together form a bond; or $R^{1c}$ is $CH_3CH$ or $CH_2$;

$R^{2a}$ is H; and $R^{2b}$ is $R^{1b}$.

With respect to the design of such compounds(3), the N-oxide or salts mentioned for compound (1) are also within the practice of the invention, and compound (3) can also exist in free base or as a dimetal complex.

It is again noted that generally the compounds of the present invention can exist in a metallated form, or the metal atom of the chlorin ring(s) can be replaced by 2H, as would be readily apparent to those skilled in the art.

Pharmaceutical Administration

The compounds of the invention may be formulated in a variety of ways for pharmaceutical use. Generally speaking, such formulations include any excipients, stabilizers, emulsifying agents, osmotic agents, solubilizing agents and the like, that are recognized as useful to deliver photosensitizer compounds to the body whether topically or internally in any way such as by intravenous, intraperitoneal, or intramuscular injection, transmucosally, orally, transdermally by way of skin patches, salves and gels, and such. Liposomal formulations, as recognized in the art, represent a preferred form of formulation, including formulations with phosphatidyl serine, phosphatidyl glycerol, phosphatidyl choline, and the like. Additionally, it will be recognized that functional groups are typically added to the macrocycles of the present invention to facilitate their storage, preparation, solubility, and physiological utility.

Generally, reference may be made to Remington's Pharmaceutical Sciences, Mack Publishing Company, Easton, Pa., latest addition. Additional information concerning generally acceptable formulations is provided in U.S. Pat. Nos. 5,095,030; 5,171,749; 5,776,966; 5,789,433; 4,512, 762; 4,566,636; 5,399,583; 4,920,143, pertaining to photosensitizers for pharmaceutical use. The compounds of the invention may generally be used for all of the therapeutic applications for which photosensitizer compounds have been recognized, as mentioned for example in the cited patents. As is recognized by medical practitioners, dosages vary considerably based on the mode of administration, formulation, condition of the patient, condition to be treated, and the like. For systemic administration, dosages on the order of 10 microgram/kg to 100 mg/kg, preferably 100 microgram/kg to 10 mg//kg may be preferred. With respect to topical administrations, suitable compositions may range from about 1 to 10% of the composition, or greater or lesser, depending upon the application, as would be recognized in the art.

EXAMPLES

Synthesis Routes for Pyridochlorins

Although octaethylbenzochlorin (Arnold et al., 1978) proved resistant to many kinds of derivatization reactions, its overall photochemical properties and stability suggested the desireability of synthesizing novel macrocylces that incorporated some of its features. By substituting an exocyclic pyridine ring for an exocyclic benzene ring, a compound would be provided that would permit nucleophilic substitution reactions on the exocyclic pyridine ring, in contrast to mostly unsuccessful electrophilic substitutions attempted on the benzochlorin benzene ring. Representative of such "pyridochlorins" are the α-, β-, and γ-isomers of "octaethylpyridochlorin", as depicted below.

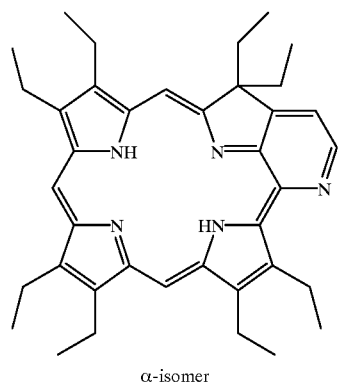

α-isomer

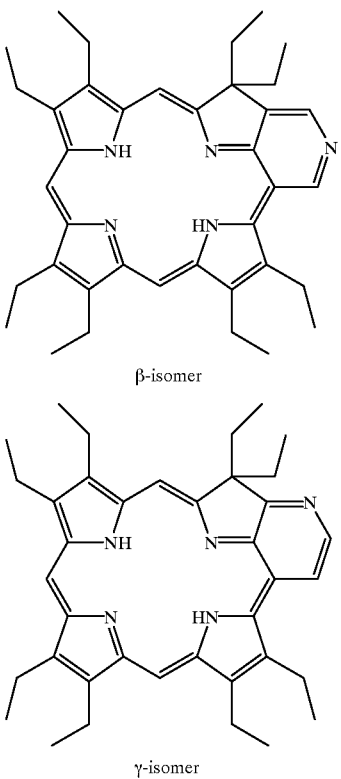

β-isomer

γ-isomer

For demonstration purposes, an evaluation was made as to which of the three isomers was likely to be the most easily synthesized. Here a comparison with the synthesis of octa-ethylbenzochlorin was made The formation of the latter is achieved by a vinylogous Vilsmeier reaction on metallated octaethylporphyrin to give the acrolein-substituted metalloporphyrin (M-16 in FIG. 1, Formation of Octaethylbenzochlorin).

If a similar method were to be used for the synthesis of pyridochlorins, it would seem logical first to make the nitrogen analogues of the meso-acrolein. This reaction pathway would rule out the synthesis of the γ-pyridochlorin as this would require nucleophilic attack by the β—β double bond on the nitrogen atom, a highly unlikely reaction. For this reason, efforts were concentrated on synthesizing the α- and β-pyridochlorins.

Example 1

The design and synthesis of α-pyridochlorin

Figure 2:
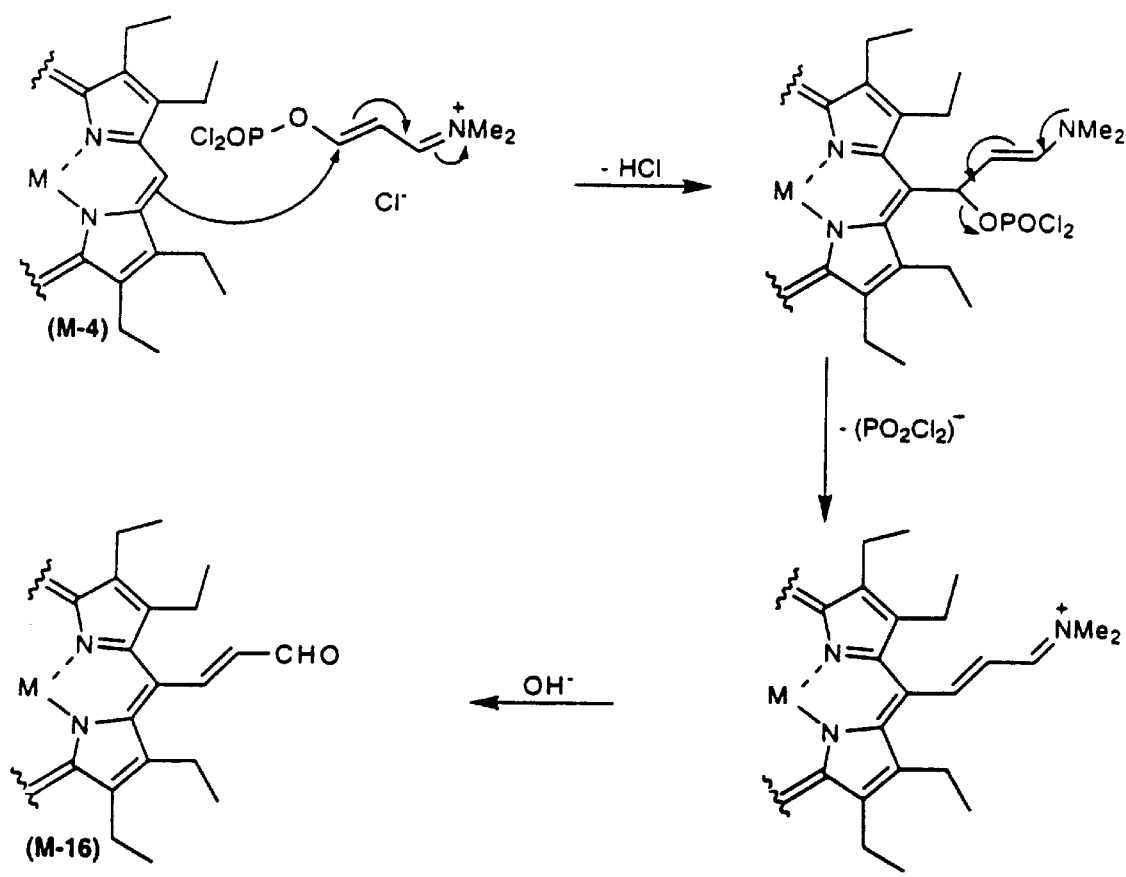
FIG. 2 depicts a vinylogous Vilsmeier reaction of metalled octaethylporphyrin

In order to synthesize the a-pyridochlorin it was necessary first to make (92), the a-imino analogue of the acrolein derivative (16) used in the benzochlorin synthesis (FIG. 1). (M-16, "M" meaning metallated) is formed in two steps by electrophilic attack on the porphyrin meso-carbon by the vinylogous Vilsmeier reagent formed from 3-(dimethylamino) acrolein and phosphoryl chloride, followed by treatment with aqueous base to hydrolyze the iminium salt to the aldehyde (FIG. 2).

Figure 3:
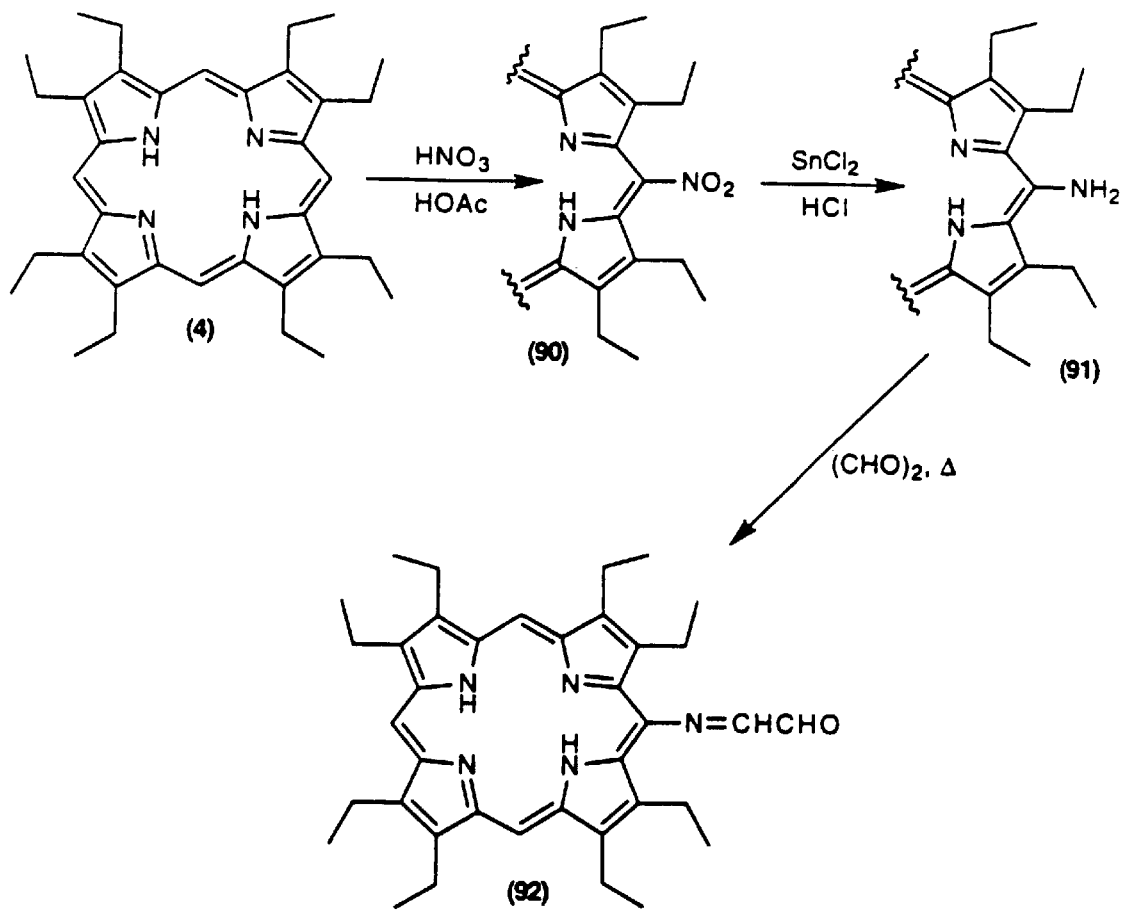
FIG. 3 depicts a possible synthesis of the α-imino precursor, species (92).

Clearly, another approach was necessary to create the α-nitrogen analog. One well-known method of obtaining a porphyrin meso-substituted by a nitrogen functionality is nitration. The nitro compound can be reduced to the aminoporphyrin, and such compounds are reported to react with aldehydes to give Schiff's bases (A. W Johnson et al., *J. Chem. Soc.* (*C*), p. 794, 1966). Thus a reasonable route to the desired precursor from octaethylporphyrin would be to prepare the nitro derivative (90), reduce it, and then form the Schiff s base with glyoxal (FIG. 3).

The nitration was carried out in an ice-cold mixture of glacial acetic acid and concentrated nitric acid to give the mono-nitro compound (90) in 50% yield. The reaction mixture had to be monitored carefully, in order to minimize the formation of poly-nitro compounds. The reduction of the nitro group to the amine was effected with stannous chloride dihydrate in concentrated hydrochloric acid and gave the desired product (91) in 85% yield. Thus far, the synthesis proceeded as described in the literature. (A. W. Johnson et al., *J. Chem. Soc.* (*C*), p. 794, 1966; R. Bonnett et al., *J. Org. Chem.*, 30, p. 2791, 1965; A. W. Johnson et al., *J. Chem. Soc.* p. 4303, 1965).

The formation of Schiff s bases by condensing aminoetioporphyrin with benzaldehyde and anisaldehyde has been described as occurring in good yield (>80%). However, these reactions were performed using the aldehyde as solvent, while glyoxal trimer dihydrate (the aldehyde necessary for this synthesis) is a solid. Hence a solvent system in which both the aldehyde and the porphyrin would have reasonable solubility was required. A number of small-scale experiments lead to the finding that a mixture of ethanol and THF was a suitable solvent, the ethanol dissolving the glyoxal trimer when heated, and the THF dissolving the porphyrin. Although the condensations reported with benzaldehyde and anisaldehyde occurred at room temperature, it was necessary to reflux the glyoxal/porphyrin mixture overnight. This might well be accounted for by the lower concentrations of reagents resulting from the use of a solvent. The optimized yield of the reaction was 69%, or 80% based on recovered starting material. Unsuccessfull attempts were made to drive the reaction to completion by the addition of drying agents, but it is likely that the amount of residual water in the THF/ethanol solvent far outweighed the small quantity of water produced in the condensation. In any case, the product (92) could be separated from the polar starting material by column chromatography, and the latter could then be reused. Before attempting this condensation, it had been anticipated that dimer formation, resulting from the reaction of an aminoporphyrin with each of the two formyl groups of glyoxal, might occur. However, the use of a large excess of glyoxal prevented the dimeric product from being formed in any significant quantity.

(92) was stable enough to allow it to be chromatographed on silica, although care was taken to elute it from the column as quickly as possible as some decomposition to the amine was observed during chromatography. However, as it appeared to be sensitive to acid, and the cyclization step was expected to require the use of such conditions, problems with this step of the synthesis were envisaged. Consequently, attempts were made to reduce the imine functionality to the amine using sodium cyanoborohydride, a reagent reported to reduce imines selectively in the presence of carbonyl groups. Unfortunately, any products formed in this reaction appeared to be very unstable, and decomposed during work-up to give the amine (91). In view of this result, the cyclization reaction was performed directly on (92), in the hope that conditions favoring cyclization over hydrolysis could be developed.

In an effort to minimize the possibility of hydrolysis, initial experiments employed nonacidic conditions, namely refluxing in toluene. Indications that neutral, high temperature conditions might be successful came during a synthesis of the imine, when the solvent inadvertently was allowed to boil away, and the reaction mixture was heated as a solid for several hours. On working up this product, no trace of the desired imine (92) was present; instead, in addition to the amine starting material (91), which was the major compound isolated, a few milligrams of a mixture of two low polarity green compounds (93) was obtained. By $^1$H NMR and visible spectroscopy these compounds appeared to be two isomers with a chlorin structure.

Despite the very close analogy to the octaethylbenzochlorin synthesis, the replacement of a CH group with a nitrogen atom obviously changes the cyclization mechanism significantly, even though the N atom is several bonds removed from the site of reaction. There appears to be a closer similarity to purpurin synthesis. These compounds are

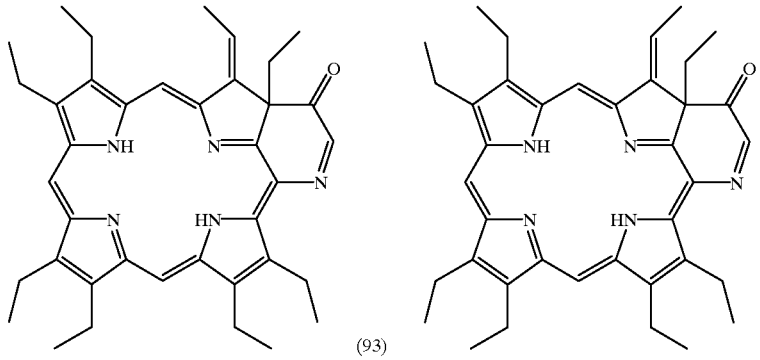

(93)

On refluxing the imine in toluene overnight this result was reproduced, the isomeric mixture (93) being formed in 15% yield. No starting material was recovered, but a substantial quantity of the amine (91) was isolated; it seems that the cyclization and hydrolysis reactions are in competition with one another, which would suggest that obtaining the cyclized product in high yield might not be possible.

Although the quantity of cyclic product (93) thus far obtained was small, and it consisted of a mixture of two isomers, it was relatively simple to determine the structure using spectroscopic techniques: firstly, the visible spectrum showed an absorption peak at 722 nm (∈=10800), indicative of a reduced porphyrin species such as a chlorin (the longest-wavelength absorption of the precursor imine was at 660 nm and very weak (∈=4400)). Secondly, in the 40.0 MHz $^1$H NMR spectrum there were some very distinctive peaks: two quartets at 7.45 ppm and 7.72 ppm and two doublets at 2.62 ppm and 2.81 ppm. These resonances are typical of the ethylidene functionality CHCH$_3$ attached via a double bond to the β-position of a reduced pyrrole ring. There were also two singlets at 7.98 ppm and 8.15 ppm, in addition to the expected meso-hydrogen signals, and these could be assigned to the imino CH of the two isomers. Finally there were two triplets at 0.10 ppm and 0.50 ppm, suggesting the presence of ethyl groups lying out of the plane of the macrocycle and hence experiencing a greater degree of shielding by the ring current than those lying in the plane. The two isomers (93) were present in a ratio of approximately 4 to 1. This information lead to the two isomers (93) being assigned the structures shown above.

Figure 4:
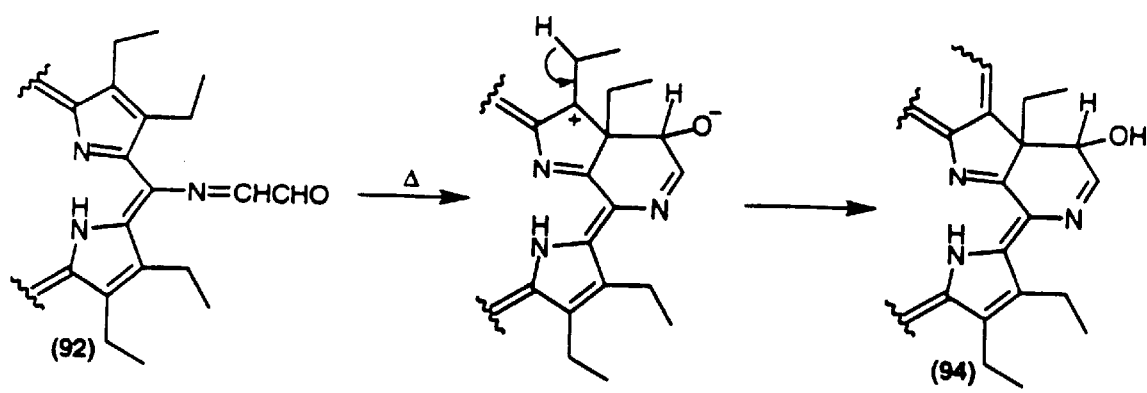
FIG. 4 depicts the product expected from the cyclization of species (92).
Figure 5:
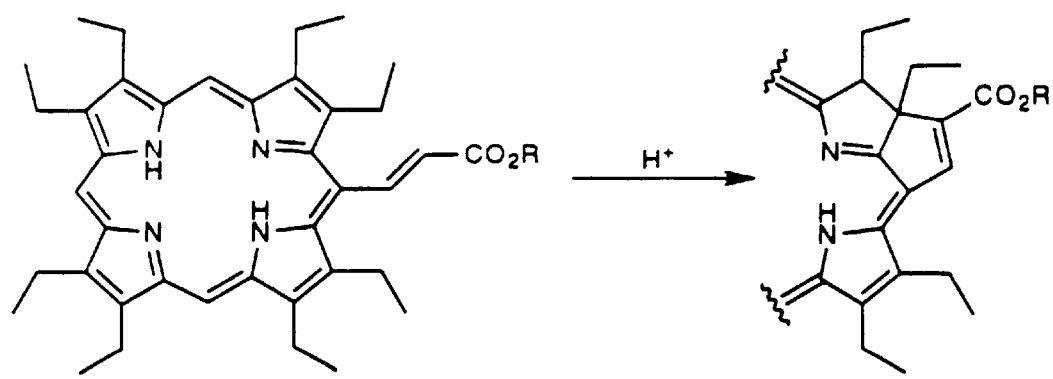
FIG. 5 depicts the synthesis of purpurins.
Figure 5:
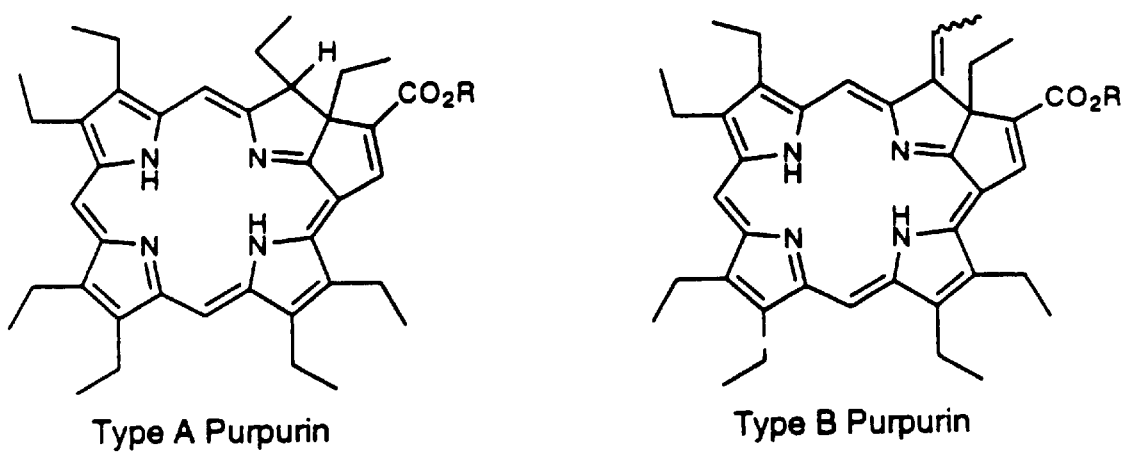

The formation of these products (93) from the cyclization reaction was somewhat surprising, as it requires a formal oxidation. The expected product, given that the desired 1,2-dialkyl shift did not take place, and the carbocation created by the cyclization process was quenched instead by the loss of a proton from the attached β-ethyl group, would be the imino-alcohol (94) (FIG. 4). In (93), the carbonyl group of the ketone is in conjugation with the imine double bond, which may increase its stability with respect to the alcohol, but the mechanism by which this transformation occurs is unclear. However, a similar oxidation is seen during purpurin synthesis (see below) when the reaction mixture is refluxed open to the air; in that case oxygen is presumed to be the oxidant.

produced by the acid-catalyzed cyclization of (metal-free) meso-acrylic esters (FIG. 5A). There are two types of purpurins, named type A and type B. Type A purpurins possess an sp$^3$ carbon atom on the reduced pyrrole ring, adjacent to the exocyclic ring, while type B purpurins have an sp$^2$ carbon at this position (FIG. 5B).

The formation of type B purpurins requires a formal oxidation after cyclization. In some cases, the type A compound is produced when the cyclization is performed under nitrogen, while the type B arises when this step is performed in a vessel open to the air. However, this is not always true, and the outcome varies according to the particular system. Studies are on-going in this area to elucidate the mechanism controlling the formation of the two types of purpurin (for background, see K. M. Smith et al., *J. Org. Chem.*, 48, p.500, 1983 and A. R. Morgan et al., *J. Org. Chem.*, 51, p. 1347, 1986) The cyclization of the imine displays characteristics of a type B purpurin synthesis, although the product contains a 6-membered exocyclic ring, reminiscent of a benzochlorin preparation.

Figure 6:
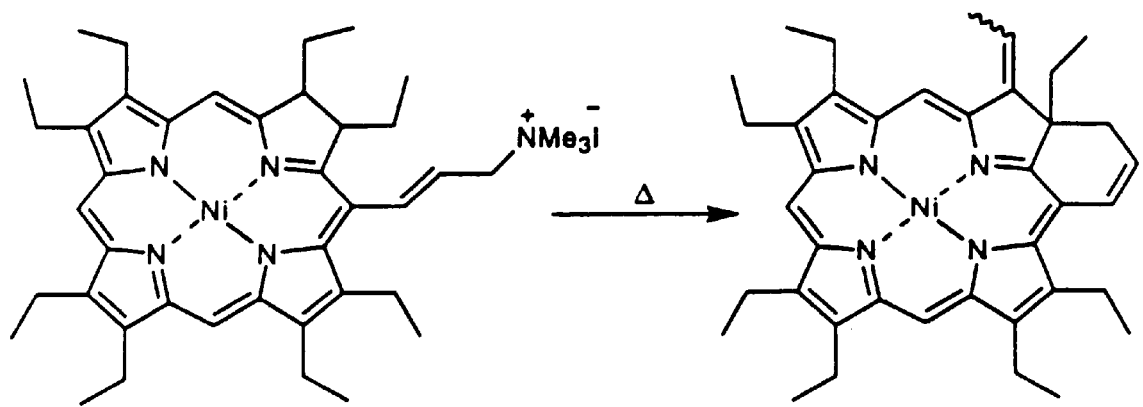
FIG. 6 depicts the synthesis of australaochlorins.

Very recently a report of a system bearing similarity to our own appeared, describing the synthesis of a new class of chlorins possessing 6-membered exocyclic rings, the "australochlorins" (D. Yashunsky et al., Aust. J. Chem., 50, p. 487, 1997). These compounds are isomeric with the benzochlorins but have a β-ethylidene group adjacent to the fused ring, which is non-aromatic. They are obtained by the thermolysis of the trimethylammonium salt as a mixture of two geometric isomers in a ratio of 10:7 (FIG. 6). Spectroscopically, these compounds are typical metallochlorins, absorbing at 643 nm, and hence are less interesting as potential photosensitizers than (93), which has a significantly red-shifted spectrum.

Although the cyclization experiments performed to this point had been successful in producing quantities of the product (93) sufficient to allow its structure to be assigned, it obviously was desirable to attempt to improve upon the yield of 15%. The reaction was repeated using Montmorillonite K10 clay as a solid acid catalyst. This reagent has been used previously in acid-catalyzed reactions such as porphyrin syntheses, as it appears that the pore size of the clay is a good fit for allowing the entry of a porphyrin, while being small enough to hold such a species in a restricted conformation suitable for intramolecular cyclization reactions. The addition of a small amount of activated Montmorillonite clay to the toluene solution of the imine (92) doubled the yield of (93) to 30% after overnight reflux. However, although the solvent and reaction time were varied, no further improvements were made to the efficiency of the cyclization, since the competing hydrolysis reaction limited the yield by destroying the imine starting material. Significant quantities of the aminoporphyrin (91) were recovered after each cyclization reaction, and this could be reused in the glyoxal condensation to regenerate (92).

In order to see if the cyclization would have a different outcome if performed in the absence of air, in analogy with some purpurin syntheses, the reaction was performed under nitrogen. However, the same mixture of isomers was obtained as previously. In an attempt to convert the isomeric mixture to a single compound, efforts were made to reduce the ethylidene double bond of (93) by catalytic hydrogenation, but only decomposition products resulted. The mixture was then subjected to diimide reduction, a reaction known to reduce symmetric double bonds in preference to double bonds between heteroatoms, but in this case, surprisingly, reduction occurred at the carbonyl group, giving the isomeric mixture of alcohols (94) (the same mixture that initially had been expected to result from the cyclization reaction, see FIG. 4). The identity of this compound was confirmed by reaction of the original isomer mixture with sodium borohydride, which gave the same species as its major product.

The alcohol product (94) gave the following selected resonances in the 400 MHz $^1$H NMR spectrum (only signals for the major isomer given, for clarity): a quartet at −0.23 ppm (methyl of the angular ethyl group), a doublet at 2.63 ppm (methyl of the ethylidene group), a singlet at 4.50 ppm (C$\underline{H}$OH) a quartet at 6.62 ppm (methine of the ethylidene group), and a singlet at 7.88 ppm (C$\underline{H}$=N). The longest-wavelength absorption peak was blue-shifted relative to (93) to 686 nm, reflecting the loss of the conjugated ketone.

As attempts to convert (93) to a single compound were unsuccessful, the two isomers were separated by preparative thin layer chromatography, using a 0.5 mm silica plate. There was sufficient differentiation between the two bands to be able to acquire the major isomer (93a) in good purity. The minor isomer (93b), owing to slight trailing of the faster moving major compound, as well as to its presence in much smaller quantity, was more difficult to isolate in a completely pure state, but a reasonable $^1$H NMR spectrum of it was obtained. NOE experiments on (93a) indicated that this compound has the Z-configuration, where the ethylidene methyl group is in the sterically less constrained position, pointing away from the angular ethyl group. This is analogous to the type B octaethylpurpurin situation, where the Z-geometry about the double bond was observed (although in that case no trace of the E-isomer was reported). The major isomer formed in the australochlorin synthesis also had the Z-geometry.

The intention had been to produce a compound with an aromatic exocyclic ring. The major impediment to aromaticity in the cyclic product (93) is the presence of the angular ethyl group. In steroid chemistry, an angular methyl group has been removed from androster-1,4-diene-3-one via a radical mechanism using zinc to generate the aromatic A ring (FIG. 7A, see also K. Tsuda et al., *J. Org. Chem.*, 26, p.2614, 1961; and K. Tsuda et al. *J. Org. Chem.*, 28, p. 795, 1963).

Figure 7:
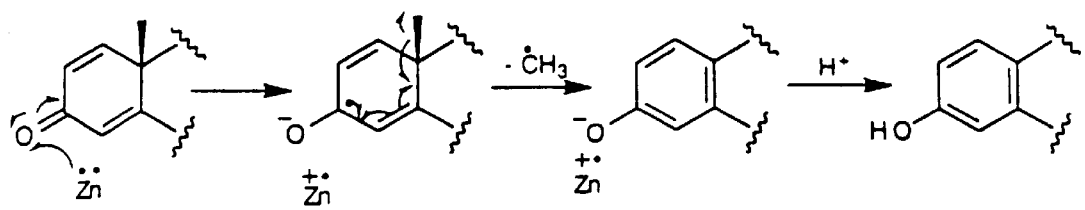
FIG. 7 depicts a postulated mechanism for the removal of the angular ethyl group of species (93) based an analogous reaction known for steroid ring A.
Figure 7:
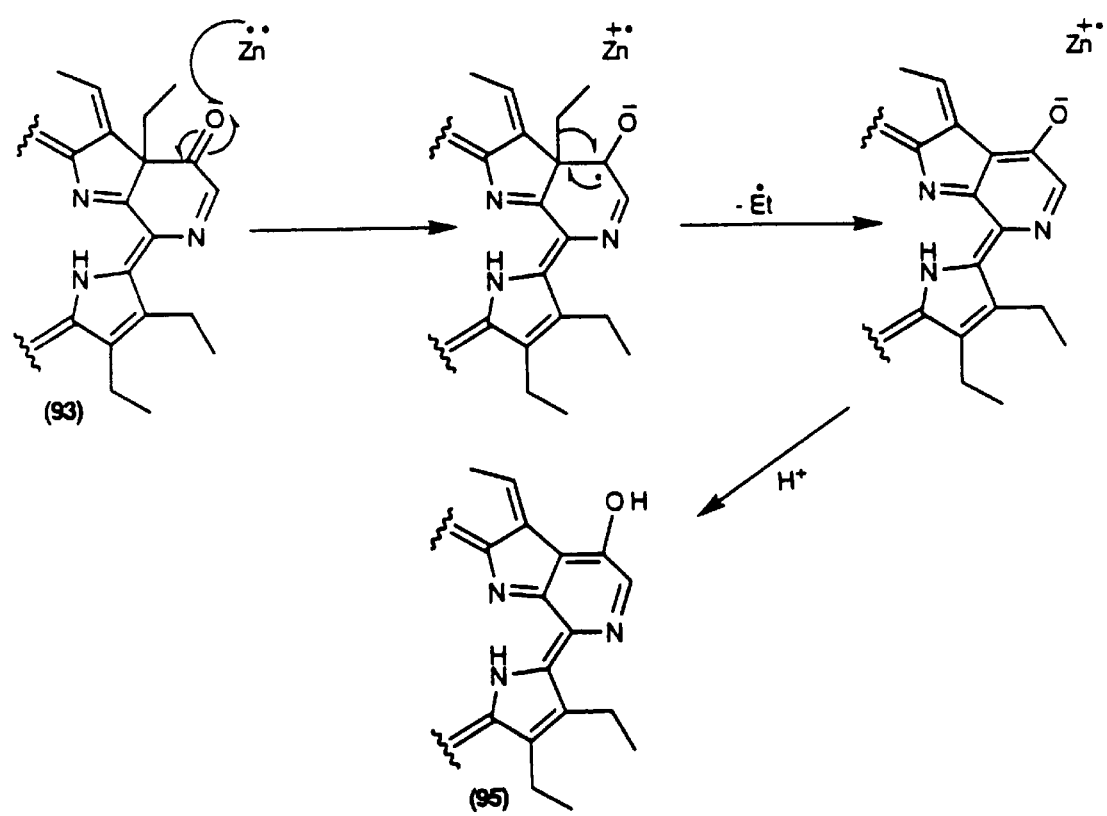

As the exocyclic ring of (93) has a similar structure to the steroid A ring, it seemed possible this reaction might remove the angular ethyl group in an analogous way to yield the 3-hydroxypyridine structure (95) shown in FIG. 7B.

However, on refluxing the isomeric mixture (93) in pyridine in the presence of a large excess of zinc powder and a drop of water, only the zinc complex of the starting material (Zn-93) was obtained. At this point it appeared that the possibilities of this compound had been exhausted, and other strategies towards the desired goal were considered.

Figure 8:
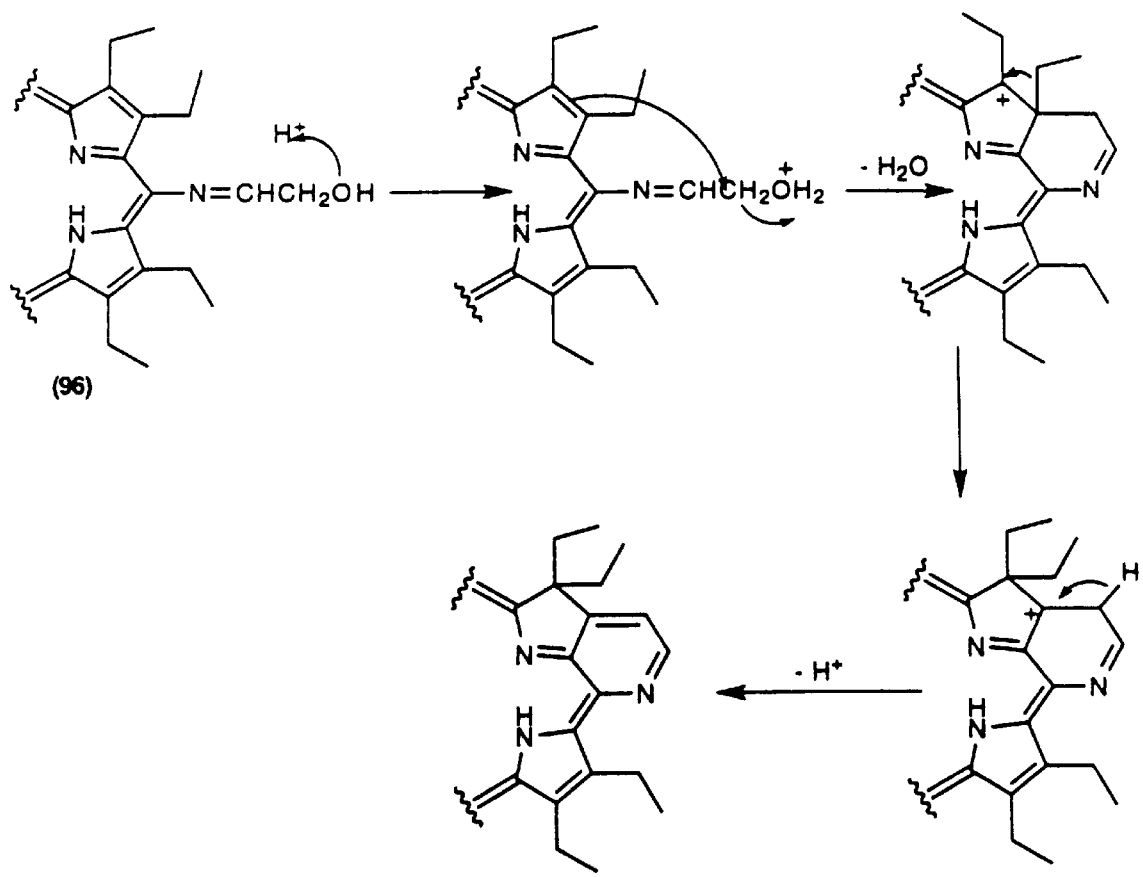
FIG. 8 depicts a possible cyclization reaction for glycolaldehyde condensation product, species (96).

The replacement of glyoxal by glycolaldehyde in the condensation reaction would yield an imine (96) which might be more likely to lead to the desired product, as under acidic conditions the hydroxyl group would be lost and the resulting carbocation might easily lose a proton from the exocyclic ring to become aromatic (FIG. 8). The analogous cyclization of the metal-free meso-(3-hydroxypropenyl) octaethylporphyrin has been reported to give quantitative yields of octaethylbenzochlorin.

Unfortunately, despite several efforts, the condensation of glycolaldehyde with meso-aminooctaethylporphyrin (91) was not achieved. Possibly this is a consequence of the difficulty of depolymerizing the dimeric glycolaldehyde to its monomer, although a reaction of this type with an aliphatic amine is reported to give good yields on stirring at room temperature in THF (see J. S. Davies et al., *J. Chem. Soc., Perkin Trans.*, 2, p. 201, 1991). In a different strategy to form the desired imine alcohol. attempts were made to condense glyoxalic acid to form the imine carboxylic acid and then reduce this to the alcohol (96). It appeared that the condensation reaction was successful, but on work-up, despite being careful to maintain very slightly basic conditions, the product reverted to the starting material (91), suggesting auto-hydrolysis of the imine double bond by the carboxylic acid functionality.

Figure 9:
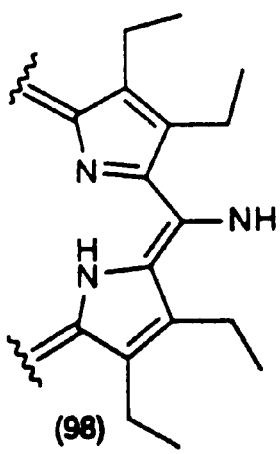
FIG. 9 depicts the structure of amines (98) and (99), synthesis of which was unsuccessful.
Figure 9:
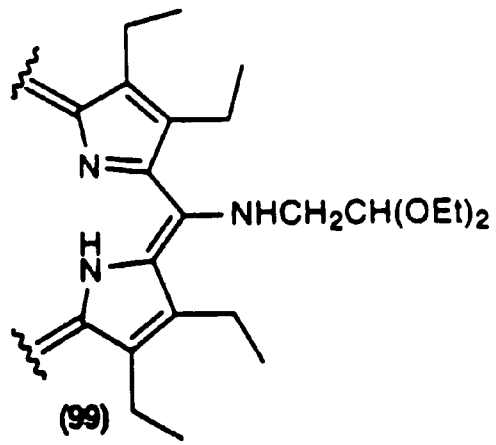

The next approach was to use the amine (91) as a nucleophile, to attack alkyl halides such as 1.2-dibromoethane and 1-bromo-2-(diethylacetal)ethane, and give the amines (98) and (99) (FIG. 9), which could then be used in cyclization reactions. However, in both of these cases no reaction occurred: it seems that the nucleophilicity of the nitrogen atom is low, presumably as a consequence of delocalization of the lone pair into the aromatic system. It was clear from these unsuccessful reactions that a different method was necessary to form the desired acyclic precursors with nitrogen in the α-position.

Efforts were then redirected to the β-pyridochlorins, with the expectation that they would in general be easier targets, and that the involved mechanisms would provide further insights into the efficient synthesis of α-pyridochlorins.

Example 2

Synthesis of β-pyridochlorin

Figure 10:
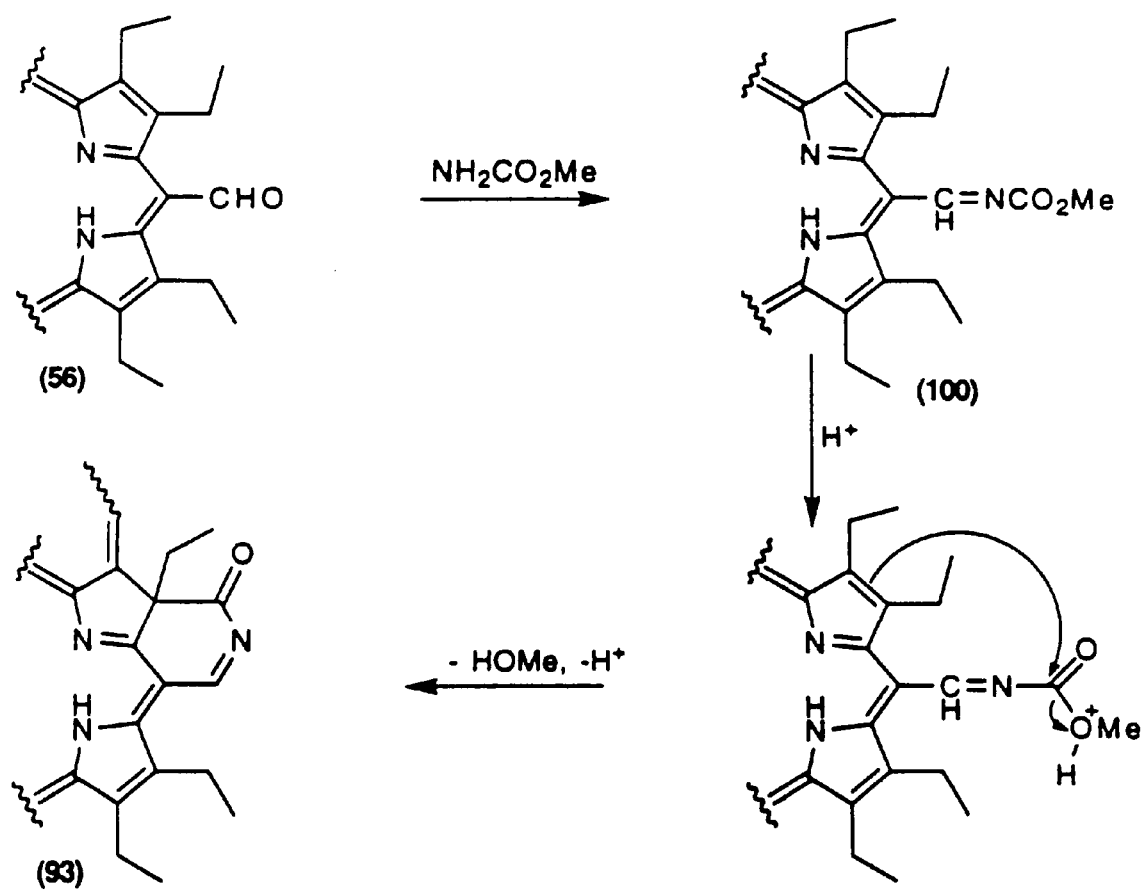
FIG. 10 depicts a methylcarbamate condensation of (56) with subsequent cyclization.

In considering methods for synthesizing the acyclic precursor to the β-pyridochlorin., one might consider an approach very similar to that used for the α-pyridochlorin, and thus condensing the meso-formylporphyrin (56) (FIG. 10) with an appropriate amine, to obtain the β-imine. Unfortunately, the necessary amine would be formamide, and amides do not possess the required nucleophilicity for the condensation. However, methylcarbamate, with greater nucleophilicity at the nitrogen atom, would produce a condensation product (100) potentially useful for the cyclization (FIG. 10). This condensation was attempted but despite the use of a various conditions, no reaction was observed, and the mesoformylporphyrin was recovered unchanged.

Another potential way to make compounds with nitrogen in the desired position would be to displace a leaving group on the meso-methyl group of the porphyrin with a nitrogen nucleophile such as ammonia. The meso-hydroxymethyl compound (101) can be made by sodium borohydride reduction of the formyl group of (56). Efforts were made to convert this first to the p-toluenesulfonate ester, and then displace the p-toluenesulfonyl group with ammonia gas. During the first experiment, the intermediate ester was worked up, and an attempt was made to isolate it, but it appeared to be very reactive, and decomposed. Consequently, a second reaction was run, and this time the in situ formed p-toluenesulfonate was reacted with ammonia gas. However in this case, only the hydroxymethyl starting material was recovered. The next approach was a reductive amination of the meso-formyl compound (56), using ammonium acetate and sodium cyanoborohydride, in another attempt to form the meso-aminomethylporphyrin. Once again, no reaction was observed.

Having employed reactions well-known to work in typical organic systems, but without success, literature methods that described reactions specific to porphyrins were examined. There is one report of a condensation of an amine with meso-formyloctaethylporphyrin (56), the amine being β-alanine, and the yield was only 15% (J- H. Fuhrhop et al., *Liebigs Ann. Chem.*, p. 1537, 1976) As this synthesis had been attempted with methylcarbamate without success, it was not pursued further. Another paper describes the condensation of meso-formyletioporphyrin with aniline and p-anisidine, with very good yields. However, this approach requires the use of the amine as solvent, and the compounds thus produced, being aromatic Schiffs bases, are structurally further from the desired product than the alanine conjugate mentioned, and it was felt that the latter was a more realistic model for the present systems. A more commonly used preparation of β-nitrogen-substituted porphyrins involves the formation of the oxime of the meso-formylporphyrin using hydroxylamine hydrochloride in refluxing pyridine (A. W. Johnson, *J. Chem. Soc.* (C), p. 794, 1966). The oxime can be dehydrated to give the cyano group, which is reported to yield the meso-carboxylic acid by hydrolysis in sulfuric acid, although this latter report has been shown to be in error (P. S. Clezy et al., *Aust. J Chem.*, 27, p. 110, 1974) and will be discussed in more detail below.

Figure 11:
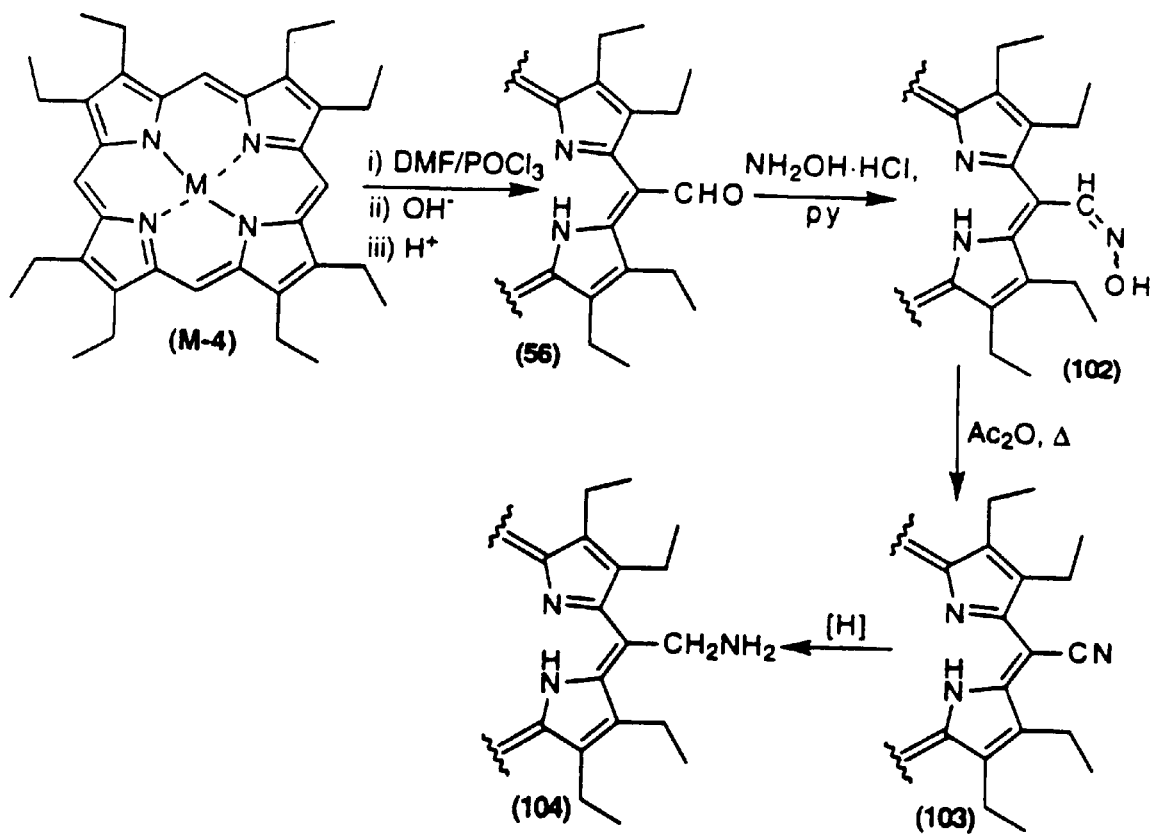
FIG. 11 depicts a proposed route to meso-aminomethyloctaethylporphyrin (104).

The meso-cyanoporphyrin (103) provides a route to the meso-aminomethyl compound (104) via reduction (FIG. 11). Hence meso-cyanooctaethylporphyrin was synthesized. and attempts were made to reduce it. However, this compound was extremely resistant to the many reagents used (lithium aluminium hydride, aluminium hydride, borane-dimethylsulfide complex, diborane, catalytic hydrogenation). In most cases, the starting material was recovered unchanged, although in the case of catalytic hydrogenation over palladium on charcoal, the porphyrin ring was reduced at one of the meso-positions to give the green phiorin, which slowly reoxidized to the porphyrin. Reduction of the nickel complex of the meso-cyano compound was also attempted, as the reactivity of a metalloporphyrin can differ markedly from that of the corresponding free base. However, there was no improvement in reactivity; the only differences being a lack of reaction during catalytic hydrogenation, and the partial loss of the cyano-group during treatment with lithium aluminium hydride. These disappointing results prompted the search for another strategy.

As aforementioned, it was reported that the hydrolysis of meso-cyanoetioporphyrin in hot concentrated sulfuric acid gave the carboxylic acid (A. W. Johnson, *J. Chem. Soc.* (C), p. 794, 1966). Clezy et al. reinvestigated this reaction and discovered that the product was in fact the amide. The same reaction was performed on the octaethylporphyrin analog with identical results, and despite using various forcing conditions, no further hydrolysis of the amide (105) was seen. This amide is a potentially useful intermediate in the synthesis of cyclization precursors (FIG. 12), as it would lead via reduction to the desired meso-aminomethylporphyrin (104). Unfortunately, reduction of the amide (105) using, lithium aluminium hydride in dry THF under nitrogen resulted in formation of the meso-cyano compound (103), i.e. the dehydration product. This was formed in 35% yield, with the remainder of the yield being decomposition products, suggesting the possibility that the aminomethyl product was formed, but that it was too unstable to be isolated. The nickel complex of the amide was also synthesized in order to see if it would be more easily reduced by treatment with the same reagent. In this case, no reaction occurred at room temperature, but after refluxing, the major product was nickel octaethylporphyrin. This follows the same trend as with the nickel cyano-derivative: the nickel complexes appear to readily lose their meso-substituents under basic conditions.

Figure 12:
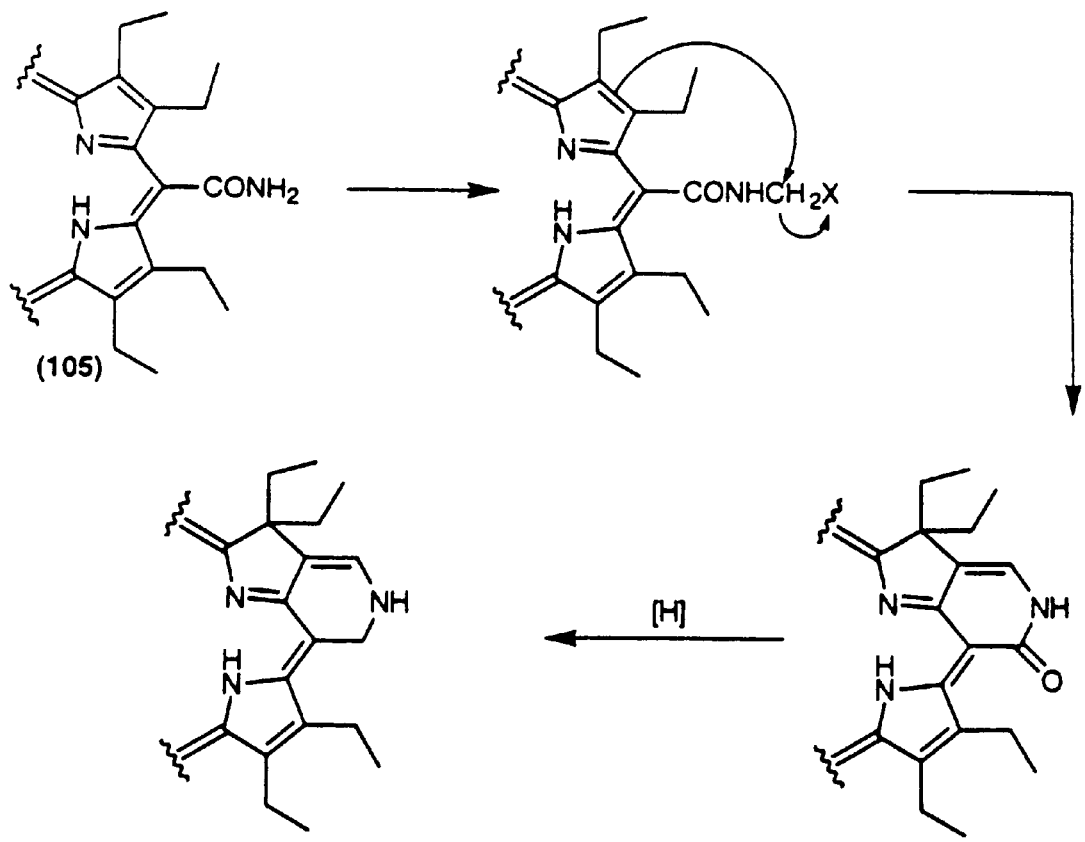
FIG. 12 depicts a proposed use of (105) as a cyclization intermediate.

Thus, despite many efforts, no practical method for preparing the desired aminomethyl-substituted porphyrin (104) had been found. However, the meso-amide (105) could be produced. Although no progress had been made in reducing this compound, it was hoped that it could be converted into a cyclic chlorin with an excocyclic amide functionality, and that this cyclic product would prove more amenable to reduction (FIG. 12).

Figure 13:
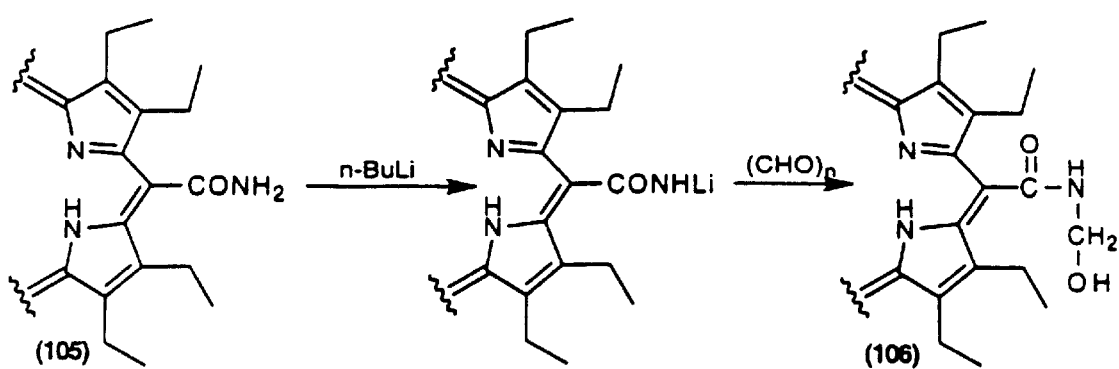
FIG. 13 depicts the synthesis of Compound 106.

In order to make the precursor to the cyclization step using the amide, it was necessary to alkylate the nitrogen atom with a functionalized methyl group susceptible to nucleophilic attack under acidic conditions, ideally a formyl or a hydroxymethyl group. Amides can be hydroxymethylated at the nitrogen atom using paraformaldehyde and base. A small-scale test reaction was run using sodium methoxide as base in refluxing THF: this lead to the formation of a more polar compound with a $^1$H NMR spectrum consistent with the desired product (106). Subsequent trials suggested that the quantity of base was crucial to the success of the reaction, as a large excess lead to the formation of a more polar compound which was initially attributed to the doubly alkylated species, produced by deprotonating the nitrogen atom of the N-hydroxymethyl compound and reacting with a second equivalent of paraformaldehyde. As it evidently was important to control the quantity of base used, sodium methoxide was replaced by n-butyllithium, as this is easier to measure out in small quantities. Using 1.5 equivalents of this base in THF at room temperature, a 70% yield of the meso-(N-hydroxy methyl) aminocarbonyloctaethylporphvrin (106) was obtained (FIG. 13).

The nickel complex of the N-hydroxymethyl compound was also of interest, as the cyclization outcome can vary depending on whether the free base or metallated species is used (for example, refluxing the metal-free meso-acrylaldehyde of octaethylporphyrin in acetic acid leads to the purpurin, whereas the nickel complex is unaffected by these conditions, see D. P. Arnold et al., *JCS Perkin I*, p. 1660, 1978). Therefore the metal-free form of (106) was subjected to the standard nickel complexing conditions: addition of nickel acetate tetrahydrate in refluxing DMF. Unfortunately, upon work-up of this reaction, it was found that the hydroxymethyl group had been lost, and the product was the nickel amide (Ni-105). The hydroxymethyl group was also lost under the conditions used for EI (electron impact) mass spectrometry (at 200° C.), so FAB (fast atom bombardment) was used for these compounds. The metallation with nickel was run at 50° C., and a 70% yield of the desired product (Ni-106) was obtained after 3 days (the remainder of the recovered material was the unchanged starting material). In view of the very slow metallation at the lower temperature necessary to preserve the integrity of the compound, it seemed more efficient to make the nickel derivative by hydroxymethylation of the nickel amide (Ni-105). This was found to work well, although the first trial using 1.5 equivalents of n-butyllithium resulted in a poor yield, or the desired compound and a large amount of more polar material.

Figure 14:
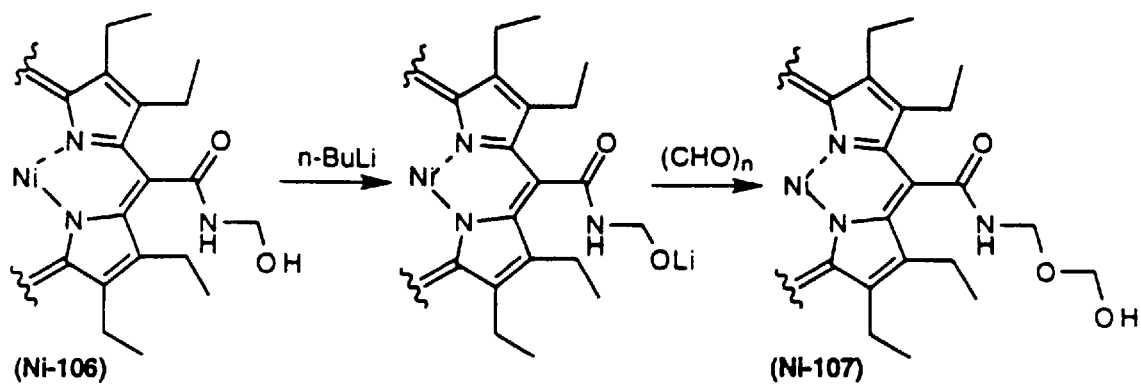
FIG. 14 depicts a side-product from N-hydoxymethylation of (Ni-105, nickelated 105).

Again, it was initially believed that this side-product was the result of bis-hydroxymethylation at the nitrogen atom, but in this case there was now enough compound to study spectroscopically, and it was found to be the product of hydroxymethylation at the N-hydroxymethyl oxygen atom (Ni-107, FIG. 14). This is an obvious result, given the relative pKa's of an alcohol (15 to 19) compared with an amide (25). Consequently, the reaction was repeated using 0.5 equivalents of n-butyllithium, to minimize formation of the side-product, and a 76% yield of the target molecule was obtained. It is interesting to note the differences between the reaction using the metal-free amide and that with the nickel amide: the latter appears to require only catalytic amounts of base, whereas the former requires at least stoicheometric quantities. Presumably this is due to the central NH's in the metal-free compound, one of which is deprotonated by the base to give the monoanion-apparently the conditions are not such that the dianion is formed, as fewer than 2 equivalents of base are necessary.

Both the metal-free and the nickel-complexed N-hydroxymethylamides (106) and (Ni-106) had been prepared, ready for cyclization studies. The first experiment entailed stirring the nickel complex in dichloromethane solution with a drop of the Lewis acid, boron trifluoride etherate. This represents one method for making metallated benzochlorins from their acyclic precursors. On work-up after three hours, there appeared to be two major products (Ni-108, present in different proportions), both more polar than the starting material. An attempt was made to separate these compounds by chromatography, but only the less polar one was obtained pure, as both compounds had poor solubility and streaked throughout the column. A $^1$H NMR spectrum of the pure compound was run, but very broad signals resulted, and this was thought to arise from aggregation of the compound in solution. However, the visible spectrum did give cause for optimism, as it displayed a large absorption peak at 646 nm, suggestive of a nickel chlorin.

The next cyclization attempt involved treatment of the nickel complex (Ni-106) with concentrated sulfuric acid. A peak was seen in the visible spectrum of the neutralized reaction mixture at 680 nm, indicative of a metal-free chlorin. On work-up a green-brown product (108) slightly more polar than the starting material was isolated in 70% yield. Although by TLC this appeared to be one compound, the $^1$H NMR spectrum showed it to be a 1:1 mixture of two isomers. The visible spectrum of the isolated mixture showed a double long-wavelength absorption peak at 680/686 nm. The $^1$H NMR spectrum was reminiscent of that of the isomeric a-pyridochlorin mixture (93) made previously, and it was obvious that the two isomers arose from the same ethylidene functionality as in that case. The compound was assigned the structure shown below.

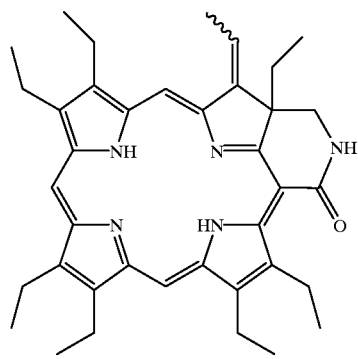

(108)

The metal-free cyclization precursor (106) was treated with sulfuric acid. with identical results. The 0-hydroxymethylated side-product (Ni-107) (FIG. 14) was also subjected to the same conditions, resulting in isolation of the same product. Finally. the mixture of nickel lactams (Ni-108) from the boron trifluoride reaction was stirred with concentrated sulfuric acid. Again, the same 1:1 isomeric mixture of metal-free lactams (108) was obtained. It is interesting to note that although there appears to be a major and a minor isomer formed in the BF$_3$ reaction, on stirring with sulfuric acid, a 1:1 mixture results—obviously equilibration occurs under strong acid conditions.

Once again, the products formed via loss of a proton from the β-ethyl group had been formed, rather than the desired compound that would result from a 1,2-dialkyl shift. A number of different cyclization conditions were investigated in the hope of finding a method that would lead to the target compound. The nickel N-hydroxymethylamide (Ni-106) was refluxed in chloroform with the acidic clay Montomorillonite K10 (the successful catalyst in the earlier cyclization reaction to make the α-pyridochlorin-type structure). However, in this case, although a trace of cyclized material was detected, the major products were nickel octaethylporphyrin and the nickel amide, with only a small amount of starting material. It is surprising to see that the meso-substituent was lost so easily under acidic conditions, as has already been observed under strongly basic conditions. Another cyclization was run using the metal-free N-hydroxymethylamide (106) in trifluoroacetic acid, and adding concentrated sulfuric acid dropwise until cyclization occurred. Here the thought was that one of the two isomers would be favoured, and the lower acid strength would prevent equilibration to the 1:1 mixture thus far seen. Unfortunately in this case, no cyclization occurred until a large quantity of sulfuric acid was added, and the usual isomeric mixture (108) was obtained.

Figure 15:
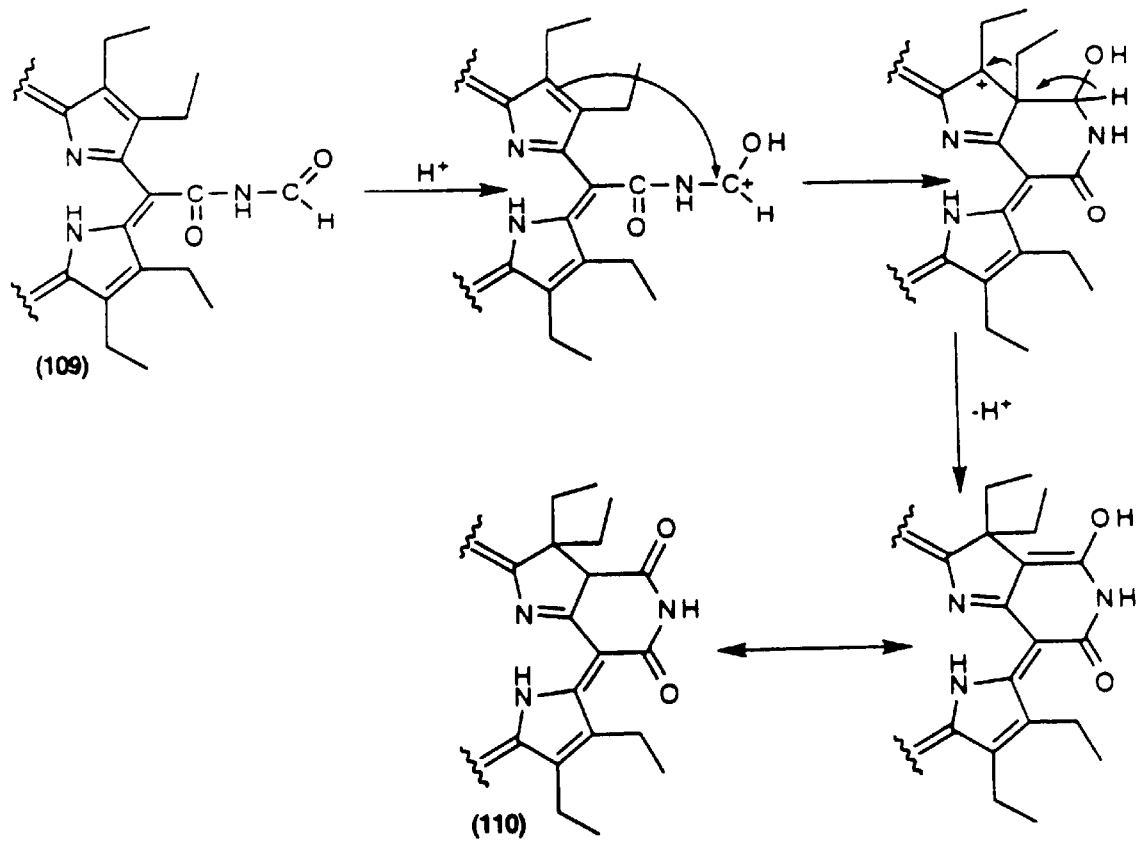
FIG. 15 depicts a proposed cyclization of N-formylamide compound (109).

The next line of approach was to synthesize the metal-free and nickel N-formylamide analogues (109) and (Ni-109), as there was an interest in determining if these would cyclize in the same manner, or if they might give the corresponding cyclic imides (110) (FIG. 15). The N-formylamides were produced by tetrapropylammonium perruthenate (TPAP) oxidation of the N-hydroxymethylamides (see W. P. Griffith, et al., *J. Chem. Soc. Chem. Commun.* p.1625, 1987). The oxidations proceeded smoothly to give the compounds in reasonable yields. The nickel complex (Ni-109) was treated with concentrated sulfuric acid, but no cyclization was observed, and the demetallated N-formylamide (109) and demetallated amide (105) were recovered. Dichloromethane/boron trifluoride etherate conditions were tried, but yielded only nickel octaethylporphyrin and a small amount of starting material. The metal-free N-formylamide (109) was then treated with dichloromethane/boron trifluoride etherate, but on work-up only starting material and the porphyrin amide were obtained. Finally, cyclization of the metal-free compound (109) in refluxing chloroform with Montmorillonite clay was attempted, and in this case the resulting compounds were starring material and octaethylporphnrin. In conclusion. the acid treatment of the N-formylamides appears to lead preferentially to hydrolysis of the N-forrnyl moiety rather than to cyclization.

Returning to the lactam (108), efforts were made to reduce the amide functionality which had resisted such a reaction before cyclization. However, once again, lithium aluminium hydride proved ineffective, both at room temperature and in refluxing TE. In each case, starting material was recovered.

Attempts were also made to remedy the fact that (108) was present as a mixture of isomers, rather than as a single compound. Catalytic hydrogenation over palladium on charcoal was performed on the isomeric mixture. This reaction met with some success, although it proved difficult to obtain reproducible results. During some experiments, no reduction was seen, while in others, good results were achieved. This may be due to the presence of small amounts of impurities that poisoned the catalyst. One observation common to all experiments was the formation of a large quantity of a more polar pink compound which appeared from its visible spectrum to be non-porphyrinic, possibly arising from reduction of the porphyrin ring. Unfortunately, this compound did not reoxidize to the chlorin on stirring in air, or even after the addition of an oxidizing agent such as 1,2-dichloro-4,5-dicyanoquinone (DDQ). Hence the yields for this reaction, even when "successful", were prohibitive. However, a single porphyrinic reduction product (111) was produced, reaction presumably taking place only on the least hindered side of the molecule, i.e. that opposite the angular ethyl group (it should be noted that both the α- and the β-pyridochlorins synthesized so far possess a chiral centre, and so exist as a mixture of optical isomers). The reduced compound exhibited a small blue-shift in the visible spectrum, the double peak at 680/686 nm becoming a single peak at 670 nm, reflecting the loss of the conjugated double bond of the ethylidene group.

Since the nickel complex of the lactam (Ni-108) gave very broad signals in the $^1$H NMR spectrum, there was interest in seeing whether other metal complexes displayed similar behavior. Consequently the lactam free base (108) was metallated with zinc. The zinc complex (Zn-108) displayed the same broadness in the $^1$H NMR spectrum as previously seen with the nickel complex, and so it appears likely to result from strong association of the complexed metal ftom one molecule with the amide group of another molecule, leading to aggregation in solution.

During the course of these efforts to produce a β-pyridochlorin, a report came to light detailing the synthesis of a meso-isocyanoporphyrin ( 112) (see P. S. Clezy, et al., Aust. J. Chem., 27, p. 1003, 1974). This was relevant to these studies as it provided an alternative approach to the formation of the α-pyridochlorin. The following section describes the strategy developed using this compound, and the subsequent results.

Figure 16:
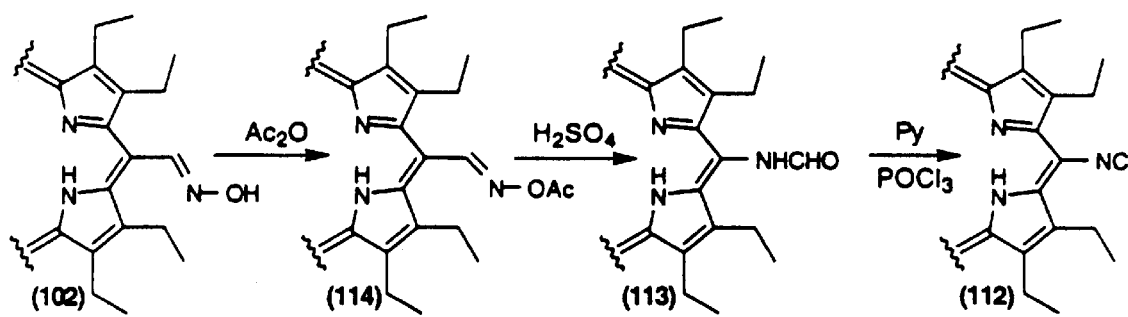
FIG. 16 depicts a synthesis of meso-isocyanooctaethylporphyrin (112).

Example 3
Additional approach to synthesis of α-pyridochlorin via meso-isocyanooctaethylporphyrin The meso-isocyanoporphyrin (1 12) is produced by the dehydration of the corresponding meso-formamide (113), which in turn is formed by a Beckmann rearrangement of the meso-acetoxime (1 14) in concentrated sulfuric acid (FIG. 16).

Figure 17:
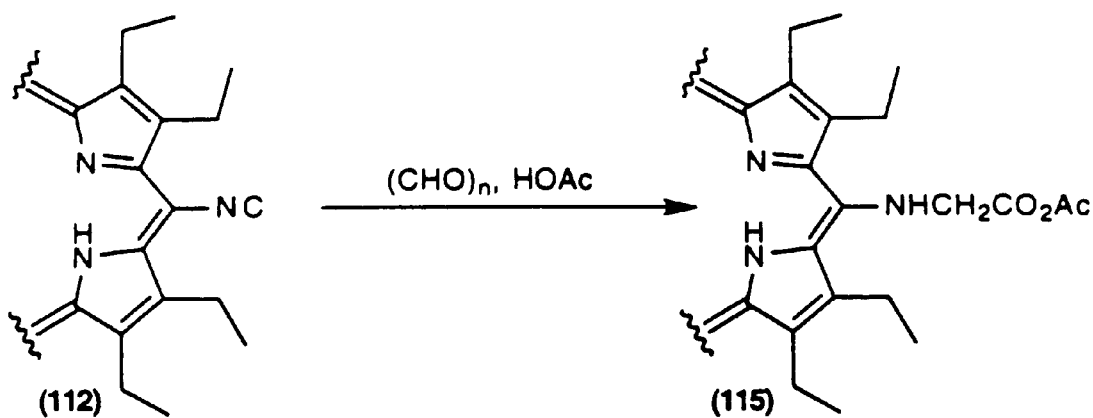
FIG. 17 depicts a Passerini reaction of (112).

A Passerini reaction (I Ugi ed. *Isonitriles*, Academic Press, New York, 1971) of the isocyanide with formaldehyde and acetic acid as attempted in an effort to obtain the alkylated amide (115) shown in FIG. 17. The product of this reaction would have been set up for acid-catalyzed cyclization to give a chlorin. However, on work-up, only the formamide (1 13) was isolated, formed by acid hydrolysis of the isocyanide.

Figure 18:
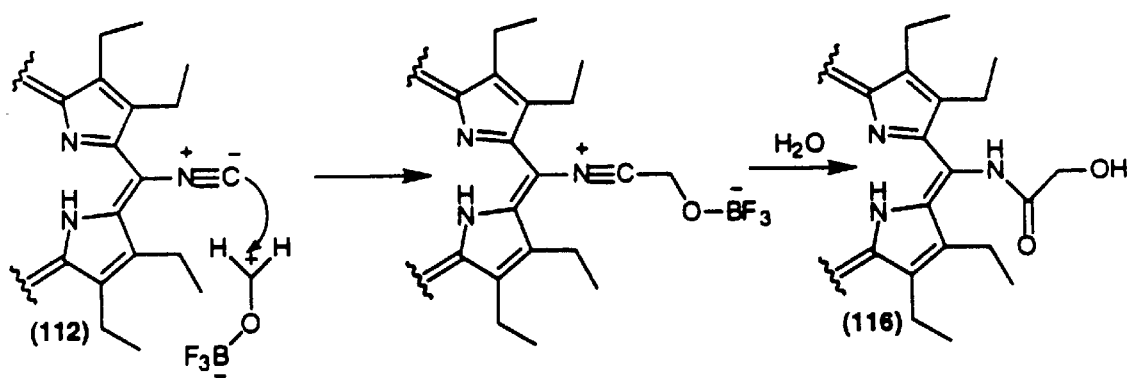
FIG. 18 depicts acid-catalyzed reaction of (112) with formaldehyde to give (116).

The next strategy involved reacting the isocyanide with formaldehyde in the presence of the Lewis acid, boron trifluoride etherate. It was envisaged that the nucleophilic isocyanide carbon atom would attack the carbocation of the formaldehyde-$BF_3$ adduct, to give the analog of the β-pyridochlorin cyclization precursor, with the nitrogen in the α-position (1 16), FIG. 18.

Formaldehyde gas was bubbled through a flask containing toluene, giving a solution of formaldehyde, to which was added boron trifluoride etherate. This solution was added to the solid isocyanide, and stirred at room temperature. After work-up, two compounds were isolated: the major product was the formamide (113), formed by hydrolysis of the isocyanide by $BF_3$. The other product was polar and highly insoluble. Spectroscopy showed this latter compound to be the desired species (116). Test reactions were run to see if (116) was susceptible to cyclization in acid, but neither reaction in dichloromethane with $BF_3$ catalysis, nor reaction in concentrated sulfuric acid lead to any trace of a cyclized product, and the starting material was recovered unchanged. In order to see if the nickel complex would be more prone to cyclization, the C-hydroxymethylamide was metallated with nickel, and this product (Ni-116) was subjected to the same reaction conditions described for the metal-free compound. The only reaction seen to occur was demetallation. Finally, attempts were made to oxidize the metal-free C-hydroxymethylamide (116) using TPAP to form the C-formylamide, in the hope that this might change the reactivity of the chain in favor of cyclization; however this oxidation reaction failed.

Figure 19:
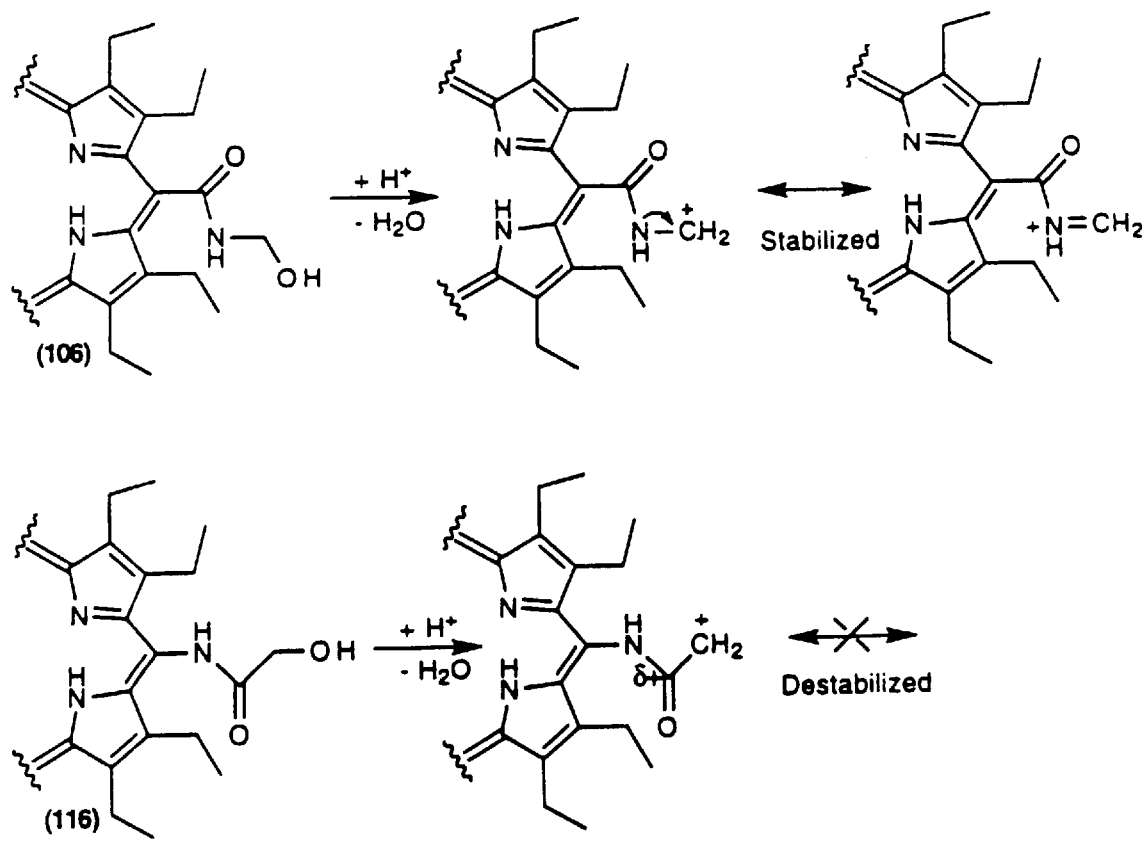
FIG. 19 depicts a rationale for the cyclization/lack of cyclization of the two types of hydroxymethylamide (106) and (116).

The lack of reaction of the C-hydroxymethylamide (116) compared with the N-hydroxymethylamide (106) can be explained by the relative stabilities of the carbocations which must be formed in order for cyclization to occur (see FIG. 19). In the case of the N-hydroxymethylamide, the carbocation is adjacent to a nitrogen atom, and hence can be resonance-stabilized by the lone pair on that atom This stabilization allows the cation to exist long enough for the double bond to attack it, leading to cyclization. In the case of the C-hydroxymethylamide, the carbocation would be created adjacent to a carbonyl group, i.e., adjacent to a partially positive carbon. Formation of the carbocation would lead to the highly unstable situation where two positive (or partially positive) atoms exist side by side. The lack of cyclization suggests that such a species either does not form at all, or its lifetime is too short to allow nucleophilic attack on it, leading to cyclization.

It was also intended to make more nickel C-hydroxymethylamide (Ni-116) by C-alkylating the nickel isocyanide (Ni-112) with paraformaldehyde/$BF_3$. Instead of obtaining the expected more polar hydroxymethyl compound, one major non-polar product was isolated, with an unusual visible spectrum (intense peaks at 406, 430, 496, and 680 nm and a low intensity peak at 814 nm). The $^1$H NMR spectrum showed by the presence of a six hydrogen triplet at −0.05 ppm that this compound possesses a gem-diethyl group, which lead to the suggestion that a cyclization had occurred in situ to give the unsaturated lactam (Ni-117).

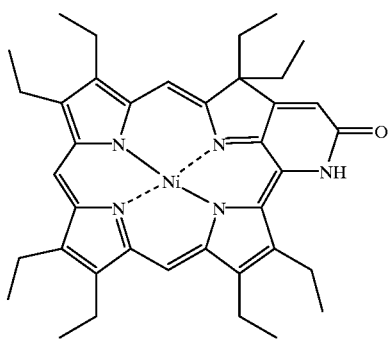

(Ni-117)

Figure 20:
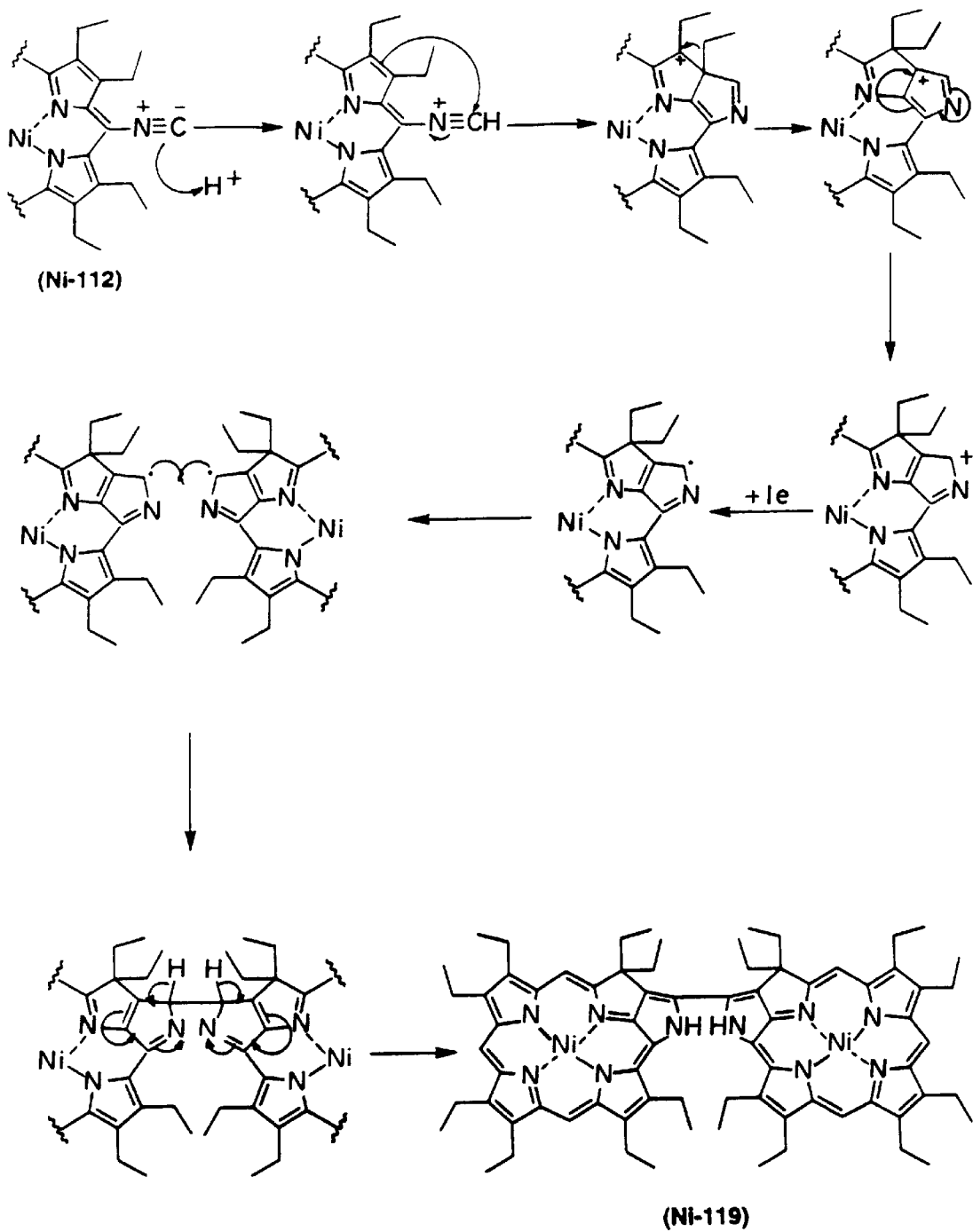
FIG. 20 depicts a possible mechanism for the formation of the dimeric structure (Ni-119).

However, this structure was not consistent with the ¹H NMR spectrum, as there were no signals corresponding to the proton a to the NH, even if the NH signal itself were too broad to be distinguished. Despite its low polarity, the product was very slow to dissolve, and had a melting point higher than most octaethylporphyrin derivatives. These facts, coupled with the atypical visible spectrum, suggested that the compound might be a dimer, and so it was submitted for FAB mass spectrometry, which confirmed this. A mechanism can be drawn for the formation of a dinner (Ni-119) consisting of two units of (Ni-118) joined at the carbon a to the nitrogen atom (FIG. 20).

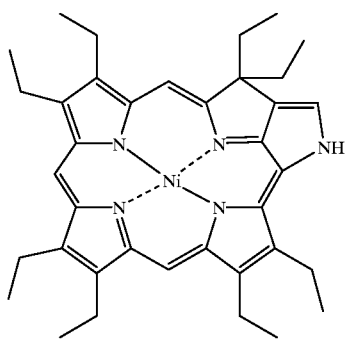

(Ni-118)

This mechanism requires the addition of two equivalents of H⁺ and two electrons per molecule of dimer. Excess BF₃ was used, and accounts for the acid requirement, but reduction under these conditions might seem harder to explain. However, the formation of nickel octaethylbenzochlorin (Ni-17, see also FIG. 1) also requires a formal reduction to take place under similar conditions, and it is suggested that nickel porphyrin complexes can act as electron donors under acidic conditions (see D. P. Arnold et al., *JCS Perkin*, I, p. 1660, 1978). It should be noted that the best yields of this reaction were approximately 50%, and a large quantity of non-porphyrinic decomposition product was always obtained, reinforcing the possibility of electron donation from two porphyrin molecules to two others to form the dimer, followed by decomposition of the two porphyrin cation radicals. Also, the fact that the reaction only occurs when the nickel complex is used, and no cyclizaton/dimerization is seen with the metal-free compound, suggests that the nickel is playing an important role. The proposed structure would be consistent with the ¹H NMR spectrum, the only signals not observed being the NH protons.

Figure 21:
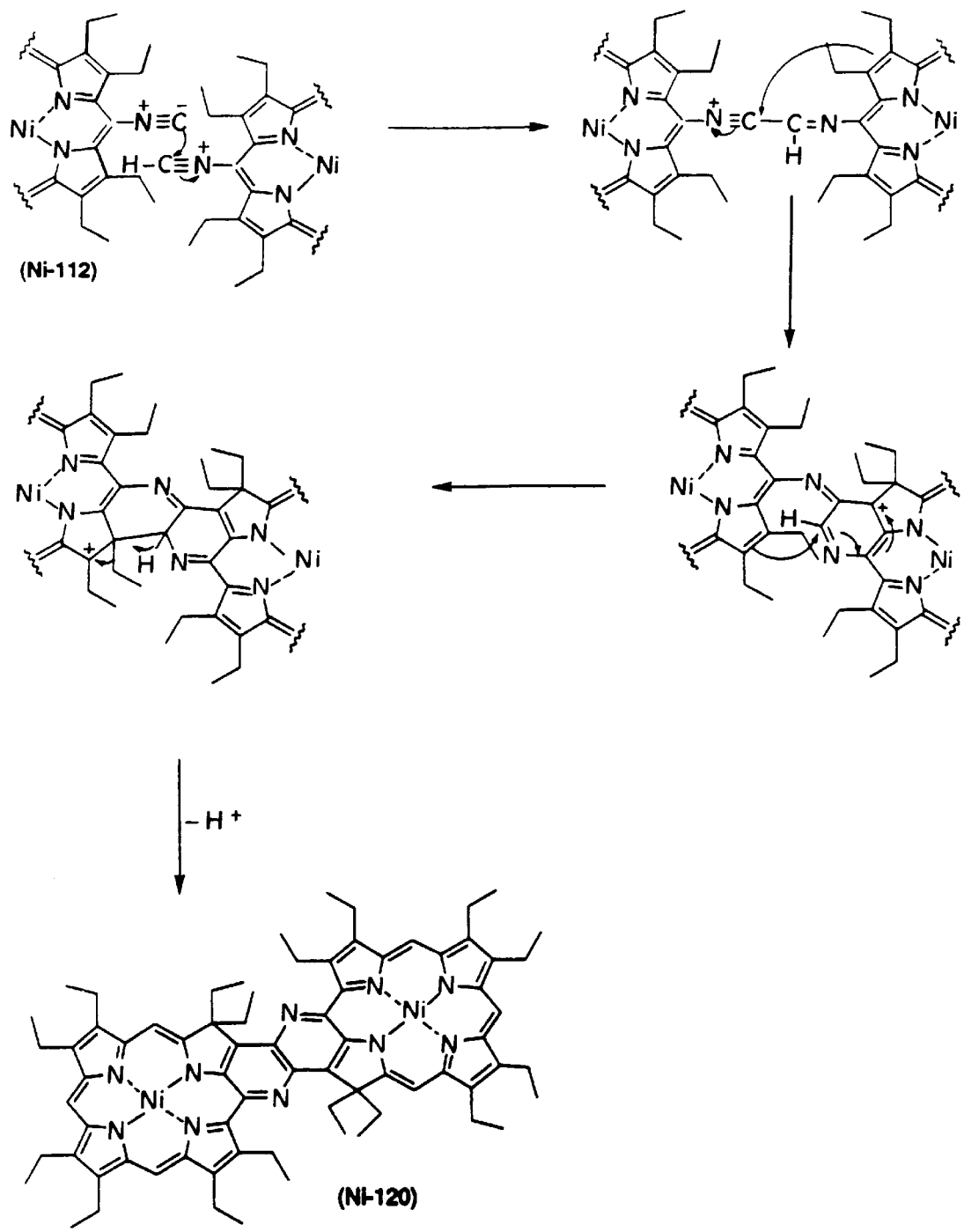
FIG. 21 depicts a mechanism for the formation of the dimer (Ni-120).

The final structure (Ni-120, FIG. 20) was ascertained by X-ray crystallography, and was significantly different to that proposed. This structure contains a pyrido[3,2-b]-pyridine unit linking the two chlorin molecules. It possesses two fewer hydrogen atoms than the proposed structure, and fits better with the mass spectrum (however, without the hindsight made possible by a crystal structure, it would have been difficult to be certain of the exact number of hydrogen atoms in the dimer simply by FAB mass spectrometry, as such an ionization method sometimes gives rise to molecular ion peaks corresponding to the gain of one or more hydrogens). A mechanism can be drawn for the formation of this dimer which is catalytic in acid, and has no need for the reduction step (FIG. 21). Finally, this structure is completely consistent with the ¹H NMR spectrum, and there are no "missing" signals.

This result was extremely interesting. The objective of this Example was to create a chlorin with a fused pyridine ring, which so far was difficult to effect. In this reaction, finally this objective had been achieved, but "in duplicate," in the form of a dimer. In all previous cyclizations, the alkyl 1,2-shift did not occur, and instead the ethylidene product resulting from the loss of a proton from the ethyl group was obtained. This did not appear to happen in this case. However, when the dimerization reaction was run on a larger scale, and the product was very carefully isolated, another compound was seen running just behind the dimer (Ni-120) on TLC. After purification by column chromatography, ¹H NMR and mass spectra of this fraction were obtained, and it was revealed to be the ethylidene analogue of the dimer, in which there is one ethylidene group, one angular ethyl group, and one gem-diethyl group (Ni-121). As there is now no symmetry in the molecule, the ¹H NMR spectrum is much more complex. Two noteworthy points about this minor product are (a) that it exists as one isomer, i.e., there is only one geometry about the ethylidene bond (although the presence of a chiral cenetre at the angular ethyl group gives rise to optical isomers) and (b) that its visible spectrum differs greatly from that of the major dimeric product, possessing a Soret band at 410 nm and very little absorption at longer wavelengths. The angular hydrogen atom at the position of fusion of the two pyridine rings prevents these rings from becoming aromatic, and this presumably prevents interaction between the two porphyrin moieties and accounts for the more porphyrin-like visible spectrum.

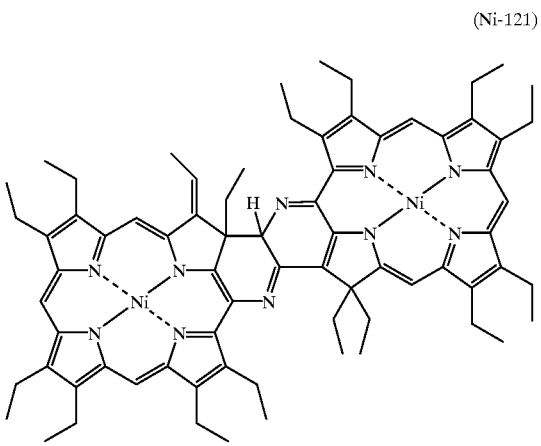

(Ni-121)

The major nickel dimer (Ni-120) was demetallated in concentrated sulfuric acid to give a very insoluble grey product (120). The ¹H NMR spectrum of this product showed two new singlets at 4.97 ppm 5.82 ppm, exchangeable with D₂O, but no signals were seen upfield of 0 ppm, in the region where the central NH protons are usually observed. It is possible that the pyridine nitrogens are more basic than the central nitrogens, and that it is the protonated pyridine NH's that give rise to the new signals. High resolution FAB mass spectrometry confirmed that demetallation had occurred. Further confirmation was obtained by complexing the demetallated compound with zinc; the zinc dimer (Zn-120) thus obtained displays a $^1$H NMR spectrum very similar to that of the nickel complex. The nickel, zinc and metal-free compounds all possess similar visible spectra.

Example 4

α-Pyridochlorin synthesis via cyclization of the metallated formylmethylimine

The differences in reactivity to acid of the nickel-complexed and metal-free meso-isocyanoporphyrins prompted the review of all previous attempts at synthesizing pyridochlorins, in order to be certain every logical cyclization method had been tried on both the metallated and metal-free substrates. The first cyclization that had been attempted, which gave rise to the iminoketone (93), rather than the desired α-pyridochlorin, had been performed only on the metal-free precursor (92). For the sake of completeness, further investigations using the metallated compound (M-92) were conducted.

Metallation of the formylmethylimine (92, see FIG. 3) was attempted under mild conditions, by stirring with zinc acetate at room temperature. However, this resulted in cleavage of the imine, to give the zinc amine (Zn-91). In light of this result, it was necessary to go back one step, to synthesize the zinc formylmethylimine by condensation of the zinc aminoporphyrin with glyoxal. The condensation occurred in better yield than that with the metal-free amine: after refluxing overnight approximately 80% of the desired product (Zn-92) was obtained. Test experiments were run using various acids to effect the cyclization of the zinc formylmethylimine, as initially it appeared to be more acid-stable than the metal-free analogue. Unfortunately, acetic acid, trifluoroacetic acid and boron trifluoride etherate all gave rise to the metal-free amine (91), and no evidence of cyclization was observed. Hence the standard cyclization conditions of Montmorillonite K10 acidic clay and refluxing toluene were employed. After 24 hours reflux mostly starting material remained, according to TLC, but there was a small amount of more polar green product, as well as some zinc iminoketone (Zn-93) (this cospotted with an authentic sample produced by metallating the iminoketone (93) with zinc). Refluxing was continued for a further 24 hours, then the mixture was worked up and purified by chromatography. The polar green material (Zn-123) was isolated in 10% yield, and 80% of the starting material was recovered. The visible spectrum of the new compound indicated it was a chlorin, with a prominent absorption peak at 678 nm. In contrast to the metal-free cyclic product (93), the $^1$H NMR spectrum of this product showed no ethylidene peaks, but a six hydrogen triplet at 0.33 ppm suggested that the cyclization had occurred as originally anticipated, to give an aromatic exocyclic pyridine ring and a gem-diethyl group at the adjacent β-position. There were four peaks in the aromatic region, evidence of three meso-hydrogens and one hydrogen on the exocyclic ring. This, coupled with the mass spectral data, showed that unlike in the benzochlorin synthesis, the hydroxyl group is retained on the ring. The exchangeable hydroxyl proton was not observed in the NMR spectrum, which had to be run in pyridine, as the compound was poorly soluble in other solvents. The new chlorin (Zn-123) was assigned the structure shown.

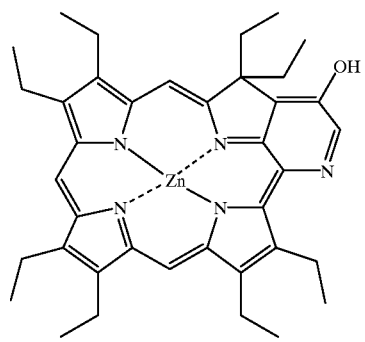

(Zn-123)

This compound was difficult to obtain in a completely pure state, as it streaked badly during chromatography. It was demetallated in dichloromethane/trifluoracetic acid to give the metal-free species (123) in approximately 30% yield. It seems likely that this poor yield is a reflection of the impurity of the starting material rather than a measure of the inefficiency of the demetallation. The metal-free compound (123) was easier to purify, as it is less polar and runs in a much narrower band on the silica column. It possesses a visible spectrum with a strong absorption at 672 nm; the diagnostic peaks in the $^1$H NMR spectrum are a six hydrogen triplet at 0.40 ppm and four aromatic peaks above 8 ppm, as well as a broad singlet at 3.06 ppm corresponding to the OH proton.

The synthesis of one of the target compounds had finally been achieved, using the very first method devised, but with one obviously crucial modification: using the metallated substrate for the cyclization rather than the free base. The (3-hydroxypyrido) chlorin (123) appears to be fairly stable to acid (in that it can be demetallated by treatment with acid without destruction of the chromophore), has good spectroscopic properties, and possesses sites for possible further derivation in its hydroxyl group and basic N-atom. Unfortunately, so far efforts to improve the yield have failed—approximately 5 mg product is obtained from 100 mg zinc formylmethylimine (Zn-92). However, the unused starting material is recovered unchanged, and can be recycled through the cyclization reaction many times.

Additional information concerning the synthesis of such compounds is as follows. Octaethylbenzochlorin is synthesized via intramolecular cyclization of the metallated meso-acrylaldehyde substituted porphyrin under acidic conditions. It seemed logical to follow a similar route to prepare octaethylpyridochlorin. Meso-aminooctaethylporphyrin 1 was condensed with glyoxal in THF/ethanol. After 24 hours refluxing the formylmethylimine product 2 was obtained in 69% yield. Intramolecular cyclization of 2 was achieved by overnight reflux in toluene in the presence of Montmorillonite K10 acidic clay. The two geometric isomers 3a and 3b were isolated in 31% total yield, in addition to a substantial quantity of the hydrolysis product, 1. The cyclic product consisted of a 4:1 mixture of the two isomers, which were separable by preparative chromatography. The major component was examined by NOE spectroscopy, which revealed it to be the Z-isomer 3a. The isomeric mixture was treated with acid, in an attempt to bring about a 1,2-dialkyl shift and hence form the desired pyridochlorin 4. However, this reaction was unsuccessful, leading to decomposition of the chromophore. Experiments intended to hydrogenate the ethylidene double bond of the isomeric mixture to give a single isomer also failed.

Scheme 1.
Synthesis of the isomeric chlorins 3a and 3b

OEPNH$_2$ →(i)→ OEPN=CHCHO →(ii)→
1             2

(i) CHCHO, THF/EtOH, Δ;
(ii) Montmorillonite K10, toluene, Δ

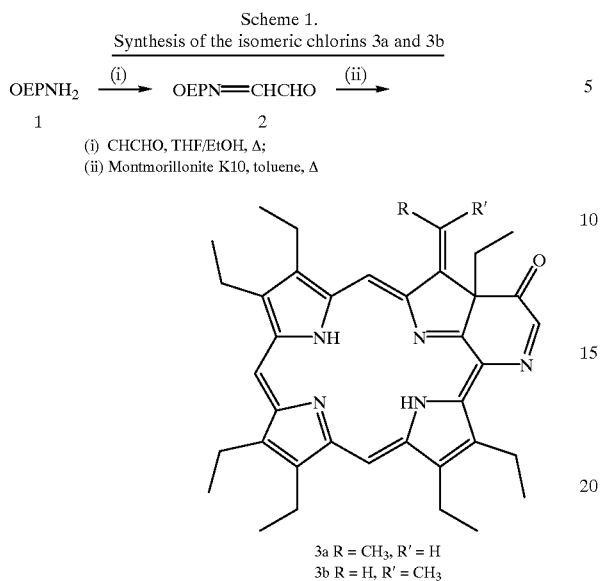

3a R = CH$_3$, R' = H
3b R = H, R' = CH$_3$

Scheme 1. Synthesis of the isomeric chlorins 3a and 3b

The presence or absence of a centrally-complexed metal can have a marked effect on the outcome of intramolecular cyclization reactions of porphyrins. Therefore the cyclization of the zinc complex of 2 was studied. Zn-2 was prepared by condensation of the zinc amninoporphyrin Zn-1 with glyoxal (metallation of 2 with zinc acetate led to hydrolysis of the imine, resulting in isolation of Zn-1). The cyclization was performed using the conditions described above (toluene, Montmorillonite K10, heat), and did indeed proceed differently to that of the free base 2. In this case, reaction was much slower, little change being discernable until refluxing had continued for 3 or 4 days. At this point only a trace amount of the expected product (the zinc complex of 3a/3b) was seen on TLC. A more polar green compound appeared to be the major product of the reaction (in addition to unreacted starting material, Zn-2, present as approximately 80% of the mixture). After work-up this compound was isolated in 20% yield and NMR analysis showed it to be the zinc complex of 4. Demetallation with trifluoroacetic acid gave the free base 4.

Scheme 2.
Synthesis of pyridochlorin 4

ZnOEPNH$_2$ →(i)→ ZnOEPN=CHCHO →(ii)→
Zn-1                Zn-2

(i) CHCHO, THF/EtOH, Δ;
(ii) Montmorillonite K10, toluene, Δ
(iii) TFA

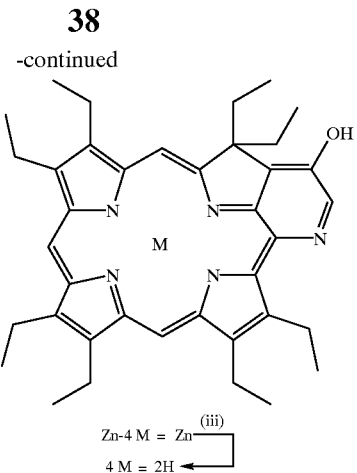

Zn-4 M = Zn —(iii)→
4 M = 2H ←

Scheme 2. Synthesis of pyridochlorin 4

Pyridochlorin 4 has a slightly red-shifted long-wavelength absorption ($\lambda_{max}$=672 nm), compared to octaethylbenzochlorin ($\lambda_{max}$=658 nm), and it possesses additional characteristics that might improve its performance as a photosensitizer over the latter. It is known that amphiphilic macrocycles, i.e., those bearing both hydrophobic and hydrophilic moieties display better tumour-localizing properties than photosensitizers without these properties. The presence of the polar hydroxypyridyl ring attached to the low polarity porphyrin skeleton increases the amphiphilicity of 4. Octaethylbenzochlorin suffers from a lack of functional groups available for further derivatization; the preparation of analogues based on this compound requires additional synthetic steps in order to introduce such a functionality. In contrast, chlorin 4 possesses "built-in" sites at the hydroxy-pyridine ring that allow for more direct analogue formation.

It will also be appreciated by those familiar with the art that the pyridinyl hydroxyl group such as shown for compound 4 directly above can be replaced by hydrogen under appropriate conditions, thereby providing an additional pathway to compounds containing a simple (unsubstituted) pyridine ring as exocyclic component.

3a: $^1$H NMR (CDCl$_3$) δ: -1.78 (br s, 1H, NH), -0.74 (br s, 1H, NH), 0.50 (t, J=7.3 Hz, 3H, CH$_3$), 1.65–1.90 (m, 18H, 6CH$_3$), 2.81 (d, J=7.6 Hz, 3H, CH$_3$=CH), 3.70–4.00 (m, 12H, 6CH$_2$), 4.09–4.26 (m, 2H, CH$_2$), 7.45 (q, J=7.5 Hz, 1H, CH=CH$_3$), 8.15 (s, 1H, CH=N), 9.31, 9.51, 9.57 (3s, 3H, meso-H's); UV-Vis in CHCH$_3$, λ nm (ε): 360 (4.33), 410 (4.82), 446 (4.67), 584 (3.66), 672 (3.79), 722 (4.03); Analysis calc'd for C$_{38}$H$_{45}$N$_5$O.H$_2$O: C, 75.34; H, 7.82; N, 11.56: found C, 74.89; H, 7.69; N, 11.15.

3b: $^1$H NMR (CDCl$_3$) δ: -1.14 (br s, 1H, NH), -0.74 (br s, 1H, NH), 0.10 (t, J=7.3 Hz, 3H, CH$_3$), 1.68–1.84 (m, 18H, 6CH$_3$), 2.62 (d, J=7.5 Hz, 3H, CH$_3$=CH), 3.70–3.95 (m, 12H, 6CH$_2$), 4.04–4.25 (m, 2H, CH$_2$), 7.72 (q, J=7.5 Hz, 1H, CH=CH$_3$), 7.98 (s, 1H, CH=N), 9.16, 9.43, 9.53 (3s, 3H, meso-H's).

4: $^1$H NMR (pyridine-d$_5$) δ: 0.40 (t, J=7.3 Hz, 6H, 2CH$_3$), 1.63–1.81 (m, 15H, 5CH$_3$), 1.88 (t, J=7.3 Hz, 3H, CH$_3$), 2.78–2.91 (m, 2H, CH$_2$), 3.49–3.71 (m, 10H, 5CH$_2$), 3.85 (q, J=7.5 Hz, 2H, CH$_2$), 4.43 (q, J=7.3 Hz, 2H, CH$_2$), 8.40, 8.99, 9.58, 9.69 (4s, 4H, 3meso-H's and CH=N) 13.06 (br s, 1H, OH); UV-Vis in CHCH$_3$, λ nm (ε): 412 (4.89), 490 (3.51), 522 (3.73), 556 (3.75), 616 (3.86), 672 (4.36); Analysis calc'd for C$_{38}$H$_{47}$N$_5$O.0.5H$_2$O: C, 76.22; H, 8.08; N, 11.70: found C, 75.96; H, 7.64; N, 11.67.

Example 5
Preparation and Characterization of Compounds

Presented below are details on the synthesis and characterization of compounds used in the practice of the invention. In summary, these Examples have described efforts to synthesize a number of chlorins with fused pyridine rings, analogous to the benzochlorins. Varying yields were achieved, with one of the preferred target molecules being prepared, while three other new types of cyclic chlorin were created.

The first new chlorin that was prepared, (93), possesses an exocyclic ring containing a β-carbonylimine functionality O=CCH=N, and an ethylidene group on the reduced pyrrole ring. Its longest-wavelength absorption in the visible spectrum is at 722 run ($\epsilon$=10800). Both possible geometric isomers were produced, in a ratio of approximately 4: 1, and these two isomers could be separated by chromatography, although they were not amenable to catalytic hydrogenation to give a single isomer. The carbonyl group could be reduced with sodium borohydride to give the corresponding alcohol. Attempts to aromatize ring were unsuccessful. This compound could be metallated with nickel or zinc under standard conditions.

The second type of chlorin synthesized, (108), contains an exocyclic lactam, with an absorption at 686 nm ($\epsilon$=34800). Again, an ethylidene group is attached to the reduced pyrrole ring, but in this case the ratio of geometric isomers is 1:1, and these proved substantially inseparable by chromatography. The metal complexes of this compound appear to exist in solution as aggregates, indicating the high affinity of the centrally complexed metal for the lactam amide fumctionality of another molecule. Reduction of the amide group failed, but the ethylidene group underwent catalytic hydrogenation to give a single diastereomer. Metallation and demetallation reactions were successful.

The third class of compounds formed, (120), consists of a dimer of two chlorin molecules possessing exocyclic pyridine rings, fused to each other through the pyridine rings. These compounds display very unusual visible spectra, for example, the nickel complex possesses an absorption peak at 814 nm ($\epsilon$=13600). The X-ray crystal structure shows that the molecule is essentially planar. Metallation and demetallation reaction were successful.

The fourth and final class of compounds synthesized, (123), contains an exocyclic 3-hydroxypyridine ring, with the pyridine N-atom positioned α to the porphyrin meso-position. The metal-free species has a visible spectrum with its longest-wavelength absorption at 672 nm ($\epsilon$=22700).

Preparation and characterization of compounds
(92) 5-Formylmethyliminooctaethylporphyrin

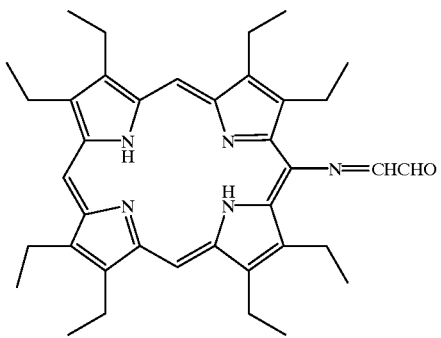

5-Aminooctaethylporphyrin (91)[194] (100 mg, 0.18 mmol) was dissolved in dry THF (10 mL). Glyoxal trimer dihydrate (250 mg, 1.2 mmol) was dissolved in ethanol (10 mL) with heating. The latter solution was added to the former, and the mixture was refluxed overnight. The solvent was removed in vacuo and the residue purified by chromatography (flash silica, dichloromethane eluent, polarity of eluent increased to 5% ethyl acetate in dichloromethane after the product had been eluted to elute-starting material), giving the product (74 mg, 69%) and unreacted starting material (24 mg).

$^1$H NMR (200 MHz, CDCl$_3$)δ 1.80 (t, J=7 Hz, 6H, 2× CH$_3$), 1.88–2.12 (m, 18H, 6× CH$_3$), 3.92–4.26 (m, 16H, 8× CH$_2$), 7.84 (d, J=9 Hz, 1H, C̲HCHO), 9.95 (s, 1H, 1 meso-H), 10.11 (s, 2H, 2 meso-H's), 10.45 (d, J=9 Hz, 1H, CHO); $^{13}$C NMR (50 MHz, CDCl$_3$) δ 16.21 18.45. 18.51, 19.77, 22.15, 96.69, 98.19. 102.62, 128.26, 137.18. 140.30. 141.53. 142.36, 143.67, 143.89. 145.73, 169.16. 191.46: UV-Vis (CHCl$_3$ (log $\epsilon$)) $\lambda_{max}$ 396 (4.96), 458 (4.67), 502 (3.98), 582 (3.91), 660 (3.64) nm; MS (EI) m/e 589 (M$^+$, 100%), 560 (M$^+$-29, 32%).

(93) Cyclic iminoketone (diastereomeric mixture)

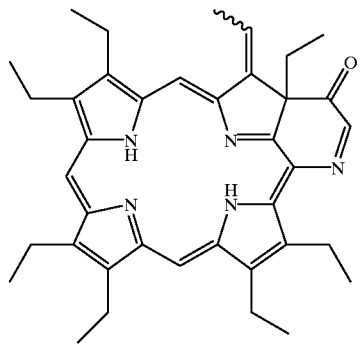

The formylmethylimine (92) (61 mg, 0.10 mmol) was dissolved in toluene (10 mL). Montnorillonite K10 acidic clay (50 mg) was activated by heating with a heat-gun in a test tube for 5 min, until all water had been driven off, and was then added to the solution. The mixture was refluxed overnight, then filtered and the solvent was removed in vacuo. The residue was purified by chromatography (silica, dichloromethane eluent) to give the cyclized product (19 mg, 31%) as 2 diastereomers and unreacted starting material (14 mg). The 2 isomers were separated by prep. TLC on a 0.5 mm thick silica plate, eluting with dichloromethane:hexanes 1:1. UV-Vis (CHCl$_3$ (log $\epsilon$)) $\lambda_{max}$ 360 (4.33), 410 (4.82), 446 (4.67), 584 (3.66), 672 (3.79), 722 (4.03) nm; MS (EI) m/e calc'd for C$_{38}$H$_{45}$N$_5$O: 587.36243, found 587.36313; 587 (M$^+$, 40%), 558 (M$^+$-29, 100%); Singlet Oxygen Test: Negative.

(93a) Cyclic iminoketone (major isomer)
Present as approximately 80% of the mixture.
m.p. 214–215° C.; R$_F$ 0.36 (silica—CH$_2$Cl$_2$:hexanes 1:1); $^1$H NMR (400 MHz, CDCl$_3$) δ -1.18 (br s, 1H, 1× NH), -0.74 (br s, 1H, 1× NH), 0.50 (t, J=7.3 Hz, 3H, CH$_3$ of angular ethyl group), 1.65–1.90 (m, 18H, 6× CH$_3$), 2.81 (d, J=7.6 Hz, 3H, C̲H$_3$CH=), 3.70–4.00 (m. 12H. 6× CH$_2$), 4.09–4.26 (m. 2H. CH$_2$ of angular ethyl group), 7.45 (q, J=7.5 Hz, 1H. C̲HCH$_3$), 8.15 (s, 1H, C̲H=N), 9.31 (s, 1H, 1 meso-H), 9.51 (s, 1H, 1 meso-H), 9.57 (s, 1H, 1 meso-H); Analysis calc'd for C$_{38}$H$_{45}$N$_5$O.H$_2$O: C, 75.34; H, 7.82; N, 11.56; found: C, 74.89; H. 7.69; N, 11.15.

(93b) Cyclic iminoketone (minor isomer)
Present as approximately 20% of the mixture.
R$_F$ 0.27 (silica—CH$_2$Cl$_2$: hexanes 1:1); $^1$H NMR (400 MHz, CDCl$_3$) δ -1.14 (br s, 1H, 1× NH), -0.74 (br s, 1H, 1× NH), 0.10 (t, J=7.3 Hz, 3H, CH$_3$ of angular ethyl group), 1.68–1.84 (m, 18H, 6× CH$_3$), 2.62 (d, J=7.5 Hz, 3H, C$\underline{H}_3$=CH), 3.70–3.95 (m, 12H, 6× CH$_2$), 4.05–4.25 (m, 2H, CH$_2$ of angular ethyl group), 7.72 (q, J=7.5 Hz, 1H, CH$_3$=C$\underline{H}$), 7.98 (s, 1H, CH=N), 9.16 (s, 1H, 1 meso-H), 9.43 (s, 1H, 1 meso-H), 9.53 (s, 1H, 1 meso-H).

(Zn-93) Cyclic iminoketone-zinc (II) (diastereomeric mixture)

The cyclic product (93) (6 mg, 0.010 mmol) was dissolved in dichloromethane (1 mL), and zinc acetate dihydrate (10 mg, 0.046 mmol) in methanol (0.5 mL) was added. The mixture was refluxed 2 hours, then the solvent was removed in vacuo and the residue purified by chromatography (silica, dichloromethane eluent) to give the metallated product (4 mg, 62% yield).

R$_F$ 0.64 (silica—CH$_2$Cl$_2$); $^1$H NMR (200 MHz, CDCl$_3$) (NB: only peaks for major isomer listed) δ 0.50 (t, J=7.5 Hz, 3H, CH$_3$ of angular ethyl group), 1.51–1.75 (m, 18H, 6× CH$_3$), 2.70 (d, J=7.5 Hz, 3H, C$\underline{H}_3$CH=), 3.49–3.75 (m, 12H, 6× CH$_2$), 3.80–3.97 (m, 2H, CH$_2$ of angular ethyl group), 7.35 (q, J=7.5 Hz, 1H, C$\underline{H}$CH$_3$), 7.95 (s, 1H, C$\underline{H}$=N), 8.85 (s, 1H, 1 meso-H), 9.05 (s, 1H, 1 meso-H), 9.13 (s, 1H, 1 meso-H); UV-Vis (CH$_2$Cl$_2$) λ$_{max}$ 412, 454, 688 nm.

(94) Cyclic iminoalcohol (diastereomeric mixture

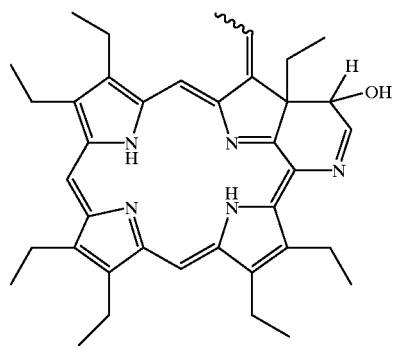

The cyclic product (93) (8 mg, 0.013 mmol) was dissolved in dichloromethane (5 mL). Sodium borohydride (10 mg, 0.26 mmol) in ethanol (0.5 mL) was added, and the mixture was stirred at room temperature for 1 hour. The mixture was then poured into water and extracted with dichloromethane. After work-up, the residue was purified by prep. TLC (0.2 mm thickness silica plate, dichloromethane eluent) to give the product, present as a mixture of diastereomers (2 mg, 25% yield).

$^1$H NMR (400 MHz, CDCl$_3$) (NB: only peaks for major isomer listed) δ –2.25 (br s, 1H, 1× NH), –1.69 (br s, 1H, 1× NH), –0.23 (t, J=7.4 Hz, 3H, CH$_3$ of angular ethyl group), 1.50–2.00 (m, 18H, 6× CH$_3$), 2.63 (d, J=7.5 Hz, 3H, C$\underline{H}_3$CH=), 3.70–4.40 (m, 14H, 7× CH$_2$), 4.50 (s, 1H, C$\underline{H}$OH), 6.62 (q, J=7.4 Hz, 1H, C$\underline{H}$CH$_3$), 7.88 (s, 1H, C$\underline{H}$=N), 9.42 (s, 1H, 1 meso-H), 9.64 (s, 1H, 1 meso-H), 9.71 (s, 1H, 1 meso-H); MS (EI) m/e 589 (M$^+$, 50%), 587 (M$^+$-2, 45%), 560 (M$^+$-29, 75%), 558 (M$^+$-31, 100%); Singlet Oxygen Test: Positive.

(105) 5-Arlninocarbonyloctaethylporphyrin

Prepared according to the method of Clezy et al.[207]

m.p. 296–299° C. (lit.295–297); R$_F$ 0.32 (silica—CH$_2$Cl$_2$/5% AcOEt); UV-Vis (CH$_2$Cl$_2$) λ$_{max}$ 400, 502, 536, 572, 624 nm.

(106) 5-((N-Hydroxymethyl)aminocarbonyl)octaethylporphyrin

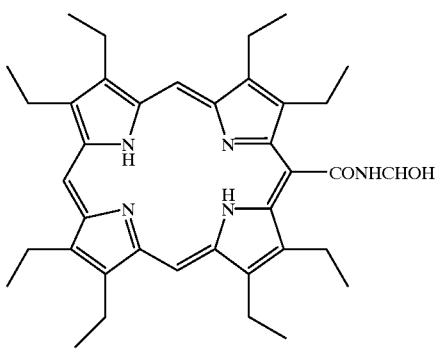

The amide (105) (28 mg, 0.048 mmol) was dissolved in dry THF (10 mL) under nitrogen. 1.6 M n-BuLi in hexanes (30 μL, 0.048 mmol) was added, and the mixture was stirred under nitrogen for 5 min. Paraformaldehyde (3 mg) was added, and the mixture was stirred at room temperature for 1 hour. Acetic acid (2 drops) was added, then the solvent was removed in vacuo and the residue was purified by chromatography (flash silica, eluent 5% ethyl acetate in dichloromethane), to give unreacted starting material (6 mg) and the product (15 mg, 51% yield).

m.p. >300° C. R$_F$ 0.16 (silica—CH$_2$Cl$_2$/5% AcOEt); $^1$H NMR (200 MHz, CDCl$_3$) δ –3.50 (v br s, 2H, 2× NH), 1.33 (t, J=7.5 Hz, 6H, 2× CH$_3$), 1.78–1.94 (m, 18H, 6× CH$_3$), 3.44–3.62 (m, 4H, 2× CH$_2$), 3.84–4.12 (m, 12H, 6× CH$_2$), 4.42 (d, J=6 Hz, 2H, C$\underline{H}_2$OH), 6.50 (t, J=6 Hz, 1H, NH), 9.88 (s, 1H, 1 meso-H), 10.10 (s, 2H, 2 meso-H's); $^{13}$C NMR (50 MHz, CDCl$_3$) δ 17.55, 18.47, 19.57, 20.30, 65.18, 96.33, 97.02, 102.83, 110.80, 140.73, 141.48, 142.09, 142.25, 143.13, 144.58, 145.32, 172.10; UV-Vis (CH$_2$Cl$_2$) λ$_{max}$ 400, 502, 536, 570, 624 nm; MS (FAB (thioglycerol matrix)) m/e 608 (M$^+$, 100%).

(Ni-105) (5-Aminocarbonyloctaethylporphyrinato)nickel (II)

The amide (105) (31 mg, 0.054 mmol) was dissolved in dimethylformamide (5 mL) and nickel acetate tetrahydrate (30 mg, 0.12 mmol) was added. The mixture was refluxed overnight, then poured into water, extracted with ethyl acetate, the extracts dried over sodium sulfate, and the solvent removed in vacuo. The residue was purified by flash chromatography (silica, eluent 5% ethyl acetate in dichloromethane) to give the metallated product (28 mg, 82% yield).

m.p. 272–274° C. R$_F$ 0.44 (silica—CH$_2$Cl$_2$/5% AcOEt); $^1$H NMR (200 MHz, CDCl$_3$) δ 1.60 (t. J=7.5 Hz, 6H, 2Δ CH$_3$), 1.77 (t. J=7.5 Hz, 18H. 6× CH$_3$), 3.73–3.99 (m. 16H. 8× CH$_2$), 5.75 (br d, J=2 Hz, 1H, 1× NH), 6.38 (br d. J=2 Hz, 1H, 1× NH), 9.52 (s, 1H, 1 meso-H), 9.60 (s, 2H, 2 meso-H's); $^{13}$C NMR (50 MHz, CDCl$_3$) δ 18.02, 18.17, 19.58, 21.21, 96.36, 96.86, 139.24, 140.10, 140.81, 143.25, 143.47, 143.69, 145.61, 172.50, UV-Vis (CH$_2$Cl$_2$) λ$_{max}$ 400, 524, 558 nm; MS (FAB (thioglycerol+CHCl$_3$ matrix)) m/e 634 (M$^+$, 100%).

(Ni-106) [5-((N-Hydroxymethyl)aminocarbonyl)octaethylporphyrinato]nickel(I)

The nickel amide (Ni-105) (30 mg, 0.047 mmol) was dissolved in dry THF (20 mL) and 1.6 M n-BuLi in hexanes (15 μL, 0.024 mmol) was added. This solution was stirred for 5 min under nitrogen, then paraformaldehyde (4 mg) was added. The mixture was stirred at room temperature for 1 hour, then acetic acid (2 drops) was added and the solvent evaporated. The residue was purified by chromatography (silica, eluent 5% ethyl acetate in dichloromethane) to give the pink product (24 mg, 76% yield).

$R_F$ 0.25 (silica—CH$_2$Cl$_2$/5% AcOEt); $^1$H NMR (200 MHz, CDCl$_3$) δ 1.50 (t, J=7.5 Hz, 6H, 2× CH$_3$), 1.68–1.85 (m, 18H, 6× CH$_3$), 3.61–3.92 (m, 16H, 8× CH$_2$), 5.08 (d, J=6.0 Hz, 2H, CH$_2$OH), 6.58 (t, J=6.0 Hz, 1H, NH), 9.48 (s, 1H, 1 meso-H), 9.53 (s, 2H, 2 meso-H's); $^{13}$C NMR (50 MHz, CDCl$_3$) δ 17.74, 18.09, 18.17, 19.54, 20.84, 65.67, 96.47, 96.88, 108.99, 135.29, 140.10, 140.77, 143.22, 143.39, 143.46, 145.51, 171.77; UV-Vis (CH$_2$Cl$_2$) λ$_{max}$ 398, 522, 558 nm; MS (FAB (thioglycerol+CHCl$_3$ matrix)) m/e 663 (M$^+$, 30%).

(109) 5-(N-Formylaminocarbonyl)octaethylporphyrin

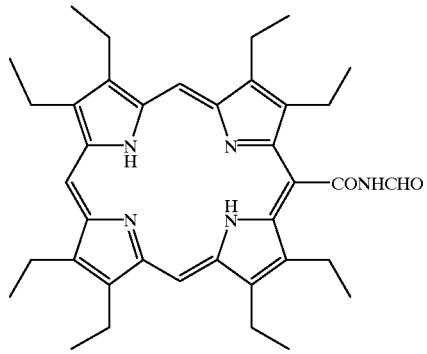

The N-hydroxymethylamide (106) (5 mg, 0.008 mmol) was dissolved in dichloromethane (2 mL) to which anhydrous magnesium sulfate (10 mg) had been added. To this mixture was added N-methylmorpholine-N-oxide (1 mg), and the solution was stirred for 5 min. Then tetrapropylammonium perruthenate (TPAP) (0.5 mg) was added and the mixture was stirred for 30 min. The solvent was evaporated, and the residue purified by chromatography (silica, eluent dichloromethane) to give the pink product (4 mg, 80% yield).

$R_F$ 0.29 (silica—CH$_2$Cl$_2$); UV-Vis (CH$_2$Cl$_2$) λ$_{max}$ 402, 504, 538, 572, 624 nm; MS (FAB (thioglycerol matrix)) m/e 606 (M$^+$, 100%).

(Ni-109) [5-(N-Formylaminocarbonyl)octaethylporphyrinato]nickel(II).

The nickel N-hydroxymethylamide (Ni-106) (11 mg, 0.017 mmol) was dissolved in dichloromethane (2 mL) to which anhydrous magnesium sulfate (20 mg) was added. To this solution was added N-methylmorpholine-N-oxide (2 mg). The mixture was stirred for 5 min, then tetrapropylammonium perruthenate (TPAP) (0.5 mg) was added. The mixture was stirred for 30 min, then the solvent was evaporated, and the residue purified by chromatography (silica, dichloromethane eluent) to give the pink product (7 mg, 64% yield).

$R_F$ 0.43 (silica—CH$_2$Cl$_2$); UV-Vis (CH$_2$Cl$_2$) λ$_{max}$ 398, 524, 560 nm; MS (FAB (thioglycerol+CHCl$_3$)) m/e 662 (M$^+$+1, 85%).

(Ni-107) [5-((N-Hydroxymethylmethylether)aminocarbonyl)octaethylporphyrinato]nickel-(II)

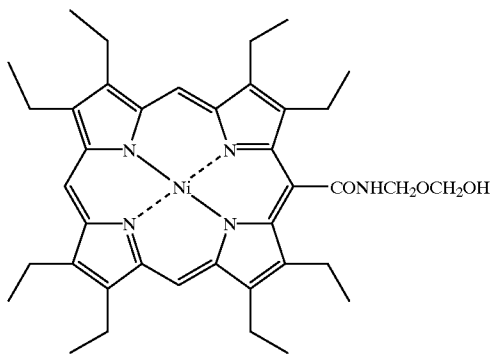

Formed as a side-product in the synthesis of (Ni-106), especially when excesses of butyllithium were used.
$^1$H NMvR (200 MHz, CDCl$_3$) δ 1.58 (t, J=7.5 Hz, 6H, 2× CH$_3$), 1.70–1.88 (m, 18H, 6× CH$_3$), 3.62–3.99 (m, 19H. 8× CH$_2$+OCH$_2$O+NH), 5.46 (d, J=8 Hz, 2H, NHCH$_2$O), 9.58 (s, 1H, 1 meso-H), 9.64 (s, 2H, 2 meso-H's); MS (FAB (thioglycerol+CHCl$_3$ matrix)) m/e 693 (M$^+$, 16%).
(108) Unsaturated lactam (mixture of isomers)

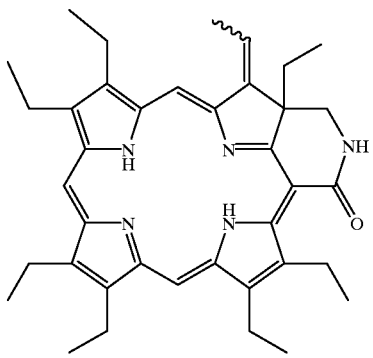

The nickel N-hydroxymethylamide (Ni-106) (10 mg, 0.015 mmol) was dissolved in concentrated sulfuric acid (1 mL), and stirred at room temperature for 1.5 hours. The solution was then poured into water, extracted 4 times with dichloromethane, washed successively with potassium carbonate solution and water, and the solvent evaporated. The residue was purified by chromatography (silica, eluent 20% ethyl acetate in dichloromethane) to give the green-brown product as a 1:1 mixture of isomers (7 mg, 79% yield).

m.p. 293–294° C.; $R_F$ 0.44 (silica—CH$_2$Cl$_2$/20% AcOEt); $^1$H NMR (400 MHz, CDCl$_3$) δ (selected peaks), -1.20 (br s, 2H, 2× NH of one isomer), -0.62 (br s, 2H, 2× NH of one isomer), 0.33 (t, 3H, Me of angular Et group of one isomer), 0.58 (t, 3H, Me of angular Et group of one isomer), 2.37 (d, 3H, CH$_3$=CH of one isomer), 2.60 (d, 3H, CH$_3$=CH of one isomer), 6.10 (q, 1H, CH=CH$_3$ of one isomer), 6.66 (d, 1H, NH of one isomer), 6.73 (d, 1H, NH of one isomer), 7.17 (q, 1H, CH=CH$_3$ of one isomer), 8.86, 9.10, 9.39, 9.47, 9.60, 9.62 (6s. 6H, 6 meso-H's); UV-Vis (CH$_2$Cl$_2$ (log ε)) λ$_{max}$ 414 (5.15), 506 (3.95), 542 (3.57). 628 (3.57), 680 (4.53), 686 (4.54) nm; MS (EI) m/e calc'd for C$_{38}$H$_{47}$N$_5$O: 589.37805. found 589.37825; 589 (M$^+$, 100%); Analysis calc'd for C$_{38}$H$_{47}$N$_5$O: C, 77.38; H, 8.03; N, 11.87; found: C, 77.10; H, 7.96; N, 11.59; Singlet Oxygen Test: Positive.
(Ni-108) Nickel unsaturated lactam (mixture of isomers)
The nickel N-hydroxymethylamide (Ni-106) (14 mg, 0.021 mmol) was dissolved in dichloromethane (5 mL) and boron trifluoride etherate (1 drop) was added. The colour changed from grey-green to bright green almost immediately. The solution was stirred for 3 hours, then the solvent was evaporated and the residue purified by chromatography (silica, eluent 10% ethyl acetate in dichloromethane) to give 4 mg pure less polar isomer and 8 mg of a mixture of the two isomers.

$R_F$ 0.18 and 0.08 (silica—$CH_2Cl_2$/5% AcOEt); UV-Vis ($CH_2Cl_2$) $\lambda_{max}$ 414,506,562, 644 nm; MS (EI) m/645 ($M^+$, 100%), 616 ($M^+$–29, 61%).

(111) Lactam reduction product

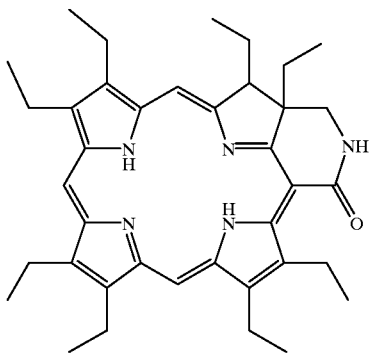

The lactam (108) (5 mg, 0.008 mmol) was dissolved in THF (3 mL) and triethylamine (1 drop). 10% Pd on charcoal (2 mg) was added and the mixture was stirred overnight under a hydrogen balloon. The catalyst was filtered off and air was bubbled through the solution for 1 hour. The THF was evaporated and the residue purified by chromatography (silica, eluent 20% ethyl acetate in dichloromethane) to give the desired product as a dark green solid (2.5 mg, 50% yield).

m.p. >300° C.: $R_F$ 0.44 (silica—$CH_2Cl_2$/20% AcOEt), $^1$H NMR (400 MHz, $CDCl_3$) δ –0.66 (br s, 2H, 2× NH), –0.22 (t, J=7.5 Hz, 3H, $CH_3$ of angular ethyl group), 1.47–2.10 (m, 21H, 7× $CH_3$), 2.60–2.75 (m, 1H, CH of angular ethyl group), 3.04–3.20 (m, 1H, CH of angular ethyl group), 3.50–4.00 (m, 13H), 4.05–4.25 (m, 3H), 4.63 (dd, J=12.5, 2.0 Hz, 1H, angular H), 6.70 (d, J=5.22 Hz, 1H, NH), 8.47 (s, 1H, 1 meso-H), 9.38 (s, 1H, 1 meso-H), 9.57 (s, 1H, 1 meso-H); UV-Vis ($CHCl_3$ (log ε)) $\lambda_{max}$ 406 (5.19), 502 (4.04), 534 (3.61), 670 (4.64) nm; MS (EI) m/e calc'd for $C_{38}H_{49}N_5O$: 591.39374, found 591.39285; 591 ($M^+$, 100%).

(113) 5-Formamidooctaethylporphyrin

This compound was prepared in 87% yield according to the procedure of Clezy et al.$^{207}$ m.p. 231–234° C.; $R_F$ 0.14 (silica—$CH_2Cl_2$); $^1$H NMR (200 MHz, $CDCl_3$) δ –3.43 (br s, 2H, 2× NH), 1.70 (t, J=8 Hz, 6H, 2× $CH_3$), 1.80–2.01 (m, 18H, 6× $CH_3$), 3.95–4.22 (m, 16H, 8× $CH_2$), 8.61 (d, J=12 Hz, 1H, CHO), 9.36 (br d, J=12 Hz, 1H, NH), 10.02 (s, 1H, 1 meso-H), 10.18 (s, 2H, 2 meso-H's); $^{13}$C NMR (50 MHz, $CDCl_3$) δ 17.50, 18.55, 19.82, 21.77, 96.84, 97.48, 102.81, 109.07, 140.57, 141.82, 142.55, 143.55, 143.75, 144.51, 145.74, 167.82; UV-Vis ($CH_2Cl_2$) $\lambda_{max}$ 404, 504, 538, 572, 626 nm.

(112) 5-Isocyanooctaethylporphyrin

The formamide (113) (23 mg, 0.04 mmol) was dissolved in dry pyridine (5 mL). Phosphoryl chloride (200 μL, 2.1 mmol) was added dropwise under nitrogen, and the mixture was stirred under nitrogen at 40° C. for 2 hours. The solvent was removed in vacuo, and the residue purified by chromatography (flash silica, dichloromethane eluent) to give the product (20 mg, 90%).

m.p. 257–259° C.; RF 0.39 (silica—1:1 $CH_2Cl_2$:hexanes); $^1$H NMR (200 MHz, $CDCl_3$) δ –3.41 (v br s, 2H, 2× NH), 1.82–2.00 (m, 24H, 8× $CH_3$), 3.95–4.17 (m, 12H, 6× $CH_2$), 4.28 (q. J=8 Hz, 4H, 2× $CH_2$), 10.01 (s, 1H, 1 meso-H), 10.14 (s, 2H, 2 meso-H's), $^{13}$C. NMR (50 MHz, $CDCl_3$) δ 17.22, 18.48. 19.70, 21.60, 97.96, 102.83, 114.30, 140.56, 141.01, 141.46, 141.92, 142.45, 143.76. 144.86, 145.38. 175.30; UV-Vis ($CH_2Cl_2$) $\lambda_{max}$ 408, 510, 546, 580, 634 nm.

(116) 5-(C-Hydroxymethylformamido)octaethylporphyrin

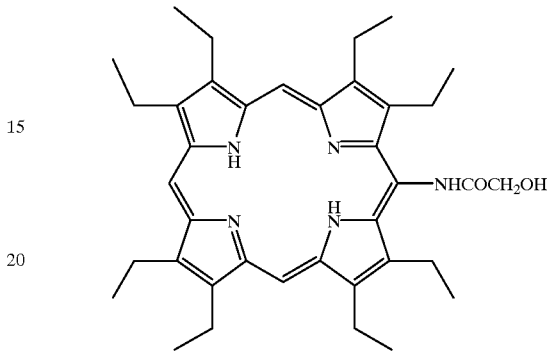

Paraformaldehyde (100 mg) was placed in a 25 mL flask equipped with a septum. Toluene (5 mL) was placed in another 25 mL flask equipped with a septum and a stir bar. The 2 flasks were connected by a canula and the flask containing toluene was also furnished with an empty balloon. The paraformaldehyde-containing flask was heated with a heat-gun and the resultant gaseous formaldehyde was bubbled through the toluene. The heating was continued for 5 min. after which the canula was removed, and the balloon filled with nitrogen. Boron trifluoride etherate (30 μL) was added dropwise by syringe and the mixture was stirred for 5 min. The isocyanoporphyrin (112) (17 mg, 0.030 mmol) was added to the reaction mixture and stirring continued under nitrogen for 30 min. The mixture was poured into water, extracted with dichloromethane, the extracts dried over sodium sulfate and the solvent evaporated in vacuo. The residue was purified by flash chromatography (silica, eluent 5% ethyl acetate in dichloromethane) to give the polar pink product (5 mg, 28% yield).

m.p. 272–280° C.; $R_F$ 0.09 (silica—$CH_2Cl_2$/5% AcOEt); $^1$H NMR (200 MHz, $CDCl_3$+1 drop TFA) δ 1.12 (t, J=7.5 Hz, 6H, 2× $CH_3$), 1.39 (t, J=7.5 Hz, 6H, 2× $CH_3$), 1.60–1.80 (m, 12H, 4× $CH_3$), 3.39–3.68 (m, 4H, 2× $CH_2$), 3.79 (q, J=7.5 Hz, 4H, 2× $CH_2$), 3.98 (q, J=7.5 Hz, 8H, 4× $CH_2$), 4.76 (s, 2H, $\underline{CH_2}$OH), 10.10 (s, 1H, 1 meso-H), 10.26 (s, 2H, 2 meso-H's); UV-Vis ($CH_2Cl_2$) $\lambda_{max}$ 404, 504, 538, 572, 624 nm; MS (EI) m/e 607 ($M^+$, 100%), 576 ($M^+$–$CH_2$OH, 72%).

(Ni-116) [5-(C-Hydroxymethylformamido) octaethylporphyrinato]nickel(II)

The C-hydroxymethylformamide (116) (5 ma. 0.008 mmol) was dissolved in dimethylformamide (1 mL) and nickel acetate tetrahydrate (30 mg, 0.12 mmol) was added. The mixture was refluxed for 2 hours, then poured into water, extracted with ethyl acetate, washed with water, dried over sodium sulfate and the solvent removed in vacuo. The residue was purified by flash chromatography (silica, eluent 5% ethyl acetate in dichloromethane) to give the product (4 mg, 73% yield).

$R_F$ 0.23 (silica—$CH_2Cl_2$/10% AcOEt); UV-Vis ($CH_2Cl_2$) $\lambda_{max}$ 402, 526, 562 nm; MS (EI) m/e 663 ($M^+$, 100%).

(Ni-113) [5-Formamidooctaethylporphyrinato]nickel(II)

The formamide (113) (32 mg, 0.055 mmol) was dissolved in DMF (5 mL), and nickel acetate tetrahydrate (20 mg, 0.080 mmol) was added. The mixture was refluxed for 1 hour, then allowed to cool, poured into water, and extracted 3 times with ethyl acetate. The organic phase was dried, the solvent was evaporated, and the residue was purified by chromatography (silica, eluent 5% ethyl acetate in dichloromethane), to give the metallated product (27 mg, 77% yield).

m.p. 264–267° C.; $R_F$ 0.27 (silica—$CH_2Cl_2$); $^1H$ NMR (200 MHz, $CDCl_3$) δ 1.61–1.86 (m, 24H, 8× $CH_3$), 3.82 (q, J=7.5 Hz, 16H, 8× $CH_2$), 7.68 (d, J=;2 Hz, 1H, CHO), 9.13 (br d, J=12 Hz, 1H, NH), 9.51 (s, 1H, 1 meso-H), 9.55 (s, 2H, 2 meso-H's); $^{13}C$ NMR (50 MHz, $CDCl_3$) δ 17.42, 18.16, 18.21, 18.26, 19.51, 19.62, 22.04, 96.75, 97.25, 107.44, 138.32, 139.20, 140.31, 141.05, 142.80, 143.60, 143.76, 145.72, 167.60; UV-Vis ($CH_2Cl_2$) $\lambda_{max}$ 400, 524, 562 nm.

(Ni-112) (5-Isocyanooctaethylporphyrinato)nickel(II)

The nickel formamide (Ni-113) (22 mg, 0.035 mmol) was dissolved in pyridine (2 mL), and phosphoryl chloride (4 drops) was added to this solution. The mixture was stirred at room temperature for 30 min. then was added to water and the resulting solid was filtered off and washed with water, to give quantitative product.

m.p. 282–284° C.; $R_F$ 0.53 (silica—1:1 $CH_2Cl_2$:hexanes); $^1H$ NMR (200 MHz, $CDCl_3$) δ 1.58–1.83 (m, 24H, 8× $CH_3$), 3.62–3.83 (m, 12H, 6× $CH_2$), 3.99 (q, J=7.5 Hz, 4H, 2× $CH_2$), 9.38 (s, 1H, 1 meso-H), 9.41 (s, 2H, 2 meso-H's); $^{13}C$ NMR (50 MHz, $CDCl_3$) δ 17.31, 18.27, 20.48, 22.08, 97.63, 97.79, 102.86, 136.10, 138.36, 140.78, 143.27, 143.59, 144.06, 146.12; UV-Vis ($CH_2Cl_2$) $\lambda_{max}$ 406, 536, 576 nm.

(120) Nickel dimer

The nickel isocyanide (Ni-112) (25 mg, 0.039 mmol) was dissolved in dichloromethane (3 mL), and boron trifluoride etherate (25 μL) was added. The mixture was stirred overnight, then pyridine (1 drop) was added and the solvent was evaporated. The residue was purified by chromatography (silica, eluent dichloromethane:hexanes 1:1), then suspended in methanol and filtered, to give the green solid product (14 mg, 56% yield).

m.p. >300° C.; $R_F$ 0.64 (silica—1:1 $CH_2Cl_2$:hexanes); $^1H$ NMR (400 MHz, $CDCl_3$) δ 0.05 (t, J=7.5 Hz, 12H, 4× $CH_3$ of gem-diEt), 1.40–1.60 (m, 36H, 12× $CH_3$), 2.64–2.76 (m, 4H, 2× $CH_2$), 3.10–3.30 (m, 16H, 8× $CH_2$), 3.42 (q, J=7.5 Hz, 4H, 2× $CH_2$), 3.64–3.76 (m, 4H, 2× $CH_2$), 4.17 (q, J=7.3 Hz, 4H, 2× $CH_2$), 7.64 (br s, 2H, 2 meso-H's), 7.96 (s, 2H, 2 meso-H's), 8.49 (br s, 2H, 2 meso-H's); UV-Vis ($CHCl_3$ (log ε)) $\lambda_{max}$ 408 (4.69), 500 (4.99), 680 (4.64), 816 (4.13) nm; MS (FAB (3-NBA+$CHCl_3$ matrix)) m/e calc'd for $C_{74}H_{87}N_{10}{}^{58}Ni^{60}Ni$: 1233.5757, found 1233.57831; 1233 ($M^+$+1, 42%); Analysis calc'd for $C_{74}H_{86}N_{10}\cdot HCl$: C, 70.02; H, 6.91; N, 11.03; found: C, 69.98; H, 6.85; N. 10.93: Singlet Oxygen Test: Negative.

(120) Free base dimer

The nickel dimer (Ni-120) (5 mg, 0.004 mmol) was dissolved in concentrated sulfuric acid (1 mL). The solution was stirred at room temperature for 2 hours, then poured into water, and extracted 3 times with dichloromethane. The solvent was dried and evaporated, and the residue was suspended in methanol and filtered to give the product as a grey solid (3.5 mg, 77% yield).

m.p. >300° C.; $R_F$ 0.33 (silica—$CH_2Cl_2$:hexanes 1:1); $^1H$ NMR (400 MHz, $CDCl_3$) δ 0.04 (t, J=7.5 Hz, 12H, 4× $CH_3$ of gem-diEt), 1.48–1.80 (m, 36H, 12× $CH_3$), 2.88–3.02 (m, 4H, 2× $CH_2$), 3.23–3.46 (m, 16H, 8× $CH_2$), 3.67 (q, J=7.5 Hz, 4H, 2× $CH_2$), 4.00–4.23 (m, 4H, 2× $CH_2$), 4.63 (q, J=7.5 Hz, 4H, 2× $CH_2$), 4.97 (br s, 2H), 5.82 (br s, 2H), 7.69 (s, 2H, 2 meso-H's), 7.88 (s, 2H, 2 meso-H's), 8.67 (s, 2H, 2 meso-H's); UV-Vis ($CH_2Cl_2$) $\lambda_{max}$ 400, 500, 572, 620, 678, 686, 742, 814 nm; MS (FAB (3-NBA+$CHCl_3$ matrix)) m/e calc'd for $C_{74}H_{91}N_{10}$: 1119.74262, found 1119.74164; 1120 ($M^+$+1, 17%); Singlet Oxygen Test: Positive.

(Zn-120) Zinc dimer

The free base dimer (120) (5 mg, 0.004 mmol) was dissolved in chloroform (5 mL) and zinc acetate dihydrate (10 mg, 0.046 mmol) in methanol (1 mL) was added. The mixture was refluxed 1 hour, then the solvent was evaporated, the residue was suspended in methanol, and this suspension was filtered to give quantitative dark green solid product.

m.p. >300° C.; $R_F$ 0.32 (silica—$CH_2Cl_2$); $^1H$ NMR (200 MHz, $CDCl_3$) δ 0.02 (t, J=7.5 Hz, 12H, 4× $CH_3$ of gem-diEt), 1.46–1.88 (m, 36H, 12× $CH_3$), 2.84–3.06 (m, 4H, 2×$CH_2$), 3.32–3.58 (m, 16H, 8× $CH_2$), 3.68 (q, J=7.5 Hz, 4H, 2× $CH_2$), 4.01–4.24 (m, 4H, 2× $CH_2$), 4.67 (q, J=7.5 Hz, 4H, 2× $CH_2$), 7.88 (s, 2H, 2 meso-H's), 8.23 (s, 2H, 2 meso-H's), 8.91 (s, 2H, 2 meso-H's); UV-Vis ($CH_2Cl_2$) $\lambda_{max}$ 392, 466, 494, 518, 628, 680, 688, 728, 818 nm; MS (FAB (thioglycerol matrix)) m/e 1248 ($M^+$, 100%).

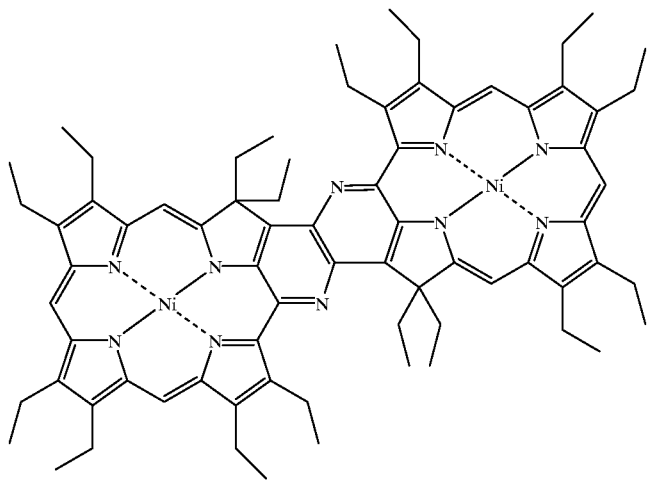

(Ni-121) Nickel ethylidene dimer

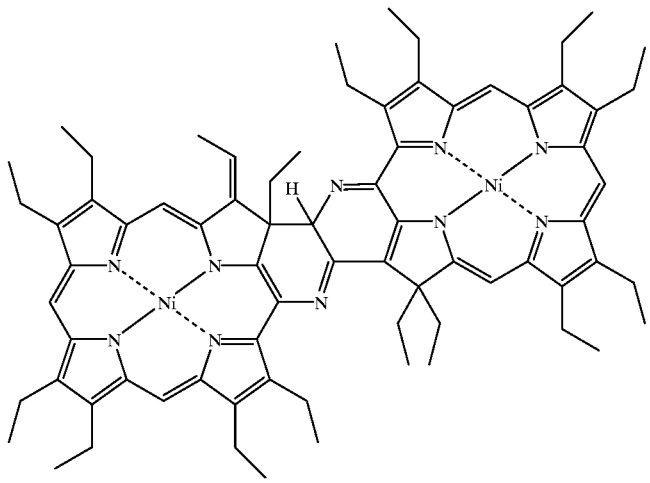

Formed in low yield as a side-product during the synthesis of (Ni-120).

$R_F$ 0.39 (silica—$CH_2Cl_2$:hexanes 1:1); $^1$H NMR (400 MHz, $CDCl_3$) δ (selected resonances), 0.27 (t, 3H, $CH_3$ of one gem-diEt group), 0.91 (t, 3H, $CH_3$ of one gem-diEt group), 2.82 (d, 3H, $\underline{CH_3}$=CH), 5.46 (s, 1H, angular CH), 8.33 (q, 1H, $\underline{CH}$=$CH_3$), 8.84, 8.99, 9.03. 9.38, 9.42, 9.46 (6s, 6H, 6 meso-H's); UV-Vis ($CH_2Cl_2$) $\lambda_{max}$ 410, 500, 626 nm; MS (FAB (matrix 3-NBA+$CHCl_3$)) m/e calc'd for $C_{74}H_{86}N_{10}{}^{58}Ni^{60}Ni$: 1232.61802, found 1232.57458; 1233 ($M^+$, 2%).

(Zn-92) (5-Formylmethyliminooctaethylporphyrinato)zinc (II)

The zinc aminoporphyrin (Zn-91) (100 mg, 0.16 mmol) was dissolved in THF (5 mL) and a solution of glyoxal trimer dihydrate (125 mg, 0.59 mmol) in ethanol (5 mL) was added. The mixture was refluxed for 8 hours, then the solvent was evaporated and the residue purified by chromatography (silica, eluent dichloromethane) to give the product (73 mg, 70% yield).

$R_F$ 0.74 (silica—$CH_2Cl_2$); $^1$H NMR (200 MHz, $CDCl_3$) δ 1.60–2.00 (m, 24H, 8× $CH_3$), 3.80–4.25 (m, 16H, 8× $CH_2$), 7.57 (d, J=8.1 Hz, 1H, $\underline{CH}$=CHO), 9.77 (s, 1H, 1 meso-H), 9.91 (s, 2H, 2 meso-H's), 10.30 (d, J=8.1 Hz, 1H, CHO); UV-Vis ($CH_2Cl_2$) $\lambda_{max}$ 408, 468, 544, 612 nm; MS (EI) m/e 651 ($M^+$, 100%).

(Zn-123) [Octaethyl-(3-hydroxypyrido)chlorinato]zinc(II)

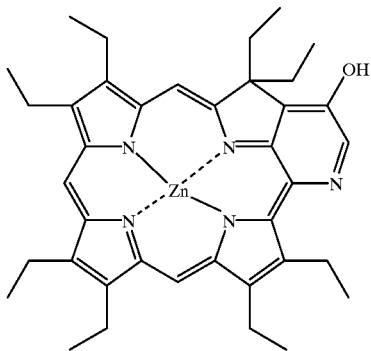

The zinc formylmethylimine (Zn-92) (93 mg, 0.14 mmol) was dissolved in toluene (10 mL) and activated Montmorillonite clay (50 mg) was added. The mixture was refluxed for 72 hours, then filtered and the solvent evaporated. The residue was purified by chromatography (silica, eluent initially dichloromethane, increasing polarity to 5% methanol in dichloromethane) to give unreacted starting material (59 mg) and the slightly impure product (20 mg, 22% yield).

$R_F$ 0.58 (silica—10% $AcOEt/CH_2Cl_2$); $^1$H NMR (200 MHz, pyridine-$d_5$) δ 0.33 (t, J=7.1 Hz, 6H, 2× $CH_3$ of gem-diEt), 1.58–2.01 (m, 18H, 6× $CH_3$), 2.62–2.82 (m, 2H, 2× CH of gem-diEt $CH_2$), 3.43–3.92 (m, 12H, 6× $CH_2$), 4.45 (q, J=7.6 Hz, 2H, 2× CH of gem-diEt $CH_2$), 8.23, (s, 1H, $\underline{CH}$ of pyridine ring), 9.15 (s, 1H, 1 meso-H), 9.60 (s, 1H, 1 meso-H) 9.62 (s, 1H, 1 meso-H); UV-Vis ($CH_2Cl_2$) $\lambda_{max}$ 410, 422, 518, 558, 574, 624, 678 nm; MS (EI) m/e 651 ($M^+$, 100%); Singlet Oxygen Test: Negative.

(123) Octaethyl-(3-hydroxypyrido)chlorin

The zinc chlorin (Zn-123) (20 mg, 0.030 mmol) was dissolved in dichloromethane (5 mL) and TFA (2 drops) was added. The solution was stirred for 2 hours, then pyridine (5 drops) was added to neutralize and the solvent was evaporated. The residue was chromatographed (silica, eluent 5% methanol in dichloromethane) to give the product (6 mg, 35% yield).

$R_F$ 0.70 (silica—10% $AcOEt/CH_2Cl_2$); $^1$H NMR (400 MHz, pyridine-$d_5$) δ 0.40 (t, J=7.3 Hz, 6H, 2× $CH_3$ of gem-diEt), 1.63–1.81 (m, 15H, 5× $CH_3$), 1.88 (t, J=7.3 Hz, 3H, 1× $CH_3$), 2.78–2.91 (m, 2H, $CH_2$), 3.49–3.71 (m, 10H, 5× $CH_2$), 3.85 (q, J=7.5 Hz, 2H, 2× CH of gem-diEt $CH_2$), 4.43 (q, J=7.3 Hz. 2H, 2× CH of gem-diEt $CH_2$), 8.40, 8.99, 9.58, 9.69 (4s, 3 meso-H's and $\underline{CH}$=N) 13.06 (br s, 1H, OH); UV-Vis ($CHCl_3$ (log ε)) $\lambda_{max}$ 412 (4.89), 490 (3.51), 522 (3.73), 556 (3.75), 616 (3.86), 672 (4.36) nm; MS (EI) m/e calc'd for $C_{38}H_{47}N_5O$: 589.37805, found 589.37791; 589 ($M^+$, 100%), 560 (($M-29)^+$, 65%)): Analysis caic'd for $C_{38}H_{47}N_5O \cdot 0.5H_2O$: C, 76.22; H, 8.08; N, 11.70; found: C, 75.96; H, 7.64; N, 11.67; Singlet Oxygen Test: Positive.

We claim:

1. A compound according to the formula

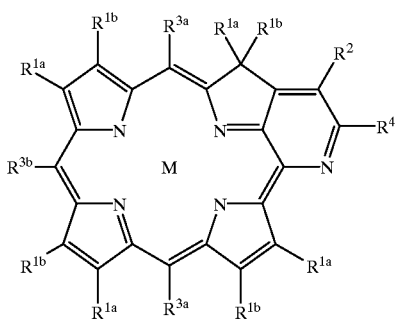
(1)

wherein, $R^{1a}$, $R^{1b}$ are independently H or alkyl;

$R^2$ is OH, halogen, alkoxy, OCO-alkyl, sulfonate, sulfate, or phosphate;

$R^{3a}$ is H, or a phenyl or other aryl or heteroaryl group optionally substituted by one or more groups, each independently selected from halogen, hydroxy, alkyl, alkoxy, cyano, and ester;

$R^{3b}$ is H, halogen, formyl, nitro, amino or cyano;

$R^4$ is H or alkyl;

M is a porphyrin-complexing metal, typically known in the art, or represents 2H; and N, the nitrogen atom of the pyridine ring, is optionally in the form of an N-oxide, or a salt such as an alkyl or hydrogen halide.

2. A pharmaceutical composition comprising a compound according to claim 1 and at least one substance that faciliates the therapeutic application thereof.

3. A compound selected from the group consisting of:

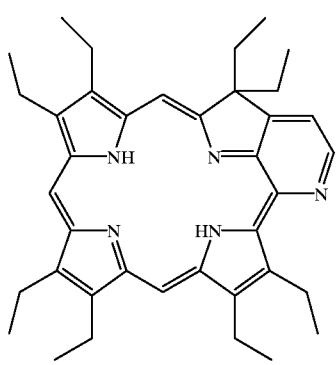

α-isomer

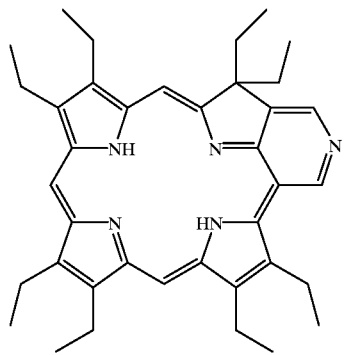

β-isomer

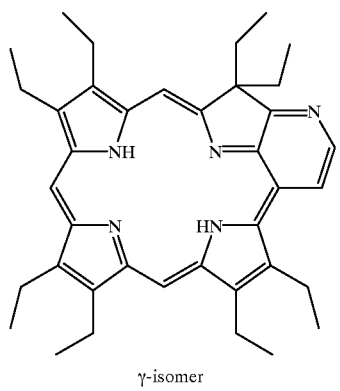

γ-isomer

4. A compound selected from the group consisting of:

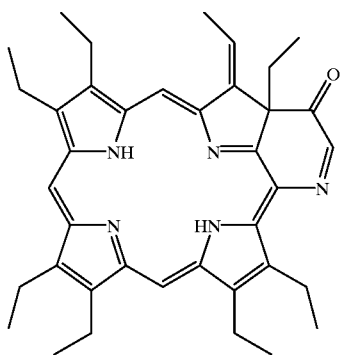

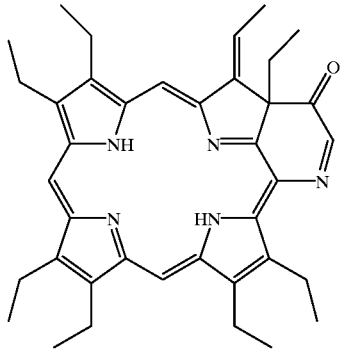

* * * * *